(12) United States Patent
LaCasse et al.

(10) Patent No.: US 7,638,497 B2
(45) Date of Patent: *Dec. 29, 2009

(54) ANTISENSE IAP NUCLEOBASE OLIGOMERS AND USES THEREOF

(75) Inventors: Eric LaCasse, Ottawa (CA); Daniel McManus, Ottawa (CA); Jon P. Durkin, Ottawa (CA)

(73) Assignee: Aegera Therapeutics, Inc., Verdun, Quebec ( * ) Notice: Subject to any disclaimer, the term of this patent is extended or adjusted under 35 U.S.C. 154(b) by 0 days.

This patent is subject to a terminal disclaimer.

(21) Appl. No.: 11/477,452

(22) Filed: Jun. 30, 2006

(65) Prior Publication Data

US 2007/0049544 A1 Mar. 1, 2007

Related U.S. Application Data

(63) Continuation of application No. 10/400,382, filed on Mar. 27, 2003, now Pat. No. 7,091,333.

(60) Provisional application No. 60/367,853, filed on Mar. 27, 2002.

(51) Int. Cl.
*A61K 31/70* (2006.01)
*C07H 21/04* (2006.01)
*C12N 15/00* (2006.01)

(52) U.S. Cl. .................. 514/44; 536/24.5; 435/320.1

(58) Field of Classification Search .................. None
See application file for complete search history.

(56) References Cited

U.S. PATENT DOCUMENTS

| | | | |
|---|---|---|---|
| 5,510,239 A | 4/1996 | Baracchini et al. | |
| 5,576,208 A | 11/1996 | Monia et al. | |
| 5,594,076 A | 1/1997 | Gordon et al. | |
| 5,605,022 A | 2/1997 | Fulton | |
| 5,624,803 A | 4/1997 | Noonberg et al. | |
| 5,665,550 A | 9/1997 | Roninson et al. | |
| 5,691,179 A | 11/1997 | Korsmeyer | |
| 5,718,883 A | 2/1998 | Harlan et al. | |
| 5,770,690 A | 6/1998 | Bitler et al. | |
| 5,801,154 A * | 9/1998 | Baracchini et al. | ............ 514/44 |
| 5,834,216 A | 11/1998 | Roizman et al. | |
| 5,919,912 A | 7/1999 | Korneluk et al. | |
| 5,958,771 A | 9/1999 | Bennett et al. | |
| 5,958,772 A | 9/1999 | Bennett et al. | |
| 5,994,076 A | 11/1999 | Chenchik et al. | |
| 5,998,148 A | 12/1999 | Bennett et al. | |
| 6,020,127 A | 2/2000 | MacKenzie | |
| 6,087,173 A | 7/2000 | Bennett et al. | |
| 6,107,041 A | 8/2000 | Korneluk et al. | |
| 6,133,246 A | 10/2000 | McKay et al. | |
| 6,133,437 A | 10/2000 | Korneluk et al. | |
| 6,156,535 A | 12/2000 | Korneluk et al. | |
| 6,187,557 B1 | 2/2001 | Rothe et al. | |
| 6,228,603 B1 | 5/2001 | Reed et al. | |
| 6,265,157 B1 | 7/2001 | Prockop et al. | |
| 6,300,492 B1 | 10/2001 | Korneluk et al. | |
| 6,395,771 B1 | 5/2002 | Ramadoss et al. | |
| 6,417,160 B1 | 7/2002 | Tatton et al. | |
| 6,492,427 B2 | 12/2002 | Shankar et al. | |
| 6,506,559 B1 | 1/2003 | Fire et al. | |
| 6,656,704 B1 | 12/2003 | Korneluk et al. | |
| 6,673,917 B1 * | 1/2004 | Korneluk et al. | ........... 536/24.5 |
| 6,946,544 B2 | 9/2005 | Korneluk et al. | |
| 7,087,584 B2 | 8/2006 | Korneluk et al. | |
| 7,091,333 B2 | 8/2006 | LaCasse et al. | |
| 7,294,713 B2 | 11/2007 | Korneluk et al. | |
| 2002/0119168 A1 * | 8/2002 | Rudnic et al. | ............... 424/400 |
| 2002/0168631 A1 | 11/2002 | Park et al. | |
| 2003/0073159 A1 | 4/2003 | He et al. | |
| 2003/0190659 A1 | 10/2003 | LaCasse et al. | |
| 2005/0153919 A1 | 7/2005 | Paolo et al. | |

FOREIGN PATENT DOCUMENTS

| | | |
|---|---|---|
| CA | 2343102 | 4/2000 |
| CA | 2353108 | 6/2000 |
| CA | 2480308 | 10/2003 |
| WO | WO 94/06814 | 3/1994 |
| WO | WO 95/19431 | 7/1995 |
| WO | WO 95/028497 A1 | 10/1995 |
| WO | WO 95/30435 A2 | 11/1995 |
| WO | WO 96/12016 | 4/1996 |
| WO | WO 96/12737 A2 | 5/1996 |
| WO | WO 96/20950 A2 | 7/1996 |
| WO | WO 96/35703 A1 | 11/1996 |
| WO | WO 97/06182 | 2/1997 |
| WO | WO 97/06255 | 2/1997 |
| WO | WO 97/023501 A1 | 7/1997 |
| WO | WO 97/26331 | 7/1997 |

(Continued)

OTHER PUBLICATIONS

Elbashir et al. EMBO Journal 2001, vol. 20, pp. 6877-6888.*
Agrawal et al., "Antisense Therapeutics," *Curr. Opin. Chem. Biol.* 2:519-528 (1998).
Andreeff et al., "Inhibitor-of-apoptosis (IAP) Proteins XIAP and Survivin in Primary Acute Myelogenous Leukemias (AML): Regulation and Therapeutic Targets," Proceedings Annual Meeting of the American Association for Cancer Research, *Abstract* 41:739-740 (2000).
Birnbaum et al., "An Apoptosis-inhibiting Gene From a Nuclear Polyhedrosis Virus Encoding a Polypeptide with Cys/His Sequence Motifs," *J. Virol.* 68:2521-2528 (1994).
Branch, "A Good Antisense Molecule Is Hard To Find," *Trends Biochem. Sci.* 23: 45-50 (1998).
Campbell, "Monoclonal Antibody Technology," Elsevier Science, Publishers B.V. New York, NY, (1984).

(Continued)

*Primary Examiner*—Tracy Vivlemore
(74) *Attorney, Agent, or Firm*—Leydig, Voit & Mayer, Ltd.

(57) ABSTRACT

The present invention features nucleobase oligomers that hybridize to IAP polynucleotide, and methods for using them to enhance apoptosis and treat proliferative disorders.

44 Claims, 34 Drawing Sheets

FOREIGN PATENT DOCUMENTS

| | | |
|---|---|---|
| WO | WO 98/22131 | 5/1998 |
| WO | WO 98/022131 A2 | 5/1998 |
| WO | WO 98/35693 | 8/1998 |
| WO | WO 00/05366 | 2/2000 |
| WO | WO 00/32816 | 6/2000 |
| WO | WO 00/32818 | 6/2000 |
| WO | WO 00/61595 | 10/2000 |
| WO | WO 01/18024 | 3/2001 |
| WO | WO 02/26968 | 4/2002 |
| WO | WO 03/076592 A2 | 9/2003 |
| WO | WO 03/080638 A2 | 10/2003 |
| WO | WO 2004/091388 A1 | 10/2004 |
| WO | WO 2005/042030 | 5/2005 |

OTHER PUBLICATIONS

Cheng et al., "Characterisations of Taxol-induced Apoptosis and Altered Gene Expression in Human Breast Cancer Cells," *Cellular Pharmacol.* 2: 249-257 (1995).

Cheng et al., "Staurosporine, K-252a, And K-252b Stabilize Calcium Homeostasis and Promote Survival of CNS Neurons in the Absence of Glucose," *J. Neurochem.* 62:1319-1329 (1994).

Chirila et al., "The Use of Synthetic Polymers for Delivery of Therapeutic Antisense Oligodeoxynucleotides," *Biomaterials* 23: 321-342 (2002).

Clem et al., "Prevention of Apoptosis by a Baculovirus Gene During Infection of Insect Cells," *Science* 254:1388-1390 (1991).

Clem et al., "Control of Programmed Cell Death by the Baculovirus Genes *p35* And *iap*," *Mol. Cel. Biol.* 14:5212-5222 (1994).

Clem et al., "Anti-apoptotic Genes of Baculoviruses," *Cell Death and Differentiation* 3:9-16 (1996).

Crook et al., "An Apoptosis-inhibiting Baculovirus Gene with a Zinc Finger-like Motif," *J. Virol.* 67:2168-2174 (1993).

Dhein et al., "Autocrine T-cell Suicide Mediated by APO-1/(Fas/CD95)," *Nature* 373:438-441 (1995).

Dierlamm et al., "The Apoptosis Inhibitor Gene API2 and a Novel 18q Gene, MLT, Are Recurrently Rearranged in the t(11;18)(q21;q21) Associated with Mucosa-Associated Lymphoid Tissue Lymphomas," *Blood* 93: 3601-3609 (1999).

Duckett et al., "A Conserved Family of Cellular Genes Related to the Baculovirus IAP Gene and Encoding Apoptosis Inhibitors," *EMBO J.* 15:2685-2694 (1996).

Erl et al., "Nuclear Factor-kappa B Regulates Induction of Apoptosis and Inhibitor of Apoptosis Protein-1 Expression in Vascular Smooth Muscle Cells," *Cir. Res.* 84:668-677 (1999).

Fallo et al., "Effects of Taxol on the Human NCI-H295 Adrenocortical Carcinoma Cell Line," *Endocr. Res.* 22: 709-715 (1996).

Fernandez et al., "Differential Sensitivity of Normal and Ha-ras-transformed C3H Mouse Embryo Fibroblasts to Tumor Necrosis Factor: Induction of bcl-2, c-myc, and Manganese Superoxide Dismutase in Resistant Cells," *Oncogene* 9:2009-2017 (1994).

Ferrari et al., "N-acetylcysteine (D- and L-stereoisomers) Prevents Apoptotic Death of Neuronal Cells," *J. Neurosci.* 15:2857-2866 (1995).

Fisher et al., "Dominant Interfering Fas Gene Mutations Impair Apoptosis in a Human Autoimmune Lymphoproliferative Syndrome," *Cell* 81:935-946 (1995).

Francis et al., "The Response Of GABAergic and Cholinergic Neurons to Transient Cerebral Ischemia," *Brain Res.* 243:271-278 (1982).

Galderisi et al., "Antisense Oligonucleotides as Therapeutic Agents," *J. Cell. Physio.* 181: 251-257 (1999).

Gewirtz, "Antisense Oligonucleotide Therapeutics for Human Leukemia," *Curr. Opin. Hematol.* 5 : 59-71 (1998).

Gibellini et al., "Tat-expressing Jurkat Cells Show an Increased Resistance to Different Apoptotic Stimuli, Including Acute Human Immunodeficiency Virus-type 1 (HIV-1) Infection," *Br. J. Haematol.* 89:24-33 (1995).

Glicksman et al., "K-252a and Staurosporine Promote Choline Acetyltransferase Activity in Rat Spinal Cord Cultures," *J. Neurochem.* 61:210-221 (1993).

Glicksman et al., "A K-252a Analog Prevents Developmentally Programmed Motoneuron Death and the Loss of Chat Activity in Adult Motoneurons In Vivo," *Soc. Neuro. Abst.* 441 (1994).

Glicksman et al., "K-252a Promotes Survival and Choline Acetyltransferase Activity in Striatal and Basal Forebrain Neuronal Cultures," *J. Neurochem.* 64:1502-1512 (1995).

Golstein et al., "Homology Between Reaper and the Cell Death Domains of Fas and TNFR1," *Cell* 81:185-186 (1995).

Goruppi et al., "Dissection of c-myc Domains Involved in S Phase Induction of NIH3T3 Fibroblasts," *Oncogene* 9:1537-1544 (1994).

Harrington et al., "c-Myc-induced Apoptosis in Fibroblasts is inhibitied by Specific Cytokines," *EMBO J.* 13:3286-3295 (1994).

Holcik, et al. "Translational Upregulaton of X-Linked Inhibitor of Apoptosis (XIAP) Increases Resistance to Radiation Induced Cell Death," *Oncogene* 19:4174-4177 (2000).

Holcik et al., "XIAP: Apoptotic Brake and Promising Therapeutic Target," *Apoptosis* 6:253-261 (2001).

Hu et al., "Antisense Oligonucleotides Targeting XIAP Induce Apoptosis and Enhance Therapeutic Activity Against Human Lung Cancer Cells When Combined With Anticancer Drug in Vitro and in Vivo," Proceedings of the America Association for Cancer Research Annual Meeting 43:576 (2002).

Itoh et al., "A Novel Protein Required for Apoptosis. Mutational Analysis of Human Fas Antigen," *J. Biol. Chem.* 268:10932-10937 (1993).

Jansen et al., "Chemosensitisation of malignant melanoma by BCL2 antisense therapy," *Lancet* 356: 1728-1733 (2000).

Jansen et al., "Antisense therapy for cancer-the time of truth," *Lancet Oncol.* 3:672-683 (2002).

Jen et al., "Suppression of Gene Expression by Targeted Disruption of Messenger RNA: Available Options and Current Strategies," *Stem Cells* 18:307-319 (2000).

Jones et al., "Deterin, a New Inhibitor of Apoptosis from Drosophila Melanogaster," *J. Biol. Chem.* 275 : 22157-22165 (2000).

Katsikis et al., "Fas Antigen Stimulation Induces Marked Apoptosis of T Lymphocytes In Human Immunodeficiency Virus-infected Individuals," *J. Exp. Med.* 181:2029-2036 (1995).

Kerr, "Neglected Opportunities in Apoptosis Research," *Trends Cell Biol.* 5:55-57 (1995).

Korsmeyer, "Regulators of Cell Death," *Trends Genet.* 11:101-105 (1995).

Lacasse, et al., "The Inhibitors of Apoptosis (IAPs) and Their Emerging Role in Cancer," *Oncogene* 17:3247-3259 (1998).

Li et al., "Induction of Apoptosis in Uninfected Lymphocytes by HIV-1 Tat Protein," *Science* 268:429-431 (1995).

Li et al., "Pleiotropic Cell-division Defects and Apoptosis Induced by Interference with Survivin Function," *Nat. Cell Biol.* 1:461-466 (1999).

Lin et al., "Resistance of Bone Marrow-derived Macrophages to Apoptosis Is Associated With the Expression of X-linked Cultures of Bone Marrow Cells," *Biochemical Journal* 353:299-306 (2001).

Liston et al., "Suppression of Apoptosis in Mammalian Cells by NAIP and a Related Family of IAP Genes," *Nature* 379:349-353 (1996).

Martin et al., "HIV-1 Infection of Human CD4+ T Cells in Vitro. Differential Induction Of Apoptosis In These Cells," *J. Immunol.* 152:330-342 (1994).

Melino et al., "Tissue Transglutaminase and Apoptosis: Sense and Antisense Transfection Studies with Human Neuroblastoma Cells," *Mol. Cell. Biol.* 14:6584-6596 (1994).

Murayama et al., "Immunocytochemical and Ultrastructural Studies of Werdnig-Hoffmann Disease," *Acta Neuropathol,* 81:408-417 (1991).

Muro-Cacho et al., "Analysis Of Apoptosis in Lymph Nodes Of HIV-infected Persons. Intensity of Apoptosis Correlates with the General State of Activation of the Lymphoid Tissue and not with Stage of Disease or Viral Burden," *J. Immunol.* 154:5555-5566 (1995).

Nakanishi et al., "K-252a, a Novel Microbial Product, Inhibits Smooth Muscle Myosin Light Chain Kinase," *J. Biol. Chem.* 263:6215-6219 (1988).

Norris et al., Cancer Gene Therapy: Past Achievements and Future Challenges, "Design and Testing of Ribozymes for Cancer Gene therapy," Kluwer Academic/Plenum Publishers, New York, pp. 293-301 (2000).
Nunez et al., "The Bcl-2 Family of Proteins: Regulators of Cell Death and Survival," *Trends Cell Biol.* 4:399-403 (1994).
Olie, et al., "A Novel Antisense Oligonucleotide Targeting Survivin Expression Induces Apoptosis and Sensitizes Lung Cancer Cells to Chemotherapy," *Cancer Res.* 60:2805-2809 (2000).
Osborne et al., "Essential Genes that Regulate Apoptosis," *Trends Cell Biol.* 4:394-399 (1994).
Peterson et al., "Loss Of GABAergic neurons in Medial Septum After Fimbria-fornix Transection," *Neurosci. Lett.* 76:140-144 (1987).
Pulsinelli et al., "Temporal Profile of Neuronal Damage in a Model of Transient Forebrain Ischemia," *Ann. Neurol.* 11:491-498 (1982).
Rabizadeh et al., "Expression of the Baculovirus p35 Gene Inhibits Mammalian Neural Cell Death," *J. Neurochem.* 61:2318-2321 (1993).
Ridoux et al., "The Use of Adenovirus Vectors for Intracerebral Grafting of Transfected Nervous Cells," *Neuroreport.* 5:801-804 (1994).
Ridoux et al., "Adenoviral Vectors as Functional Retrograde Neuronal Tracers," *Brain Res.* 648:171-175 (1994).
Ridoux et al., "Ex Vivo Culture of Adult Microglial Cells from Previously Lesioned Rat Brains," *C.R. Acad. Sci. III* 317:217-224 (1994).
Rieux-Laucat et al., "Mutations in Fas Associated with Human Lymphoproliferative Syndrome and Autoimmunity," *Science* 268:1347-1349 (1995).
Rosenbaum et al., "Evidence For Hypoxia-induced, Programmed Cell Death Of Cultured Neurons," *Ann. Neurol.* 36:864-870 (1994).
Rothe et al., "The TNFR2-TRAF Signaling Complex Contains Two Novel Proteins Related to Baculoviral Inhibitor of Apoptosis Proeteins," *Cell* 83:1243-1252 (1995).
Roy et al., "The Gene for Neuronal Apoptosis Inhibitory Protein is Partially Deleted in Individuals with Spinal Muscular Atrophy," *Cell* 80:167-178 (1995).
Sasaki, et al., "Down-regulation of X-Linked Inhibitor of Apoptosis Protein Induces Apoptosis in Chemoresistant Human Ovarian Cancer Cells," *Cancer Res.* 60:5659-5666 (2000).
Sato et al., "Neuronal Differentiation Of PC12 Cells as a Result of Prevention of Cell Death by bcl-2," *J. Neurobiol.* 25:1227-1234 (1994).
Sauer et al., "Progressive Degeneration of Nigrostriatal Dopamine Neurons Following Intrastriatal Terminal Lesions with 6-hydroxydopamine: A Combined Retrograde Tracing And Immunocytochemical Study in the Rat," *Neurosci.* 59:401-415 (1994).
Semba et al., "Organization of Central Cholinergic Systems," *Prog. Brain Res.* 79:37-63 (1989).
Smith-Swintosky et al., "K252A, K252B and Staurosporine Increase Hippocampal Neuron Survival and Improve Water Maze Performance After Kainate Lesion," *Soc. Neuro. Abst.* 2130 (1995).
Steiman et al., "Infantile Neuronal Degeneration Masquerading as Werdnig-Hoffmann Disease," *Ann. Neurol.* 8:317-324 (1980).
Stein, "How To Design An Antisense Oligodeoxynucleotide Experiment: A Consensus Approach," *Antisense & Nucleic Acid Drug Development* 8:129-132 (1998).
Stein, "Is Irrelevant Cleavage the Price of Antisense Efficacy?" *Pharmacol Ther.* 85:231-236 (2000).
Steller, "Mechanisms and Genes of Cellular Suicide," *Science* 267:1445-1449 (1995).
Talley et al., "Tumor Necrosis Factor Alpha-induced Apoptosis in Human Neuronal Cells: Protection by the Antioxidant N-acetylcysteine and the Genes bcl-2 and crmA," *Mol. Cell. Biol.* 15:2359-2366 (1995).
Terai et al., "Apoptosis as a Mechanism of Cell Death in Cultured T-lymphoblasts Acutely Infected with HIV-1," *J. Clin. Invest.*, 87:1710-1715 (1991).
Tetzlaff et al., "Changes in Cytoskeletal Proteins in the Rat Facial Nucleus Following Axotomy," *J. Neurosci.* 8:3181-3189 (1988).
Towfighi et al., "Is Werdnig-Hoffman Disease a Pure Lower Motor Neuron Disorder?," *Acta Neuropathol.* 65:270-280 (1985).

Turner et al., "Ribozymes: Their Design and Use in Cancer," *Adv. Exp. Med. Biol.* 465:303-318 (2000).
Vossbeck et al., "Direct Transforming Activity of TGF-beta on Rat Fibroblasts," *Int. J. Cancer* 61:92-97 (1995).
Walkinshaw et al, "Induction of Apoptosis in Catecholaminergic PC12 Cells by L-DOPA. Implications for the Treatment of Parkinson's Disease," *J. Clin. Invest.* 95:2458-2464 (1995).
Westendorp et al., "Sensitization of T Cells to CD95-mediated Apoptosis by HIV-1 Tat And gp120," *Nature* 375:497-500 (1995).
White et al., "Genetic Control of Programmed Cell Death in Drosophila," *Science* 264:677-683 (1994).
Williams et al., "Apoptosis: Final Control Point in Cell Biology," *Trends Cell Biol.* 2:263-267 (1992).
Wyllie, "Apoptosis. Death Gets A Brake," *Nature* 369:272-273 (1994).
Xu et al., "Elevation Of Neuronal Expression Of NAIP Reduces Ischemic Damage In The Rat Hippocampus," *Nat. Med.* 3:997-1004 (1997).
Xu et al., "Distribution Of Neuronal Apoptosis Inhibitory Protein-Like Immunoreactivity in the Rat Central Nervous System," *J. Comp. Neurol.* 382:247-259 (1997).
Zuker et al., "Algorithms and Thermodynamics for RNA Secondary Structure Prediction: A Practical Guide," In *RNA Biochemistry and Biotechnology*, J. Barciszewski & B.F.C. Clark, eds., NATO ASI Series, Kluwer Academic Publishers, (1999).
Antoni et al., J. of Virol., 69:2384-2392 (1995).
Bilim et al., Intl. J. of Cancer, 103(1):29, (2003).
Chai et al., Cell, 104:769-780 (2001).
Chai et al., Nature, 406:855-862 (2000).
Chawla-Sarkar et al., Cell Death Diff., 11(8):915-923 (2004).
Clem et al., Mol. and Cell Biology, 14:5212 (1994).
Crystal, Science 270:404-410 (1995).
Deveraux et al., Genes & Dev. 13(3):239-252 (1999).
Dupressoir et al., Mol. Cell. Biol., 16:4495-4503 (1996).
Eckelman et al., J. Biol. Chem., 281(6):3254-3260 (2006).
Gao et al., J. Biol. Chem., 282(42):30718-30727 (2007).
Gardner et al., Int J Dev. Biol., 41:235-243 (1997).
Hatano et al., J. Neurosurgery, 101(1):119-127 (2004).
Hillier et al., GenBank Accession No. T96284 (1995).
Hu et al., Clin. Cancer Res. 9 :2826, (2003).
Huang et al., Cell, 104:781-790 (2001).
Laneuville et al., Cancer Research, 54(5):1360-6 (1994).
Li et al., Endocringy, 139(3):1321-1328 (1998).
Li et al., Endocrinology, 142(1):370 (2001).
Lima et al., Cancer Gene Therapy, 11(5):309-316 (2004).
Liston et al., Ongene, 22:8568-8580 (2003).
Maldarelli et al., J. Virol., 69(10):6457-65 (1995).
Mcmanus et al., RNA 8:842-850 (2002).
Mishra et al., J. Biol. Chem., 280(45):37536 (2005).
Mulligan, Science 260:926-932 (1993).
Nagata et al., Science, 267:1449-1456 (1995).
Ngo et al., in the Protein Folding Problem and Tertiary Structure Prediction, Merz et al. (eds.), Birkhauser Boston, Bostin, MA pp. 433 and 492-495 (1994).
Rothe et al., GenCore Accession No. L49433 (1996).
Rudinger, in Peptid Hormones, Parsons (ed.), University Park Press, Baltimore, MD pp. 1-7 (1976).
Shi et al., Protein Sci., 13:1979-1987 (2004).
Smith et al., Endocrinology, 133(3):1085-91 (1993).
Srinivasula et al., J. Biol.Chem., 275(46):36152-36157 (2000).
Suzuki et al., J. Biol. Chem., 276(29):27058-27063 (2001).
Takahashi et al., J. Biol. Chem., 273(14):7787-7790 (1998).
Tuschl et al, Molecular Interventions, 2(3):158-167 (2002).
Verhagen et al., Genome Biol. 2(7):S3009.1-10 (2001).
Wang et al., J. Biol. Chem., 279(46):48168-48176 (2004).
Waters et al., J. Clin. Oncol., 18:1812 (2000).
Agrawal et al., Mol. Med. Today, 6:72-81 (2000).
Anderson, Nature 392 (Supp):25-30 (1998).
Ausubel et al., Short Protocols in Molecular Biology, 3$^{rd}$ Ed., Wiley & Sons Inc., pp. 9.1, 16.3-5 and 16.5862 (1992).
Bass, Nature, 411: 428-429 (2001).
Braasch et al., Biochemistry, (41)14:4503-4509 (2002).
Cameron, Mol. Biotechnol. 7:253-265 (1997).

Chawla-Sarkar et al., Euro. Cytokine Network, 14(Suppl 3): 112 (2003).
Clark et al., Pathology Oncology Research, 5:3-15 (1999).
Clem et al., Apoptosis II: The Molecular Basis of Apoptosis in Disease, Cold Spring Harbor Laboratory Press, p. 89 (1994).
Crooke, Antsense Res. & Application, Chapter 1, pp. 1-50, Ed. by S. Crooke, Publ. by Springer-Verlag (1998).
Dean et al., J. Clin. Oncol., 10.1200/JCO.2008.19.5677 (2009).
De Mesmaeker et al., Current Opinion in Structural Biology, 5:343 (1995).
Eck et al., Chapter 5, 9 77-101 (1995).
Fong et al., Genomics, 70:113-122 (2000).
Garcia et al, Histology and Histopathology, 10(1): 79-84 (1995).
Greenman et al., Nature 446:153-158 (2007).
Haapajarvi et al., Oncogene, 11(1):151-9 (1995).
Harlow et al., Antibodies: A Laboratory Manual, Cold Spring Harbor Laboratory, p. 76 (1989).
Holt, Mol. Med. Today, 2:184-185 (1996).
Ishizaki et al., Mol. Biol. of the Cell. 6: 1443-1458 (1995).
Lagace et al., Genomics, 77:181-188 (2001).
Lau et al., Cellular Immunol., 125(1):92-106 (1990).
Lerner, Nature, 299:592-596 (1982).
Letsinger et al., J. Amer. Chem. Soc., 97:3278-3279 (1975).
Liston et al., Apoptosis, 2:423 (1997).
Luque et al., Biochemistry, 41:13663-13671 (2002).
McManus et al., Oncogene 23(49): 8105-8117 (2004).
Mullins et al., J. Clin. Invest., 98(11):S37-S40 (1996).
NM_001167, Entrez Gene [onlin] {retrieved Jul. 23, 2008] www.ncbi.nlm.nih.gov/entrez.
Orkin et al., Report and Recommendations of the Panel to Access the NIH Investment in Research on Gene Therapy (1995).
Opalinska et al., Ann. N.Y. Acad. Sci., 1082:124 (2006).
Palmiter et al., Ann. Rev. Gen., 20:465-99 (1986).
Peracchi, Rev. Med. Virol., 14:47-64 (2004).
Robertson et al., Soc. Neurosci. Abstr., 654.8 (1996).
Robertson et al., Brain Pathology, 10(2):283-292 (2000).
Rojanasakul, Advanced Drug Delivery Reviews, 18:115-131 (1996).
Sherman, Annals of NY Acad. Sci., 616:201-204 (1990).
Stein, Antisense & Nucleic Acid Drug Dev., 8: 129-132 (1998).
Sun et al., J. Biol. Chem., 275:33777-33781 (2000).
Tachikawa et al., Current Opinion in Biotechnology, 17:659 (2006).
Tamm et al.,The Lancet, 2001, 358:489-497 (2001).
Verma, Nature 389:239-242 (1997).
Verreault et al., Current Gene Therapy, 6:505 (2006).
Wang et al., Oncogene, 8(12):3427-31 (1993).
Weil et al., Acta Crystallographica, D55:422-429 (1998).
Accession S69544, Q13490, Q13489, S68451, HSU45878, (1996) LISTON.
Chen et al., *Bioorg. Med. Chem. Lett.*, 16(22):5805-5808 (2006).
Crocker et al., *Soc. Neurosci. Abstr.*, 464.18 (1996).
Gold et al., *Mol. Med. Today*, 6:88-91 (2000).
Holcik et al., *Nat Rev Mol Cell Biol.*, 2(7):550-556 (2001).
McFarland et al., *Nature Immunol.*, 8(9):913-919 (2007).
Miranda et al., *Leukemia*, 17:390-400 (2003).
Moore et al., Business Briefing: *US Neurology Review*, p. 1-6, Jul. 2005.
Oost et al., *J. Med. Chem.*, 47(18):4417-26 (2004).
Pender et al., *Lancet*, 351(9107):978-981 (1998).
Sasaki et al. *FEBS Journal*, 275:6011-6021 (2008).
Schimmer et al., *Cancer Cell*, 5:25-35 (2004).
Seidi et al., *J. Neuroimmunol.*, 130:202-210 (2002).
Sharief et al., *J. Neuroimmunol.*, 129(1-2):224-231 (2002).
Sturzebecher et al., *Brain*, 126(Pt 6):1419-29 (2003).
'T Hart et al., *Drug Discov. Today*, 9(12):517-524 (2004).
Tamm et al., *J. Biol. Chem.*, 278(16):14401-14405 (2003).
Uren et al., *Proc. Natl. Acad. Sci. USA*, 93: 4974-4978 (1996).
Zehntner et al., *Clin. Immunol., Suppl.*, 1:S36-S37 (2005).
Zipp et al., *Cell Tissue Res.*, 301:163-171 (2000).

* cited by examiner

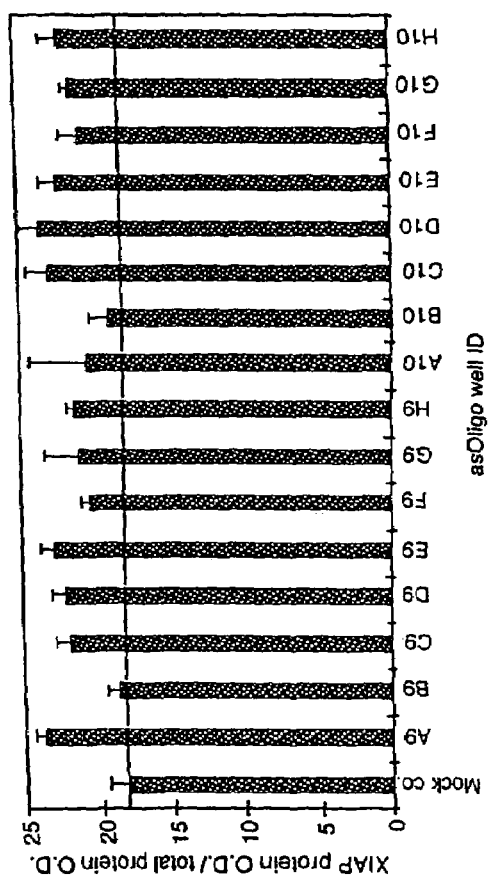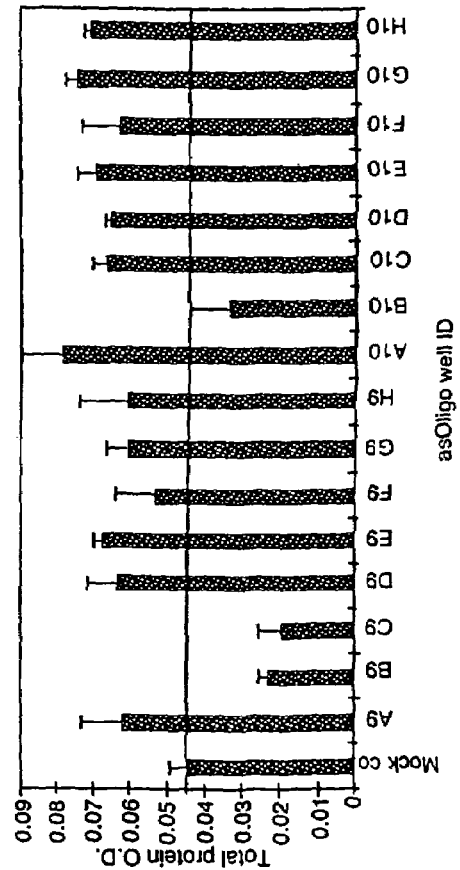
Figure 1I
Figure 1J

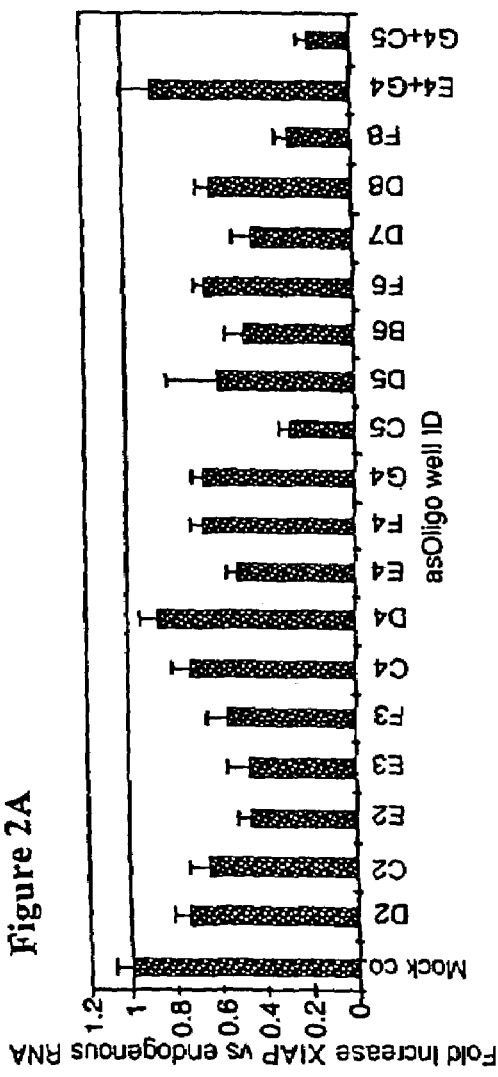
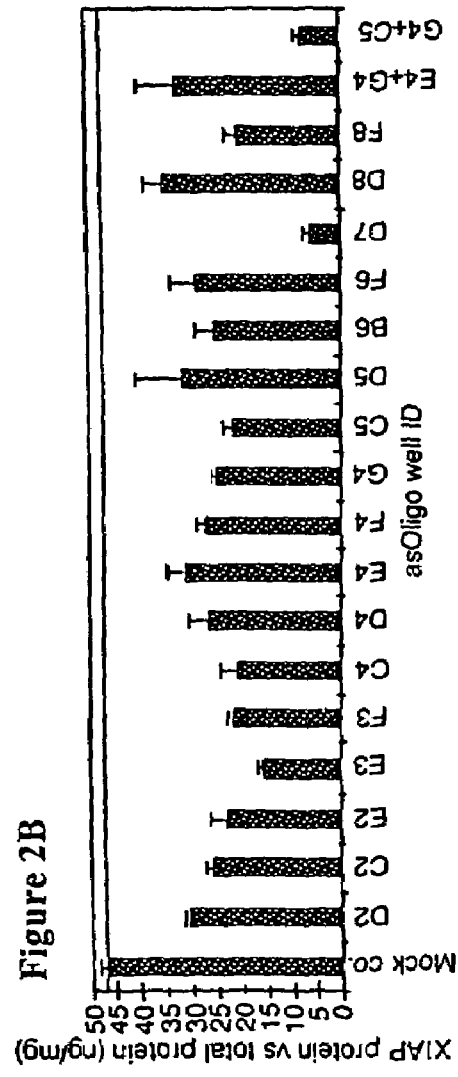

SEQUENCE LISTING

<160> NUMBER OF SEQ ID NOS: 460

<210> SEQ ID NO 1

```
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 5, 6, 8, 12, 16
<223> OTHER INFORMATION: n = T or U

<400> SEQUENCE: 1
aaaanncnaa gnaccngca                                                     19

<210> SEQ ID NO 2
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 3, 10, 14
<223> OTHER INFORMATION: n = T or U

<400> SEQUENCE: 2
ncnagagggn ggcncagga                                                     19

<210> SEQ ID NO 3
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 5, 7, 9, 11, 13, 19
<223> OTHER INFORMATION: n = T or U

<400> SEQUENCE: 3
cagananana ngnaacacn                                                     19

<210> SEQ ID NO 4
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 10, 11, 12, 13, 14, 15, 16, 18, 19
<223> OTHER INFORMATION: n = T or U

<400> SEQUENCE: 4
ngagagcccn nnnnnngnn                                                     19

<210> SEQ ID NO 5
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
```

```
<220> FEATURE:
<221> NAME/KEY: misc_feature
<222> LOCATION: 3, 5, 10, 12, 13, 14, 16, 19
<223> OTHER INFORMATION: n = T or U

<400> SEQUENCE: 5
agnangaaaa annncngan                                              19

<210> SEQ ID NO 6
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 3, 6, 7, 12, 14, 16, 17, 19
<223> OTHER INFORMATION: n = T or U

<400> SEQUENCE: 6
annggnncca angngnncn                                              19

<210> SEQ ID NO 7
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 2, 10, 12, 14, 15, 16, 17
<223> OTHER INFORMATION: n = T or U

<400> SEQUENCE: 7
nnagcaaaan angnnnnaa                                              19

<210> SEQ ID NO 8
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 5, 6, 9, 10, 11, 12, 13, 16, 18
<223> OTHER INFORMATION: n = T or U

<400> SEQUENCE: 8
ngaannaann nnnaananc                                              19

<210> SEQ ID NO 9
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 3, 11, 17, 18
<223> OTHER INFORMATION: n = T or U

<400> SEQUENCE: 9
```
anncaaggca ncaaagnng                                               19

<210> SEQ ID NO 10
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 7, 10, 11, 14, 15
<223> OTHER INFORMATION: n = T or U

<400> SEQUENCE: 10
gncaaancan naannagga                                               19

<210> SEQ ID NO 11
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 5, 7, 12, 14, 17
<223> OTHER INFORMATION: n = T or U

<400> SEQUENCE: 11
aanangnaaa cngngangc                                               19

<210> SEQ ID NO 12
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 7, 13, 16, 19
<223> OTHER INFORMATION: n = T or U

<400> SEQUENCE: 12
gcagaanaaa acnaanaan                                               19

<210> SEQ ID NO 13
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 6, 9, 11, 12, 13
<223> OTHER INFORMATION: n = T or U

<400> SEQUENCE: 13
gaaagnaana nnnaagcag                                               19

<210> SEQ ID NO 14
<211> LENGTH: 19
<212> TYPE: DNA
<213> ORGANISM: Artificial Sequence

```
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 2, 9, 12, 13, 18
<223> OTHER INFORMATION: n = T or U

<400> SEQUENCE: 14
nnaccacanc anncaagnc                                               19

<210> SEQ ID NO 15
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 6, 9, 14, 15
<223> OTHER INFORMATION: n = T or U

<400> SEQUENCE: 15
cnaaanacna gagnncgac                                               19

<210> SEQ ID NO 16
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 11
<223> OTHER INFORMATION: n = T or U

<400> SEQUENCE: 16
acacgaccgc naagaaaca                                               19

<210> SEQ ID NO 17
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 3, 8, 9, 11, 16
<223> OTHER INFORMATION: n = T or U

<400> SEQUENCE: 17
nanccacnna ngacanaaa                                               19

<210> SEQ ID NO 18
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 3, 5, 12, 19
```

```
<223> OTHER INFORMATION: n = T or U

<400> SEQUENCE: 18
gnnanaggag cnaacaaan                                                19

<210> SEQ ID NO 19
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 5
<223> OTHER INFORMATION: n = T or U

<400> SEQUENCE: 19
aangngaaac acaagcaac                                                19

<210> SEQ ID NO 20
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 4, 5, 7, 9, 10, 17
<223> OTHER INFORMATION: n = T or U

<400> SEQUENCE: 20
acannanann aggaaancc                                                19

<210> SEQ ID NO 21
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 3, 5, 11, 12, 13, 14, 16
<223> OTHER INFORMATION: n = T or U

<400> SEQUENCE: 21
cnngnccacc nnnncnaaa                                                19

<210> SEQ ID NO 22
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 4, 5, 7, 9, 10, 16
<223> OTHER INFORMATION: n = T or U

<400> SEQUENCE: 22
ancnncncnn gaaaanagg                                                19
```

<210> SEQ ID NO 23
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 4, 11, 13, 14
<223> OTHER INFORMATION: n = T or U

<400> SEQUENCE: 23
ccnncaaaac ngnnaaaag                                            19

<210> SEQ ID NO 24
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 4, 6, 12
<223> OTHER INFORMATION: n = T or U

<400> SEQUENCE: 24
angncngcag gnacacaag                                            19

<210> SEQ ID NO 25
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 4, 6, 7, 12, 14, 15, 17
<223> OTHER INFORMATION: n = T or U

<400> SEQUENCE: 25
ancnannaaa cnnncnac                                             19

<210> SEQ ID NO 26
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 8, 14, 15
<223> OTHER INFORMATION: n = T or U

<400> SEQUENCE: 26
acaggacnac cacnnggaa                                            19

<210> SEQ ID NO 27
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,

```
         deoxyribonucleotide, or nucleotide analog
<220> FEATURE:
<221> NAME/KEY: misc_feature
<222> LOCATION: 1, 7, 9, 10, 13, 16
<223> OTHER INFORMATION: n = T or U

<400> SEQUENCE: 27
ngccagngnn gangcngaa                                                19

<210> SEQ ID NO 28
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 4, 15, 18
<223> OTHER INFORMATION: n = T or U

<400> SEQUENCE: 28
gnanaaagaa acccngcnc                                                19

<210> SEQ ID NO 29
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 8, 10, 12, 15, 16
<223> OTHER INFORMATION: n = T or U

<400> SEQUENCE: 29
cgcacggnan cnccnncac                                                19

<210> SEQ ID NO 30
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 8, 12, 19
<223> OTHER INFORMATION: n = T or U

<400> SEQUENCE: 30
cnacagcngc angacaacn                                                19

<210> SEQ ID NO 31
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 7, 9, 13, 15, 16
<223> OTHER INFORMATION: n = T or U

<400> SEQUENCE: 31
```

```
gcngagncnc cananngcc                                         19

<210> SEQ ID NO 32
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 5, 6, 7, 10, 12, 14, 16, 17
<223> OTHER INFORMATION: n = T or U

<400> SEQUENCE: 32
anacnnnccn gngncnncc                                         19

<210> SEQ ID NO 33
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 7, 9, 14, 15, 16
<223> OTHER INFORMATION: n = T or U

<400> SEQUENCE: 33
ganaaancng caannnggg                                         19

<210> SEQ ID NO 34
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 2, 4, 9, 13, 19
<223> OTHER INFORMATION: n = T or U

<400> SEQUENCE: 34
nngnagacng cgnggcacn                                         19

<210> SEQ ID NO 35
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 5, 6, 8, 12
<223> OTHER INFORMATION: n = T or U

<400> SEQUENCE: 35
accanncngg anaccagaa                                         19

<210> SEQ ID NO 36
<211> LENGTH: 19
<212> TYPE: DNA
```

<213> ORGANISM: Artificial Sequence
<220> FEATURE:
<223> OTHER INFORMATION: based on Homo sapiens.
     Each nucleobase may be part of a ribonucleotide,
     deoxyribonucleotide, or nucleotide analog
<220> FEATURE:
<221> NAME/KEY: misc_feature
<222> LOCATION: 3, 4, 5, 6, 11, 12, 13, 15, 18
<223> OTHER INFORMATION: n = T or U

<400> SEQUENCE: 36
agnnnncaac nnngnacng                                                    19

<210> SEQ ID NO 37
<211> LENGTH: 19
<212> TYPE: DNA
<213> ORGANISM: Artificial Sequence
<220> FEATURE:
<223> OTHER INFORMATION: based on Homo sapiens.
     Each nucleobase may be part of a ribonucleotide,
     deoxyribonucleotide, or nucleotide analog
<220> FEATURE:
<221> NAME/KEY: misc_feature
<222> LOCATION: 2, 5, 7, 9, 12, 13
<223> OTHER INFORMATION: n = T or U

<400> SEQUENCE: 37
angancncng cnncccaga                                                    19

<210> SEQ ID NO 38
<211> LENGTH: 19
<212> TYPE: DNA
<213> ORGANISM: Artificial Sequence
<220> FEATURE:
<223> OTHER INFORMATION: based on Homo sapiens.
     Each nucleobase may be part of a ribonucleotide,
     deoxyribonucleotide, or nucleotide analog
<220> FEATURE:
<221> NAME/KEY: misc_feature
<222> LOCATION: 4, 9, 11, 13
<223> OTHER INFORMATION: n = T or U

<400> SEQUENCE: 38
aganggccng ncnaaggca                                                    19

<210> SEQ ID NO 39
<211> LENGTH: 19
<212> TYPE: DNA
<213> ORGANISM: Artificial Sequence
<220> FEATURE:
<223> OTHER INFORMATION: based on Homo sapiens.
     Each nucleobase may be part of a ribonucleotide,
     deoxyribonucleotide, or nucleotide analog
<220> FEATURE:
<221> NAME/KEY: misc_feature
<222> LOCATION: 3, 4, 6, 14, 17, 19
<223> OTHER INFORMATION: n = T or U

<400> SEQUENCE: 39
agnncncaaa aganagncn                                                    19

<210> SEQ ID NO 40
<211> LENGTH: 19
<212> TYPE: DNA
<213> ORGANISM: Artificial Sequence
<220> FEATURE:
<223> OTHER INFORMATION: based on Homo sapiens.
     Each nucleobase may be part of a ribonucleotide,
     deoxyribonucleotide, or nucleotide analog
<220> FEATURE:
<221> NAME/KEY: misc_feature

```
<222> LOCATION: 2, 4, 6, 9, 11, 13, 15
<223> OTHER INFORMATION: n = T or U

<400> SEQUENCE: 40
gngncngana nancnacaa                                              19

<210> SEQ ID NO 41
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 6, 8, 10, 13, 15, 17
<223> OTHER INFORMATION: n = T or U

<400> SEQUENCE: 41
ncgggnanan ggngncnga                                              19

<210> SEQ ID NO 42
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 6, 7, 10, 15, 17, 19
<223> OTHER INFORMATION: n = T or U

<400> SEQUENCE: 42
cagggnnccn cgggnanan                                              19

<210> SEQ ID NO 43
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 4, 6, 7, 13, 17
<223> OTHER INFORMATION: n = T or U

<400> SEQUENCE: 43
gcnncnncac aanacangg                                              19

<210> SEQ ID NO 44
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 7, 8, 10, 19
<223> OTHER INFORMATION: n = T or U

<400> SEQUENCE: 44
ggccagnncn gaaaggacn                                              19
```

<210> SEQ ID NO 45
<211> LENGTH: 19
<212> TYPE: DNA
<213> ORGANISM: Artificial Sequence
<220> FEATURE:
<223> OTHER INFORMATION: based on Homo sapiens.
    Each nucleobase may be part of a ribonucleotide,
    deoxyribonucleotide, or nucleotide analog
<220> FEATURE:
<221> NAME/KEY: misc_feature
<222> LOCATION: 3, 7, 9, 11, 12, 17, 18
<223> OTHER INFORMATION: n = T or U

<400> SEQUENCE: 45
gcnaacncnc nngggnna                                                19

<210> SEQ ID NO 46
<211> LENGTH: 19
<212> TYPE: DNA
<213> ORGANISM: Artificial Sequence
<220> FEATURE:
<223> OTHER INFORMATION: based on Homo sapiens.
    Each nucleobase may be part of a ribonucleotide,
    deoxyribonucleotide, or nucleotide analog
<220> FEATURE:
<221> NAME/KEY: misc_feature
<222> LOCATION: 2, 4, 7, 12
<223> OTHER INFORMATION: n = T or U

<400> SEQUENCE: 46
gngnagnaga gnccagcac                                               19

<210> SEQ ID NO 47
<211> LENGTH: 19
<212> TYPE: DNA
<213> ORGANISM: Artificial Sequence
<220> FEATURE:
<223> OTHER INFORMATION: based on Homo sapiens.
    Each nucleobase may be part of a ribonucleotide,
    deoxyribonucleotide, or nucleotide analog
<220> FEATURE:
<221> NAME/KEY: misc_feature
<222> LOCATION: 7, 12, 13, 16
<223> OTHER INFORMATION: n = T or U

<400> SEQUENCE: 47
aagcacngca cnnggncac                                               19

<210> SEQ ID NO 48
<211> LENGTH: 19
<212> TYPE: DNA
<213> ORGANISM: Artificial Sequence
<220> FEATURE:
<223> OTHER INFORMATION: based on Homo sapiens.
    Each nucleobase may be part of a ribonucleotide,
    deoxyribonucleotide, or nucleotide analog
<220> FEATURE:
<221> NAME/KEY: misc_feature
<222> LOCATION: 1, 2, 6, 7, 8, 9
<223> OTHER INFORMATION: n = T or U

<400> SEQUENCE: 48
nncagnnnnc caccacaac                                               19

<210> SEQ ID NO 49
<211> LENGTH: 19
<212> TYPE: DNA
<213> ORGANISM: Artificial Sequence
<220> FEATURE:
<223> OTHER INFORMATION: based on Homo sapiens.

```
        Each nucleobase may be part of a ribonucleotide,
        deoxyribonucleotide, or nucleotide analog
<220> FEATURE:
<221> NAME/KEY: misc_feature
<222> LOCATION: 5, 13, 14
<223> OTHER INFORMATION: n = T or U

<400> SEQUENCE: 49
acgancacaa ggnncccaa                                               19

<210> SEQ ID NO 50
<211> LENGTH: 19
<212> TYPE: DNA
<213> ORGANISM: Artificial Sequence
<220> FEATURE:
<223> OTHER INFORMATION: based on Homo sapiens.
        Each nucleobase may be part of a ribonucleotide,
        deoxyribonucleotide, or nucleotide analog
<220> FEATURE:
<221> NAME/KEY: misc_feature
<222> LOCATION: 1, 6, 8, 10, 11, 13
<223> OTHER INFORMATION: n = T or U

<400> SEQUENCE: 50
ncgccngngn ncngaccag                                               19

<210> SEQ ID NO 51
<211> LENGTH: 19
<212> TYPE: DNA
<213> ORGANISM: Artificial Sequence
<220> FEATURE:
<223> OTHER INFORMATION: based on Homo sapiens.
        Each nucleobase may be part of a ribonucleotide,
        deoxyribonucleotide, or nucleotide analog

<400> SEQUENCE: 51
ccggcccaaa acaaagaag                                               19

<210> SEQ ID NO 52
<211> LENGTH: 19
<212> TYPE: DNA
<213> ORGANISM: Artificial Sequence
<220> FEATURE:
<223> OTHER INFORMATION: based on Homo sapiens.
        Each nucleobase may be part of a ribonucleotide,
        deoxyribonucleotide, or nucleotide analog
<220> FEATURE:
<221> NAME/KEY: misc_feature
<222> LOCATION: 3, 4, 8, 9, 14, 16, 17
<223> OTHER INFORMATION: n = T or U

<400> SEQUENCE: 52
ganncacnnc gaanannaa                                               19

<210> SEQ ID NO 53
<211> LENGTH: 19
<212> TYPE: DNA
<213> ORGANISM: Artificial Sequence
<220> FEATURE:
<223> OTHER INFORMATION: based on Homo sapiens.
        Each nucleobase may be part of a ribonucleotide,
        deoxyribonucleotide, or nucleotide analog
<220> FEATURE:
<221> NAME/KEY: misc_feature
<222> LOCATION: 1, 3, 10, 18
<223> OTHER INFORMATION: n = T or U

<400> SEQUENCE: 53
nancagaacn cacagcanc                                               19
```

<210> SEQ ID NO 54
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 7, 8, 9, 11, 12, 16, 17, 18
<223> OTHER INFORMATION: n = T or U

<400> SEQUENCE: 54
ggaagannng nngaannng                                              19

<210> SEQ ID NO 55
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 3, 8, 12, 16, 17, 18
<223> OTHER INFORMATION: n = T or U

<400> SEQUENCE: 55
ncngccangg anggannnc                                              19

<210> SEQ ID NO 56
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 4, 10, 14, 17, 18
<223> OTHER INFORMATION: n = T or U

<400> SEQUENCE: 56
aagnaaagan ccgngcnnc                                              19

<210> SEQ ID NO 57
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 6, 8, 10, 14, 16
<223> OTHER INFORMATION: n = T or U

<400> SEQUENCE: 57
cngagnanan ccangnccc                                              19

<210> SEQ ID NO 58
<211> LENGTH: 19
<212> TYPE: DNA
<213> ORGANISM: Artificial Sequence
<220> FEATURE:
<223> OTHER INFORMATION: based on Homo sapiens.

Each nucleobase may be part of a ribonucleotide,
deoxyribonucleotide, or nucleotide analog
<220> FEATURE:
<221> NAME/KEY: misc_feature
<222> LOCATION: 7, 10, 13, 14, 16, 17
<223> OTHER INFORMATION: n = T or U

<400> SEQUENCE: 58
gcaagcngcn ccnngnnaa                                                    19

<210> SEQ ID NO 59
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 7, 12, 18
<223> OTHER INFORMATION: n = T or U

<400> SEQUENCE: 59
aaagcanaaa anccagcnc                                                    19

<210> SEQ ID NO 60
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 9, 10, 11, 14, 15, 16, 18
<223> OTHER INFORMATION: n = T or U

<400> SEQUENCE: 60
gaaagcacnn nacnnnanc                                                    19

<210> SEQ ID NO 61
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 8, 9, 14, 18, 19
<223> OTHER INFORMATION: n = T or U

<400> SEQUENCE: 61
acngggcnnc caancagnn                                                    19

<210> SEQ ID NO 62
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 3, 5, 6, 15, 17, 18
<223> OTHER INFORMATION: n = T or U

<400> SEQUENCE: 62
gnngnnccca agggncnnc                                              19

<210> SEQ ID NO 63
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 5, 9, 14, 15, 16
<223> OTHER INFORMATION: n = T or U

<400> SEQUENCE: 63
acccnggana ccannnagc                                              19

<210> SEQ ID NO 64
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 3, 4, 6, 13, 15, 16, 17
<223> OTHER INFORMATION: n = T or U

<400> SEQUENCE: 64
ngnncnaaca ganannngc                                              19

<210> SEQ ID NO 65
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 3, 5, 7, 8, 10, 11, 13, 17, 18
<223> OTHER INFORMATION: n = T or U

<400> SEQUENCE: 65
nananannCn ngncccnnc                                              19

<210> SEQ ID NO 66
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 4, 8, 12, 14, 15, 17, 18, 19
<223> OTHER INFORMATION: n = T or U

<400> SEQUENCE: 66
agnnaaanga ananngnnn                                              19

<210> SEQ ID NO 67
<211> LENGTH: 19

```
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 6, 9, 14, 18
<223> OTHER INFORMATION: n = T or U

<400> SEQUENCE: 67
gacacnccnc aagngaang                                              19

<210> SEQ ID NO 68
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 2, 3, 5, 9, 12, 13, 15, 16
<223> OTHER INFORMATION: n = T or U

<400> SEQUENCE: 68
nnncncagna gnncnnacc                                              19

<210> SEQ ID NO 69
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 3, 6, 9, 12, 14, 15, 16, 17, 19
<223> OTHER INFORMATION: n = T or U

<400> SEQUENCE: 69
gnnagngang gngnnnncn                                              19

<210> SEQ ID NO 70
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 4, 7, 9, 12, 16, 17, 19
<223> OTHER INFORMATION: n = T or U

<400> SEQUENCE: 70
aganggnanc ancaanncn                                              19

<210> SEQ ID NO 71
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
```

```
<221> NAME/KEY: misc_feature
<222> LOCATION: 1, 3, 8, 13, 14, 15, 16
<223> OTHER INFORMATION: n = T or U

<400> SEQUENCE: 71
ngnaccanag gannnngga                                                19

<210> SEQ ID NO 72
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 6, 7, 10, 12, 16, 17, 19
<223> OTHER INFORMATION: n = T or U

<400> SEQUENCE: 72
ccccanncgn anagcnncn                                                19

<210> SEQ ID NO 73
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 3, 5, 6, 7, 8, 10, 11, 14, 16, 19
<223> OTHER INFORMATION: n = T or U

<400> SEQUENCE: 73
annannnncn naangnccn                                                19

<210> SEQ ID NO 74
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 5, 8, 9, 10, 12, 15, 16, 19
<223> OTHER INFORMATION: n = T or U

<400> SEQUENCE: 74
caagngannn anagnngcn                                                19

<210> SEQ ID NO 75
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 5, 7
<223> OTHER INFORMATION: n = T or U

<400> SEQUENCE: 75
nagancngca accagaacc                                                19
```

```
<210> SEQ ID NO 76
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 5, 6, 10, 13, 15, 17, 18, 19
<223> OTHER INFORMATION: n = T or U

<400> SEQUENCE: 76
cancnngcan acngncnnn                                               19

<210> SEQ ID NO 77
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 4, 8, 11, 13, 14, 18
<223> OTHER INFORMATION: n = T or U

<400> SEQUENCE: 77
ccnnagcngc ncnncagna                                               19

<210> SEQ ID NO 78
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 5, 6, 8, 11, 13, 14
<223> OTHER INFORMATION: n = T or U

<400> SEQUENCE: 78
aagcnncncc ncnngcagg                                               19

<210> SEQ ID NO 79
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 4, 5, 6, 8, 10, 14
<223> OTHER INFORMATION: n = T or U

<400> SEQUENCE: 79
anannncnan ccanacaga                                               19

<210> SEQ ID NO 80
<211> LENGTH: 19
<212> TYPE: DNA
<213> ORGANISM: Artificial Sequence
<220> FEATURE:
```

```
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 6, 8
<223> OTHER INFORMATION: n = T or U

<400> SEQUENCE: 80
cnagangncc acaaggaac                                                19

<210> SEQ ID NO 81
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 7, 8, 10, 11, 12, 18
<223> OTHER INFORMATION: n = T or U

<400> SEQUENCE: 81
agcacanngn nnacaagng                                                19

<210> SEQ ID NO 82
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 7, 15, 16, 18
<223> OTHER INFORMATION: n = T or U

<400> SEQUENCE: 82
agcacanggg acacnngnc                                                19

<210> SEQ ID NO 83
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 3, 9, 12, 16, 18
<223> OTHER INFORMATION: n = T or U

<400> SEQUENCE: 83
cnngaaagna angacngng                                                19

<210> SEQ ID NO 84
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 6, 8, 13, 14, 18, 19
<223> OTHER INFORMATION: n = T or U
```

```
<400> SEQUENCE: 84
ccnacnanag agnnagann                                                19

<210> SEQ ID NO 85
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 3, 7, 13, 16
<223> OTHER INFORMATION: n = T or U

<400> SEQUENCE: 85
anncaancag ggnaanaag                                                19

<210> SEQ ID NO 86
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 4, 8, 9, 14
<223> OTHER INFORMATION: n = T or U

<400> SEQUENCE: 86
aagncagnnc acancacac                                                19

<210> SEQ ID NO 87
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 4, 13, 17
<223> OTHER INFORMATION: n = T or U

<400> SEQUENCE: 87
cagnaaaaaa aangganaa                                                19

<210> SEQ ID NO 88
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 2, 6, 7, 9, 12, 14, 17
<223> OTHER INFORMATION: n = T or U

<400> SEQUENCE: 88
nncagnnana gnangangc                                                19

<210> SEQ ID NO 89
```

```
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 6, 7, 13, 14, 18
<223> OTHER INFORMATION: n = T or U

<400> SEQUENCE: 89
nacacnnaga aannaaanc                                                19

<210> SEQ ID NO 90
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 3, 5, 7, 9, 10, 11
<223> OTHER INFORMATION: n = T or U

<400> SEQUENCE: 90
ncncnancnn nccaccagc                                                19

<210> SEQ ID NO 91
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 5, 8
<223> OTHER INFORMATION: n = T or U

<400> SEQUENCE: 91
agaanccnaa aacacaaca                                                19

<210> SEQ ID NO 92
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 3, 12, 16, 18, 19
<223> OTHER INFORMATION: n = T or U

<400> SEQUENCE: 92
anncgcacaa gnacgngnn                                                19

<210> SEQ ID NO 93
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
```

```
<220> FEATURE:
<221> NAME/KEY: misc_feature
<222> LOCATION: 1, 3, 7, 11, 13, 14, 18
<223> OTHER INFORMATION: n = T or U

<400> SEQUENCE: 93
ngncagnaca ngnnggcnc                                                    19

<210> SEQ ID NO 94
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 4, 7, 9, 10, 11, 12, 18, 19
<223> OTHER INFORMATION: n = T or U

<400> SEQUENCE: 94
acanagngnn nngccacnn                                                    19

<210> SEQ ID NO 95
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 3, 4, 7, 9, 13, 19
<223> OTHER INFORMATION: n = T or U

<400> SEQUENCE: 95
cnnngancng gcncagacn                                                    19

<210> SEQ ID NO 96
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 10, 11, 12, 18, 19
<223> OTHER INFORMATION: n = T or U

<400> SEQUENCE: 96
gaaaccacan nnaacagnn                                                    19

<210> SEQ ID NO 97
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 5, 7, 10, 11, 18
<223> OTHER INFORMATION: n = T or U

<400> SEQUENCE: 97
```
ggnancnccn ncaccagna                                                19

<210> SEQ ID NO 98
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 9, 10, 13, 15, 17
<223> OTHER INFORMATION: n = T or U

<400> SEQUENCE: 98
angaccacnn ccncnangg                                                19

<210> SEQ ID NO 99
<211> LENGTH: 15
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 11, 12, 13, 15
<223> OTHER INFORMATION: n = T or U

<400> SEQUENCE: 99
ganaccagaa nnngn                                                    15

<210> SEQ ID NO 100
<211> LENGTH: 15
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 3, 4, 5, 13
<223> OTHER INFORMATION: n = T or U

<400> SEQUENCE: 100
ngnnnaagac canag                                                    15

<210> SEQ ID NO 101
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 7, 9, 13, 16
<223> OTHER INFORMATION: n = T or U

<400> SEQUENCE: 101
gcngagncnc canacngcc                                                19

<210> SEQ ID NO 102
<211> LENGTH: 19
<212> TYPE: DNA
<213> ORGANISM: Artificial Sequence

```
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 4, 6, 8, 15, 19
<223> OTHER INFORMATION: n = T or U

<400> SEQUENCE: 102
ggcncncngc ccacngaan                                              19

<210> SEQ ID NO 103
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 4, 5, 7, 9, 10, 16
<223> OTHER INFORMATION: n = T or U

<400> SEQUENCE: 103
ancnncncnn gaaaanagg                                              19

<210> SEQ ID NO 104
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 7, 8, 9, 12, 13, 14, 19
<223> OTHER INFORMATION: n = T or U

<400> SEQUENCE: 104
cagagannnc annnaacgn                                              19

<210> SEQ ID NO 105
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 4, 5, 9, 10, 13, 14, 16
<223> OTHER INFORMATION: n = T or U

<400> SEQUENCE: 105
ancnngacnn gannanagg                                              19

<210> SEQ ID NO 106
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 4, 10, 11, 13, 15, 16, 18
```

```
<223> OTHER INFORMATION: n = T or U

<400> SEQUENCE: 106
gganaaaagn ncncnncna                                                19

<210> SEQ ID NO 107
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 8, 10, 12, 15, 16
<223> OTHER INFORMATION: n = T or U

<400> SEQUENCE: 107
cgcacggnan cnccnncac                                                19

<210> SEQ ID NO 108
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 7, 13, 16, 17
<223> OTHER INFORMATION: n = T or U

<400> SEQUENCE: 108
cnacgcncgc cancgnnca                                                19

<210> SEQ ID NO 109
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 4, 5, 8, 10, 12
<223> OTHER INFORMATION: n = T or U

<400> SEQUENCE: 109
cacnnccncn anggcacgc                                                19

<210> SEQ ID NO 110
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 8, 10, 12, 15, 16
<223> OTHER INFORMATION: n = T or U

<400> SEQUENCE: 110
cgcacccnan cnggnncac                                                19
```

```
<210> SEQ ID NO 111
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 7, 9, 13, 15, 16
<223> OTHER INFORMATION: n = T or U

<400> SEQUENCE: 111
gcngagncnc cananngcc                                               19

<210> SEQ ID NO 112
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 4, 6, 7, 8, 15, 19
<223> OTHER INFORMATION: n = T or U

<400> SEQUENCE: 112
ggcncnnncg ccacngaan                                               19

<210> SEQ ID NO 113
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 4, 5, 7, 11, 13, 17
<223> OTHER INFORMATION: n = T or U

<400> SEQUENCE: 113
ccgnnanacc ncngagncg                                               19

<210> SEQ ID NO 114
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 9, 14, 15, 16
<223> OTHER INFORMATION: n = T or U

<400> SEQUENCE: 114
gcngacacnc caannngcc                                               19

<210> SEQ ID NO 115
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
``` deoxyribonucleotide, or nucleotide analog
<220> FEATURE:
<221> NAME/KEY: misc_feature
<222> LOCATION: 5, 6, 8, 11
<223> OTHER INFORMATION: n = T or U

<400> SEQUENCE: 115
accanncngg naaccagaa                                                    19

<210> SEQ ID NO 116
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 11, 14, 17
<223> OTHER INFORMATION: n = T or U

<400> SEQUENCE: 116
ngcccaagaa nacnagnca                                                    19

<210> SEQ ID NO 117
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 5, 8, 12, 13
<223> OTHER INFORMATION: n = T or U

<400> SEQUENCE: 117
accanagngg anngcagaa                                                    19

<210> SEQ ID NO 118
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 8, 12, 14, 15
<223> OTHER INFORMATION: n = T or U

<400> SEQUENCE: 118
aagaccanag gncnnacca                                                    19

<210> SEQ ID NO 119
<211> LENGTH: 22
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 4, 8, 9, 11, 12, 17, 19, 20
<223> OTHER INFORMATION: n = T or U

<400> SEQUENCE: 119

```
ganncacnnc nncgaanann aa                                              22

<210> SEQ ID NO 120
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 6, 8, 12, 15, 17, 18
<223> OTHER INFORMATION: n = T or U

<400> SEQUENCE: 120
ngaaangnaa ancancnnc                                                  19

<210> SEQ ID NO 121
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 4, 6, 8, 9, 13, 16, 17
<223> OTHER INFORMATION: n = T or U

<400> SEQUENCE: 121
ganncngnnc ganaannaa                                                  19

<210> SEQ ID NO 122
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 4, 6, 11, 12, 16, 17
<223> OTHER INFORMATION: n = T or U

<400> SEQUENCE: 122
aannanaagc nncacnnag                                                  19

<210> SEQ ID NO 123
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 7, 9, 13, 15, 16
<223> OTHER INFORMATION: n = T or U

<400> SEQUENCE: 123
gcngagncnc cananngcc                                                  19

<210> SEQ ID NO 124
<211> LENGTH: 19
<212> TYPE: DNA
```

```
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 4, 6, 7, 8, 15, 19
<223> OTHER INFORMATION: n = T or U

<400> SEQUENCE: 124
ggcncnnngc ccacngaan                                               19

<210> SEQ ID NO 125
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 5, 6, 8, 12
<223> OTHER INFORMATION: n = T or U

<400> SEQUENCE: 125
accanncngg anaccagaa                                               19

<210> SEQ ID NO 126
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 8, 12, 14, 15
<223> OTHER INFORMATION: n = T or U

<400> SEQUENCE: 126
aagaccanag gncnnacca                                               19

<210> SEQ ID NO 127
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 4, 5, 7, 9, 10, 16
<223> OTHER INFORMATION: n = T or U

<400> SEQUENCE: 127
ancnncncnn gaaaanagg                                               19

<210> SEQ ID NO 128
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
```

```
<222> LOCATION: 4, 10, 11, 13, 15, 16, 18
<223> OTHER INFORMATION: n = T or U

<400> SEQUENCE: 128
gganaaaagn ncncnncna                                                19

<210> SEQ ID NO 129
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 5, 7, 10, 11, 18
<223> OTHER INFORMATION: n = T or U

<400> SEQUENCE: 129
ggnancnccn ncaccagna                                                19

<210> SEQ ID NO 130
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 9, 10, 13, 15, 17
<223> OTHER INFORMATION: n = T or U

<400> SEQUENCE: 130
angaccacnn ccncnangg                                                19

<210> SEQ ID NO 131
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 3, 7, 15, 16, 17, 19
<223> OTHER INFORMATION: n = T or U

<400> SEQUENCE: 131
ncngganacc agaannngn                                                19

<210> SEQ ID NO 132
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 3, 4, 5, 13, 17, 19
<223> OTHER INFORMATION: n = T or U

<400> SEQUENCE: 132
ngnnnaagac canaggncn                                                19
```

<210> SEQ ID NO 133
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 4, 5, 8, 13, 15, 17
<223> OTHER INFORMATION: n = T or U

<400> SEQUENCE: 133
gggnnccncg ggnanangg                                                19

<210> SEQ ID NO 134
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 5, 7, 12, 15, 16
<223> OTHER INFORMATION: n = T or U

<400> SEQUENCE: 134
ggnananggc gnccnnggg                                                19

<210> SEQ ID NO 135
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 4, 8, 9, 14, 16, 17
<223> OTHER INFORMATION: n = T or U

<400> SEQUENCE: 135
ganncacnnc gaanannaa                                                19

<210> SEQ ID NO 136
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 4, 6, 11, 12, 16, 17
<223> OTHER INFORMATION: n = T or U

<400> SEQUENCE: 136
aannanaacg nncacnnag                                                19

<210> SEQ ID NO 137
<211> LENGTH: 19
<212> TYPE: DNA
<213> ORGANISM: Artificial Sequence
<220> FEATURE:
<223> OTHER INFORMATION: based on Homo sapiens.

```
      Each nucleobase may be part of a ribonucleotide,
      deoxyribonucleotide, or nucleotide analog
<220> FEATURE:
<221> NAME/KEY: misc_feature
<222> LOCATION: 2, 4, 5, 7, 9, 10, 16
<223> OTHER INFORMATION: n = T or U

<400> SEQUENCE: 137
ancnncncnn gaaaanagg                                              19

<210> SEQ ID NO 138
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 7, 9, 13, 15, 16
<223> OTHER INFORMATION: n = T or U

<400> SEQUENCE: 138
gcngagncnc cananngcc                                              19

<210> SEQ ID NO 139
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 4, 8, 9, 14, 16, 17
<223> OTHER INFORMATION: n = T or U

<400> SEQUENCE: 139
ganncacnnc gaanannaa                                              19

<210> SEQ ID NO 140
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 11, 14, 17
<223> OTHER INFORMATION: n = T or U

<400> SEQUENCE: 140
ngcccaagaa nacnagnca                                              19

<210> SEQ ID NO 141
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 7, 9, 13, 15, 16
<223> OTHER INFORMATION: n = T or U
```

<400> SEQUENCE: 141
gcngagncnc cananngcc                                              19

<210> SEQ ID NO 142
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 4, 6, 7, 8, 15, 19
<223> OTHER INFORMATION: n = T or U

<400> SEQUENCE: 142
ggcncnnngc ccacngaan                                              19

<210> SEQ ID NO 143
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 5, 7, 10, 11, 18
<223> OTHER INFORMATION: n = T or U

<400> SEQUENCE: 143
ggnancnccn ncaccagna                                              19

<210> SEQ ID NO 144
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 9, 10, 13, 15, 17
<223> OTHER INFORMATION: n = T or U

<400> SEQUENCE: 144
angaccacnn ccncnangg                                              19

<210> SEQ ID NO 145
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 6, 9, 11, 12, 13
<223> OTHER INFORMATION: n = T or U

<400> SEQUENCE: 145
gaaagnaana nnnaagcag                                              19

<210> SEQ ID NO 146
<211> LENGTH: 19

```
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 7, 8, 9, 11, 14
<223> OTHER INFORMATION: n = T or U

<400> SEQUENCE: 146
gagcaannna naangaaag                                              19

<210> SEQ ID NO 147
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 6, 15, 16, 18
<223> OTHER INFORMATION: n = T or U

<400> SEQUENCE: 147
accgcnaaga aacanncna                                              19

<210> SEQ ID NO 148
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 4, 5, 14
<223> OTHER INFORMATION: n = T or U

<400> SEQUENCE: 148
ancnnacaaa gaanccgca                                              19

<210> SEQ ID NO 149
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 3, 8, 9, 11, 16
<223> OTHER INFORMATION: n = T or U

<400> SEQUENCE: 149
nanccacnna ngacanaaa                                              19

<210> SEQ ID NO 150
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
```

```
<221> NAME/KEY: misc_feature
<222> LOCATION: 4, 9, 11, 12, 17, 19
<223> OTHER INFORMATION: n = T or U

<400> SEQUENCE: 150
aaanacagna nncaccnan                                                    19

<210> SEQ ID NO 151
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 8, 12, 17, 18, 19
<223> OTHER INFORMATION: n = T or U

<400> SEQUENCE: 151
ngcacccngg anaccannn                                                    19

<210> SEQ ID NO 152
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 2, 3, 8, 12, 19
<223> OTHER INFORMATION: n = T or U

<400> SEQUENCE: 152
nnnaccanag gncccagcn                                                    19

<210> SEQ ID NO 153
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 7, 9, 13, 16
<223> OTHER INFORMATION: n = T or U

<400> SEQUENCE: 153
gcngagncnc canacngcc                                                    19

<210> SEQ ID NO 154
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 4, 6, 8, 15, 19
<223> OTHER INFORMATION: n = T or U

<400> SEQUENCE: 154
ggcncncngc ccacngaan                                                    19
```

<210> SEQ ID NO 155
<211> LENGTH: 19
<212> TYPE: DNA
<213> ORGANISM: Artificial Sequence
<220> FEATURE:
<223> OTHER INFORMATION: based on Homo sapiens.
    Each nucleobase may be part of a ribonucleotide,
    deoxyribonucleotide, or nucleotide analog
<220> FEATURE:
<221> NAME/KEY: misc_feature
<222> LOCATION: 2, 3, 6, 7, 12, 14, 16, 17, 19
<223> OTHER INFORMATION: n = T or U

<400> SEQUENCE: 155
annggnncca angngnncn                                           19

<210> SEQ ID NO 156
<211> LENGTH: 19
<212> TYPE: DNA
<213> ORGANISM: Artificial Sequence
<220> FEATURE:
<223> OTHER INFORMATION: based on Homo sapiens.
    Each nucleobase may be part of a ribonucleotide,
    deoxyribonucleotide, or nucleotide analog
<220> FEATURE:
<221> NAME/KEY: misc_feature
<222> LOCATION: 1, 3, 4, 6, 8, 13, 14, 17, 18
<223> OTHER INFORMATION: n = T or U

<400> SEQUENCE: 156
ncnngngnaa ccnnggnna                                           19

<210> SEQ ID NO 157
<211> LENGTH: 19
<212> TYPE: DNA
<213> ORGANISM: Artificial Sequence
<220> FEATURE:
<223> OTHER INFORMATION: based on Homo sapiens.
    Each nucleobase may be part of a ribonucleotide,
    deoxyribonucleotide, or nucleotide analog
<220> FEATURE:
<221> NAME/KEY: misc_feature
<222> LOCATION: 8, 14, 15
<223> OTHER INFORMATION: n = T or U

<400> SEQUENCE: 157
acaggacnac cacnnggaa                                           19

<210> SEQ ID NO 158
<211> LENGTH: 19
<212> TYPE: DNA
<213> ORGANISM: Artificial Sequence
<220> FEATURE:
<223> OTHER INFORMATION: based on Homo sapiens.
    Each nucleobase may be part of a ribonucleotide,
    deoxyribonucleotide, or nucleotide analog
<220> FEATURE:
<221> NAME/KEY: misc_feature
<222> LOCATION: 5, 6, 12
<223> OTHER INFORMATION: n = T or U

<400> SEQUENCE: 158
aaggnncacc ancaggaca                                           19

<210> SEQ ID NO 159
<211> LENGTH: 19
<212> TYPE: DNA
<213> ORGANISM: Artificial Sequence
<220> FEATURE:

<223> OTHER INFORMATION: based on Homo sapiens.
    Each nucleobase may be part of a ribonucleotide,
    deoxyribonucleotide, or nucleotide analog
<220> FEATURE:
<221> NAME/KEY: misc_feature
<222> LOCATION: 7, 12, 13, 16
<223> OTHER INFORMATION: n = T or U

<400> SEQUENCE: 159
aagcacngca cnnggncac                                               19

<210> SEQ ID NO 160
<211> LENGTH: 19
<212> TYPE: DNA
<213> ORGANISM: Artificial Sequence
<220> FEATURE:
<223> OTHER INFORMATION: based on Homo sapiens.
    Each nucleobase may be part of a ribonucleotide,
    deoxyribonucleotide, or nucleotide analog
<220> FEATURE:
<221> NAME/KEY: misc_feature
<222> LOCATION: 4, 7, 8, 13
<223> OTHER INFORMATION: n = T or U

<400> SEQUENCE: 160
cacnggnnga ccncacaag                                               19

<210> SEQ ID NO 161
<211> LENGTH: 19
<212> TYPE: DNA
<213> ORGANISM: Artificial Sequence
<220> FEATURE:
<223> OTHER INFORMATION: based on Homo sapiens.
    Each nucleobase may be part of a ribonucleotide,
    deoxyribonucleotide, or nucleotide analog
<220> FEATURE:
<221> NAME/KEY: misc_feature
<222> LOCATION: 1, 3, 7, 11, 13, 14, 18
<223> OTHER INFORMATION: n = T or U

<400> SEQUENCE: 161
ngncagnaca ngnnggcnc                                               19

<210> SEQ ID NO 162
<211> LENGTH: 19
<212> TYPE: DNA
<213> ORGANISM: Artificial Sequence
<220> FEATURE:
<223> OTHER INFORMATION: based on Homo sapiens.
    Each nucleobase may be part of a ribonucleotide,
    deoxyribonucleotide, or nucleotide analog
<220> FEATURE:
<221> NAME/KEY: misc_feature
<222> LOCATION: 2, 6, 7, 9, 13, 17, 19
<223> OTHER INFORMATION: n = T or U

<400> SEQUENCE: 162
cnaggnngnc cangacngn                                               19

<210> SEQ ID NO 163
<211> LENGTH: 19
<212> TYPE: DNA
<213> ORGANISM: Artificial Sequence
<220> FEATURE:
<223> OTHER INFORMATION: based on Homo sapiens.
    Each nucleobase may be part of a ribonucleotide,
    deoxyribonucleotide, or nucleotide analog
<220> FEATURE:
<221> NAME/KEY: misc_feature
<222> LOCATION: 1, 4, 5, 6, 12, 19
<223> OTHER INFORMATION: n = T or U

<400> SEQUENCE: 163
ncannngagc cnggggaggn                                                      19

<210> SEQ ID NO 164
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 8
<223> OTHER INFORMATION: n = T or U

<400> SEQUENCE: 164
cggaggcnga ggcaggaga                                                       19

<210> SEQ ID NO 165
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 5, 8, 11, 19
<223> OTHER INFORMATION: n = T or U

<400> SEQUENCE: 165
ggngnggngg nacgcgccn                                                       19

<210> SEQ ID NO 166
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 6, 16
<223> OTHER INFORMATION: n = T or U

<400> SEQUENCE: 166
acccangcac aaaacnacc                                                       19

<210> SEQ ID NO 167
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 5, 7, 13
<223> OTHER INFORMATION: n = T or U

<400> SEQUENCE: 167
agaangngcc agnaggaga                                                       19

<210> SEQ ID NO 168

```
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 3, 12, 13, 18, 19
<223> OTHER INFORMATION: n = T or U

<400> SEQUENCE: 168
ncncacagac gnngggcnn                                            19

<210> SEQ ID NO 169
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 5, 8, 9, 10, 18
<223> OTHER INFORMATION: n = T or U

<400> SEQUENCE: 169
ccagnggnnn gcaagcang                                            19

<210> SEQ ID NO 170
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 5, 6, 7, 10
<223> OTHER INFORMATION: n = T or U

<400> SEQUENCE: 170
gaaannnagn ggccaggaa                                            19

<210> SEQ ID NO 171
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 6, 13, 14
<223> OTHER INFORMATION: n = T or U

<400> SEQUENCE: 171
agaaanacac aanngcacc                                            19

<210> SEQ ID NO 172
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
```

```
<220> FEATURE:
<221> NAME/KEY: misc_feature
<222> LOCATION: 1, 4, 7, 11, 12, 13, 14
<223> OTHER INFORMATION: n = T or U

<400> SEQUENCE: 172
nacnganaca nnnnaagga                                                  19

<210> SEQ ID NO 173
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 2, 8, 14, 15, 17
<223> OTHER INFORMATION: n = T or U

<400> SEQUENCE: 173
nncaacangg aganncnaa                                                  19

<210> SEQ ID NO 174
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 3, 4, 6, 8, 12, 13, 14, 19
<223> OTHER INFORMATION: n = T or U

<400> SEQUENCE: 174
annncnangc annnagagn                                                  19

<210> SEQ ID NO 175
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 6, 11
<223> OTHER INFORMATION: n = T or U

<400> SEQUENCE: 175
aanacnaggc ngaaaagcc                                                  19

<210> SEQ ID NO 176
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 4, 5, 6, 9, 10, 11, 12, 14, 18, 19
<223> OTHER INFORMATION: n = T or U

<400> SEQUENCE: 176
```
ggcnnngcnn nnancagnn                                              19

<210> SEQ ID NO 177
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 3, 11, 14, 15, 16, 17, 19
<223> OTHER INFORMATION: n = T or U

<400> SEQUENCE: 177
ncnagggagg nagnnnngn                                              19

<210> SEQ ID NO 178
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 16
<223> OTHER INFORMATION: n = T or U

<400> SEQUENCE: 178
gggaagaaaa gggacnagc                                              19

<210> SEQ ID NO 179
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 3, 6, 9, 14, 18
<223> OTHER INFORMATION: n = T or U

<400> SEQUENCE: 179
gnncanaang aaangaang                                              19

<210> SEQ ID NO 180
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 8, 10, 13, 15, 16, 17, 18
<223> OTHER INFORMATION: n = T or U

<400> SEQUENCE: 180
anaagaanan gcngnnnnc                                              19

<210> SEQ ID NO 181
<211> LENGTH: 19
<212> TYPE: DNA
<213> ORGANISM: Artificial Sequence

```
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 2, 9, 11, 12, 18, 19
<223> OTHER INFORMATION: n = T or U

<400> SEQUENCE: 181
nncaaacgng nnggcgcnn                                                19

<210> SEQ ID NO 182
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 9, 12, 14, 15, 16
<223> OTHER INFORMATION: n = T or U

<400> SEQUENCE: 182
angacaagnc gnannncag                                                19

<210> SEQ ID NO 183
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 4, 9, 13, 19
<223> OTHER INFORMATION: n = T or U

<400> SEQUENCE: 183
aagnggaana cgnagacan                                                19

<210> SEQ ID NO 184
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog

<400> SEQUENCE: 184
agacaggaac cccagcagg                                                19

<210> SEQ ID NO 185
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 11, 14, 15, 16, 18
<223> OTHER INFORMATION: n = T or U

<400> SEQUENCE: 185
```
cgagcaagac nccnnncng                                              19

<210> SEQ ID NO 186
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 5, 8
<223> OTHER INFORMATION: n = T or U

<400> SEQUENCE: 186
agngnaanag aaaccagca                                              19

<210> SEQ ID NO 187
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 6, 7, 9, 12, 13
<223> OTHER INFORMATION: n = T or U

<400> SEQUENCE: 187
ngaccnngnc anncacacc                                              19

<210> SEQ ID NO 188
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 2, 4, 11
<223> OTHER INFORMATION: n = T or U

<400> SEQUENCE: 188
nnanccagca ncaggccac                                              19

<210> SEQ ID NO 189
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 5, 7, 10, 12, 13, 14, 15
<223> OTHER INFORMATION: n = T or U

<400> SEQUENCE: 189
acngncnccn cnnnnccag                                              19

<210> SEQ ID NO 190
<211> LENGTH: 19
<212> TYPE: DNA
<213> ORGANISM: Artificial Sequence

```
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 2, 3, 4, 6, 9, 10, 11, 12, 16
<223> OTHER INFORMATION: n = T or U

<400> SEQUENCE: 190
nnnnangcnn nncagnagg                                            19

<210> SEQ ID NO 191
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 6, 8, 14, 19
<223> OTHER INFORMATION: n = T or U

<400> SEQUENCE: 191
acgaancngc agcnaggan                                            19

<210> SEQ ID NO 192
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 5, 6, 8, 9, 17, 18, 19
<223> OTHER INFORMATION: n = T or U

<400> SEQUENCE: 192
caagnngnna acggaannn                                            19

<210> SEQ ID NO 193
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 6, 13, 17, 18
<223> OTHER INFORMATION: n = T or U

<400> SEQUENCE: 193
naggcngaga ggnagcnnc                                            19

<210> SEQ ID NO 194
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 3, 6
```

<223> OTHER INFORMATION: n = T or U

<400> SEQUENCE: 194
gnnacngaag aaggaaaag                                              19

<210> SEQ ID NO 195
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 4, 8, 10, 12, 17, 19
<223> OTHER INFORMATION: n = T or U

<400> SEQUENCE: 195
gaangagngn gnggaangn                                              19

<210> SEQ ID NO 196
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 3, 4, 5, 6, 8, 10
<223> OTHER INFORMATION: n = T or U

<400> SEQUENCE: 196
ngnnnncngn acccggaag                                              19

<210> SEQ ID NO 197
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 13, 15
<223> OTHER INFORMATION: n = T or U

<400> SEQUENCE: 197
gagccacgga aananccac                                              19

<210> SEQ ID NO 198
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 4, 11, 12, 13, 17
<223> OTHER INFORMATION: n = T or U

<400> SEQUENCE: 198
nganggagag nnngaanaa                                              19

```
<210> SEQ ID NO 199
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 4, 5, 8, 10, 15, 16, 17
<223> OTHER INFORMATION: n = T or U

<400> SEQUENCE: 199
gannngcncn ggagnnnac                                               19

<210> SEQ ID NO 200
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 10, 11, 13, 14, 17, 18, 19
<223> OTHER INFORMATION: n = T or U

<400> SEQUENCE: 200
ggcagaaaan ncnngannn                                               19

<210> SEQ ID NO 201
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 10, 17, 18
<223> OTHER INFORMATION: n = T or U

<400> SEQUENCE: 201
ggacaggggn aggaacnnc                                               19

<210> SEQ ID NO 202
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 4, 5, 6, 7, 10, 11, 13, 14, 17, 18
<223> OTHER INFORMATION: n = T or U

<400> SEQUENCE: 202
gcannnncgn nanncanng                                               19

<210> SEQ ID NO 203
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
```

```
          deoxyribonucleotide, or nucleotide analog
<220> FEATURE:
<221> NAME/KEY: misc_feature
<222> LOCATION: 2, 9, 13, 16, 18
<223> OTHER INFORMATION: n = T or U

<400> SEQUENCE: 203
cngaaaagna agnaancng                                              19

<210> SEQ ID NO 204
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 14, 18
<223> OTHER INFORMATION: n = T or U

<400> SEQUENCE: 204
ggcgacagaa aagncaang                                              19

<210> SEQ ID NO 205
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 5, 7, 9, 11, 17
<223> OTHER INFORMATION: n = T or U

<400> SEQUENCE: 205
ccacncngnc nccaggncc                                              19

<210> SEQ ID NO 206
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog

<400> SEQUENCE: 206
ccaccacagg caaagcaag                                              19

<210> SEQ ID NO 207
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 2, 6, 7, 13, 14, 17
<223> OTHER INFORMATION: n = T or U

<400> SEQUENCE: 207
nncggnnccc aanngcnca                                              19
```

<210> SEQ ID NO 208
<211> LENGTH: 19
<212> TYPE: DNA
<213> ORGANISM: Artificial Sequence
<220> FEATURE:
<223> OTHER INFORMATION: based on Homo sapiens.
    Each nucleobase may be part of a ribonucleotide,
    deoxyribonucleotide, or nucleotide analog
<220> FEATURE:
<221> NAME/KEY: misc_feature
<222> LOCATION: 1, 2, 4, 9, 14, 15, 17
<223> OTHER INFORMATION: n = T or U

<400> SEQUENCE: 208
nncngacana gcannancc                                                19

<210> SEQ ID NO 209
<211> LENGTH: 19
<212> TYPE: DNA
<213> ORGANISM: Artificial Sequence
<220> FEATURE:
<223> OTHER INFORMATION: based on Homo sapiens.
    Each nucleobase may be part of a ribonucleotide,
    deoxyribonucleotide, or nucleotide analog
<220> FEATURE:
<221> NAME/KEY: misc_feature
<222> LOCATION: 1, 9, 11, 13, 18
<223> OTHER INFORMATION: n = T or U

<400> SEQUENCE: 209
ngggaaaang ncncaggng                                                19

<210> SEQ ID NO 210
<211> LENGTH: 19
<212> TYPE: DNA
<213> ORGANISM: Artificial Sequence
<220> FEATURE:
<223> OTHER INFORMATION: based on Homo sapiens.
    Each nucleobase may be part of a ribonucleotide,
    deoxyribonucleotide, or nucleotide analog
<220> FEATURE:
<221> NAME/KEY: misc_feature
<222> LOCATION: 1, 3, 7, 13, 14, 15
<223> OTHER INFORMATION: n = T or U

<400> SEQUENCE: 210
nanaaanggg cannggga                                                 19

<210> SEQ ID NO 211
<211> LENGTH: 19
<212> TYPE: DNA
<213> ORGANISM: Artificial Sequence
<220> FEATURE:
<223> OTHER INFORMATION: based on Homo sapiens.
    Each nucleobase may be part of a ribonucleotide,
    deoxyribonucleotide, or nucleotide analog
<220> FEATURE:
<221> NAME/KEY: misc_feature
<222> LOCATION: 1, 3, 5, 6, 12, 15, 16, 17, 18
<223> OTHER INFORMATION: n = T or U

<400> SEQUENCE: 211
ngncnngaag cngannnnc                                                19

<210> SEQ ID NO 212
<211> LENGTH: 19
<212> TYPE: DNA
<213> ORGANISM: Artificial Sequence
<220> FEATURE:
<223> OTHER INFORMATION: based on Homo sapiens.
    Each nucleobase may be part of a ribonucleotide, deoxyribonucleotide, or nucleotide analog
<220> FEATURE:
<221> NAME/KEY: misc_feature
<222> LOCATION: 6, 8, 10, 12, 14, 15
<223> OTHER INFORMATION: n = T or U

<400> SEQUENCE: 212
gaaacngngn ancnngaag                                                  19

<210> SEQ ID NO 213
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 3, 5, 9, 12, 17, 18
<223> OTHER INFORMATION: n = T or U

<400> SEQUENCE: 213
ngncngcang cncaganna                                                  19

<210> SEQ ID NO 214
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 4, 6, 7, 8, 9, 19
<223> OTHER INFORMATION: n = T or U

<400> SEQUENCE: 214
gaangnnnna aagcgggcn                                                  19

<210> SEQ ID NO 215
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 4, 15, 16
<223> OTHER INFORMATION: n = T or U

<400> SEQUENCE: 215
cacnagaggg ccagnnaaa                                                  19

<210> SEQ ID NO 216
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 7, 8, 15, 18
<223> OTHER INFORMATION: n = T or U

<400> SEQUENCE: 216

```
ccgcacnngc aagcngcnc                                            19
```

<210> SEQ ID NO 217
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 6, 10, 12, 13
<223> OTHER INFORMATION: n = T or U

<400> SEQUENCE: 217

```
cancancacn gnnacccac                                            19
```

<210> SEQ ID NO 218
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 7
<223> OTHER INFORMATION: n = T or U

<400> SEQUENCE: 218

```
ccaccancac agcaaaagc                                            19
```

<210> SEQ ID NO 219
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 7, 8, 18
<223> OTHER INFORMATION: n = T or U

<400> SEQUENCE: 219

```
nccaganncc caacaccng                                            19
```

<210> SEQ ID NO 220
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 5, 9, 12, 14
<223> OTHER INFORMATION: n = T or U

<400> SEQUENCE: 220

```
cccangganc ancnccaga                                            19
```

<210> SEQ ID NO 221
<211> LENGTH: 19
<212> TYPE: DNA

-continued

```
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 7, 8, 13, 15, 16
<223> OTHER INFORMATION: n = T or U

<400> SEQUENCE: 221
aaccacnngg cangnngaa                                               19

<210> SEQ ID NO 222
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 5, 8, 15, 16
<223> OTHER INFORMATION: n = T or U

<400> SEQUENCE: 222
caagnacnca caccnngga                                               19

<210> SEQ ID NO 223
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 5, 8, 9, 10, 13, 14, 16, 17, 19
<223> OTHER INFORMATION: n = T or U

<400> SEQUENCE: 223
ccngnccnnn aanncnnan                                               19

<210> SEQ ID NO 224
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 6, 7, 14, 19
<223> OTHER INFORMATION: n = T or U

<400> SEQUENCE: 224
ngaacnngac ggangaacn                                               19

<210> SEQ ID NO 225
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
```

```
<222> LOCATION: 1, 5, 11, 15, 19
<223> OTHER INFORMATION: n = T or U

<400> SEQUENCE: 225
nagangaggg naacnggcn                                              19

<210> SEQ ID NO 226
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 5, 12, 14, 15
<223> OTHER INFORMATION: n = T or U

<400> SEQUENCE: 226
ngganagcag cngnncaag                                              19

<210> SEQ ID NO 227
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 4, 5, 6, 9, 11, 14, 19
<223> OTHER INFORMATION: n = T or U

<400> SEQUENCE: 227
cannnncanc nccngggcn                                              19

<210> SEQ ID NO 228
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 5, 8, 9, 12, 16, 18
<223> OTHER INFORMATION: n = T or U

<400> SEQUENCE: 228
ngganaanng angacncng                                              19

<210> SEQ ID NO 229
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 4, 5, 7, 13, 14
<223> OTHER INFORMATION: n = T or U

<400> SEQUENCE: 229
gncnncncca ggnncaaaa                                              19
```

<210> SEQ ID NO 230
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 3, 4, 7, 10, 13, 14, 18
<223> OTHER INFORMATION: n = T or U

<400> SEQUENCE: 230
nanncancan ganngcanc                                                  19

<210> SEQ ID NO 231
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 4, 5, 17, 18
<223> OTHER INFORMATION: n = T or U

<400> SEQUENCE: 231
cannnccacg gcagcanna                                                  19

<210> SEQ ID NO 232
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 7, 8, 10, 13
<223> OTHER INFORMATION: n = T or U

<400> SEQUENCE: 232
ccaggcnncn acnaaagcc                                                  19

<210> SEQ ID NO 233
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 8, 9, 10, 11, 12, 14, 16
<223> OTHER INFORMATION: n = T or U

<400> SEQUENCE: 233
gcnaggannn nncncngaa                                                  19

<210> SEQ ID NO 234
<211> LENGTH: 19
<212> TYPE: DNA
<213> ORGANISM: Artificial Sequence
<220> FEATURE:
<223> OTHER INFORMATION: based on Homo sapiens.

```
        Each nucleobase may be part of a ribonucleotide,
        deoxyribonucleotide, or nucleotide analog
<220> FEATURE:
<221> NAME/KEY: misc_feature
<222> LOCATION: 1, 3, 5, 8, 9, 11, 13, 18, 19
<223> OTHER INFORMATION: n = T or U

<400> SEQUENCE: 234
ncnanaannc ncnccagnn                                               19

<210> SEQ ID NO 235
<211> LENGTH: 19
<212> TYPE: DNA
<213> ORGANISM: Artificial Sequence
<220> FEATURE:
<223> OTHER INFORMATION: based on Homo sapiens.
        Each nucleobase may be part of a ribonucleotide,
        deoxyribonucleotide, or nucleotide analog
<220> FEATURE:
<221> NAME/KEY: misc_feature
<222> LOCATION: 9, 12, 13, 17
<223> OTHER INFORMATION: n = T or U

<400> SEQUENCE: 235
acacaaganc anngacnag                                               19

<210> SEQ ID NO 236
<211> LENGTH: 19
<212> TYPE: DNA
<213> ORGANISM: Artificial Sequence
<220> FEATURE:
<223> OTHER INFORMATION: based on Homo sapiens.
        Each nucleobase may be part of a ribonucleotide,
        deoxyribonucleotide, or nucleotide analog
<220> FEATURE:
<221> NAME/KEY: misc_feature
<222> LOCATION: 1, 3, 7, 8, 12, 16, 18
<223> OTHER INFORMATION: n = T or U

<400> SEQUENCE: 236
ncngcannga gnaagncna                                               19

<210> SEQ ID NO 237
<211> LENGTH: 19
<212> TYPE: DNA
<213> ORGANISM: Artificial Sequence
<220> FEATURE:
<223> OTHER INFORMATION: based on Homo sapiens.
        Each nucleobase may be part of a ribonucleotide,
        deoxyribonucleotide, or nucleotide analog
<220> FEATURE:
<221> NAME/KEY: misc_feature
<222> LOCATION: 2, 4, 5, 9, 10, 12, 13, 14, 17, 19
<223> OTHER INFORMATION: n = T or U

<400> SEQUENCE: 237
cncnncccnn annncancn                                               19

<210> SEQ ID NO 238
<211> LENGTH: 19
<212> TYPE: DNA
<213> ORGANISM: Artificial Sequence
<220> FEATURE:
<223> OTHER INFORMATION: based on Homo sapiens.
        Each nucleobase may be part of a ribonucleotide,
        deoxyribonucleotide, or nucleotide analog
<220> FEATURE:
<221> NAME/KEY: misc_feature
<222> LOCATION: 1, 4, 8, 9, 12, 14, 15, 16, 18
<223> OTHER INFORMATION: n = T or U
```

```
<400> SEQUENCE: 238
nccncagnng cncnnncnc                                              19

<210> SEQ ID NO 239
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 5, 6, 8, 10, 11, 13, 14
<223> OTHER INFORMATION: n = T or U

<400> SEQUENCE: 239
gccanncnan ncnnccgga                                              19

<210> SEQ ID NO 240
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 8, 10, 11, 19
<223> OTHER INFORMATION: n = T or U

<400> SEQUENCE: 240
agncaaangn ngaaaaagn                                              19

<210> SEQ ID NO 241
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 7, 8, 13, 14
<223> OTHER INFORMATION: n = T or U

<400> SEQUENCE: 241
ccagganngg aanncaca                                               19

<210> SEQ ID NO 242
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 3, 11, 12, 15
<223> OTHER INFORMATION: n = T or U

<400> SEQUENCE: 242
annccggcag nnagnagac                                              19

<210> SEQ ID NO 243
<211> LENGTH: 19
```

```
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 6, 9, 11, 12, 14, 15, 17, 18
<223> OTHER INFORMATION: n = T or U

<400> SEQUENCE: 243
naacancang nncnngnnc                                                  19

<210> SEQ ID NO 244
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 4, 6, 8, 10, 11, 13, 15, 16, 17
<223> OTHER INFORMATION: n = T or U

<400> SEQUENCE: 244
gncngngncn ncngnnnaa                                                  19

<210> SEQ ID NO 245
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 2, 4, 6, 7, 10, 11, 13
<223> OTHER INFORMATION: n = T or U

<400> SEQUENCE: 245
nncncnngcn ngnaaagac                                                  19

<210> SEQ ID NO 246
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 7, 10, 12, 16
<223> OTHER INFORMATION: n = T or U

<400> SEQUENCE: 246
cnaaaancgn ancaancag                                                  19

<210> SEQ ID NO 247
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
```

```
<221> NAME/KEY: misc_feature
<222> LOCATION: 4, 9, 11, 12, 13, 16, 17, 18, 19
<223> OTHER INFORMATION: n = T or U

<400> SEQUENCE: 247
ggcngcaana nnnccnnnn                                                     19

<210> SEQ ID NO 248
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 6, 7, 8, 10, 14, 19
<223> OTHER INFORMATION: n = T or U

<400> SEQUENCE: 248
gagagnnncn gaanacagn                                                     19

<210> SEQ ID NO 249
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 6, 7, 12, 13, 15, 16
<223> OTHER INFORMATION: n = T or U

<400> SEQUENCE: 249
acagcnncag cnncnngca                                                     19

<210> SEQ ID NO 250
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 4, 8, 11, 14, 16
<223> OTHER INFORMATION: n = T or U

<400> SEQUENCE: 250
aaanaaangc ncananaac                                                     19

<210> SEQ ID NO 251
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 7, 9, 10, 12, 14
<223> OTHER INFORMATION: n = T or U

<400> SEQUENCE: 251
gaaacancnn cngnggaa                                                      19
```

<210> SEQ ID NO 252
<211> LENGTH: 19
<212> TYPE: DNA
<213> ORGANISM: Artificial Sequence
<220> FEATURE:
<223> OTHER INFORMATION: based on Homo sapiens.
    Each nucleobase may be part of a ribonucleotide,
    deoxyribonucleotide, or nucleotide analog
<220> FEATURE:
<221> NAME/KEY: misc_feature
<222> LOCATION: 2, 3, 5, 6, 11, 14, 18
<223> OTHER INFORMATION: n = T or U

<400> SEQUENCE: 252
gnncnnccac nggnaganc                                                19

<210> SEQ ID NO 253
<211> LENGTH: 19
<212> TYPE: DNA
<213> ORGANISM: Artificial Sequence
<220> FEATURE:
<223> OTHER INFORMATION: based on Homo sapiens.
    Each nucleobase may be part of a ribonucleotide,
    deoxyribonucleotide, or nucleotide analog
<220> FEATURE:
<221> NAME/KEY: misc_feature
<222> LOCATION: 2, 3, 5, 6, 8, 11, 13
<223> OTHER INFORMATION: n = T or U

<400> SEQUENCE: 253
cnncnngnag ncnccgcaa                                                19

<210> SEQ ID NO 254
<211> LENGTH: 19
<212> TYPE: DNA
<213> ORGANISM: Artificial Sequence
<220> FEATURE:
<223> OTHER INFORMATION: based on Homo sapiens.
    Each nucleobase may be part of a ribonucleotide,
    deoxyribonucleotide, or nucleotide analog
<220> FEATURE:
<221> NAME/KEY: misc_feature
<222> LOCATION: 1, 2, 4, 8, 15, 16, 17
<223> OTHER INFORMATION: n = T or U

<400> SEQUENCE: 254
nngnccanac acacnnnac                                                19

<210> SEQ ID NO 255
<211> LENGTH: 19
<212> TYPE: DNA
<213> ORGANISM: Artificial Sequence
<220> FEATURE:
<223> OTHER INFORMATION: based on Homo sapiens.
    Each nucleobase may be part of a ribonucleotide,
    deoxyribonucleotide, or nucleotide analog
<220> FEATURE:
<221> NAME/KEY: misc_feature
<222> LOCATION: 8, 9, 14
<223> OTHER INFORMATION: n = T or U

<400> SEQUENCE: 255
aaccaaanna gganaaaag                                                19

<210> SEQ ID NO 256
<211> LENGTH: 19
<212> TYPE: DNA
<213> ORGANISM: Artificial Sequence
<220> FEATURE:

<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 4, 5, 8, 10, 13, 14, 15, 19
<223> OTHER INFORMATION: n = T or U

<400> SEQUENCE: 256
angnncanan ggnnnagan                                          19

<210> SEQ ID NO 257
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 5, 6, 7, 8, 11, 12, 16, 17
<223> OTHER INFORMATION: n = T or U

<400> SEQUENCE: 257
naagnnnnac nncacnnac                                          19

<210> SEQ ID NO 258
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 4, 5, 11, 13, 14, 17
<223> OTHER INFORMATION: n = T or U

<400> SEQUENCE: 258
angnncccgg nannagnac                                          19

<210> SEQ ID NO 259
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 5, 10, 13, 14, 16, 18, 19
<223> OTHER INFORMATION: n = T or U

<400> SEQUENCE: 259
gggcncaagn aanncncnn                                          19

<210> SEQ ID NO 260
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 9, 13, 14
<223> OTHER INFORMATION: n = T or U

```
<400> SEQUENCE: 260
gcccaggang ganncaaac                                                19

<210> SEQ ID NO 261
<211> LENGTH: 19
<212> TYPE: DNA
<213> ORGANISM: Artificial Sequence
<220> FEATURE:
<223> OTHER INFORMATION: based on Homo sapiens.
      DNA/RNA hybrid.

<400> SEQUENCE: 261
gagaagatga ctggtaaca                                                19

<210> SEQ ID NO 262
<211> LENGTH: 18
<212> TYPE: DNA
<213> ORGANISM: Artificial Sequence
<220> FEATURE:
<223> OTHER INFORMATION: based on Homo sapiens.
      DNA/RNA hybrid
<220> FEATURE:
<221> NAME/KEY: misc_feature
<222> LOCATION: 1, 17, 18
<223> OTHER INFORMATION: n = T or U

<400> SEQUENCE: 262
ngtgctattc tgtgaann                                                 18

<210> SEQ ID NO 263
<211> LENGTH: 20
<212> TYPE: DNA
<213> ORGANISM: Artificial Sequence
<220> FEATURE:
<223> OTHER INFORMATION: based on Homo sapiens.

<400> SEQUENCE: 263
tctgcttcaa ggagctggaa                                               20

<210> SEQ ID NO 264
<211> LENGTH: 18
<212> TYPE: DNA
<213> ORGANISM: Artificial Sequence
<220> FEATURE:
<223> OTHER INFORMATION: based on Homo sapiens.

<400> SEQUENCE: 264
gaaaggaaag cgcaaccg                                                 18

<210> SEQ ID NO 265
<211> LENGTH: 30
<212> TYPE: DNA
<213> ORGANISM: Artificial Sequence
<220> FEATURE:
<223> OTHER INFORMATION: based on Homo sapiens.

<400> SEQUENCE: 265
agccagatga cgaccccata gaggaacata                                    30

<210> SEQ ID NO 266
<211> LENGTH: 21
<212> TYPE: DNA
<213> ORGANISM: Artificial Sequence
<220> FEATURE:
<223> OTHER INFORMATION: based on Homo sapiens.
```

-continued

```
<400> SEQUENCE: 266
tggagatgat ccatgggttc a                                              21

<210> SEQ ID NO 267
<211> LENGTH: 29
<212> TYPE: DNA
<213> ORGANISM: Artificial Sequence
<220> FEATURE:
<223> OTHER INFORMATION: based on Homo sapiens.

<400> SEQUENCE: 267
gaactcctgt cctttaattc ttatcaagt                                      29

<210> SEQ ID NO 268
<211> LENGTH: 27
<212> TYPE: DNA
<213> ORGANISM: Artificial Sequence
<220> FEATURE:
<223> OTHER INFORMATION: based on Homo sapiens.

<400> SEQUENCE: 268
ctcacacctt ggaaaccact tggcatg                                        27

<210> SEQ ID NO 269
<211> LENGTH: 27
<212> TYPE: DNA
<213> ORGANISM: Artificial Sequence
<220> FEATURE:
<223> OTHER INFORMATION: based on Homo sapiens.

<400> SEQUENCE: 269
ggtgataaag taaagtgctt tcactgt                                        27

<210> SEQ ID NO 270
<211> LENGTH: 28
<212> TYPE: DNA
<213> ORGANISM: Artificial Sequence
<220> FEATURE:
<223> OTHER INFORMATION: based on Homo sapiens.

<400> SEQUENCE: 270
tcagtagttc ttaccagaca ctcctcaa                                       28

<210> SEQ ID NO 271
<211> LENGTH: 34
<212> TYPE: DNA
<213> ORGANISM: Artificial Sequence
<220> FEATURE:
<223> OTHER INFORMATION: based on Homo sapiens.

<400> SEQUENCE: 271
caacatgcta aatggtatcc agggtgcaaa tatc                                34

<210> SEQ ID NO 272
<211> LENGTH: 19
<212> TYPE: DNA
<213> ORGANISM: Artificial Sequence
<220> FEATURE:
<223> OTHER INFORMATION: based on Homo sapiens.

<400> SEQUENCE: 272
gaaggtgaag gtcggagtc                                                 19

<210> SEQ ID NO 273
<211> LENGTH: 19
```

```
<212> TYPE: DNA
<213> ORGANISM: Artificial Sequence
<220> FEATURE:
<223> OTHER INFORMATION: based on Homo sapiens.

<400> SEQUENCE: 273
gaagatggtg atgggattc                                              19

<210> SEQ ID NO 274
<211> LENGTH: 20
<212> TYPE: DNA
<213> ORGANISM: Artificial Sequence
<220> FEATURE:
<223> OTHER INFORMATION: based on Homo sapiens.

<400> SEQUENCE: 274
caagcttccc gttctcagcc                                             20

<210> SEQ ID NO 275
<211> LENGTH: 19
<212> TYPE: DNA
<213> ORGANISM: Artificial Sequence
<220> FEATURE:
<223> OTHER INFORMATION: based on Homo sapiens.  Each nucleobase is
      part of a deoxyribonucleotide or ribonucleotide.

<400> SEQUENCE: 275
cagagatttc atttaacgu                                              19

<210> SEQ ID NO 276
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a
      deoxyribonucleotide or ribonucleotide

<400> SEQUENCE: 276
cuacgctcgc catcgtuca                                              19

<210> SEQ ID NO 277
<211> LENGTH: 19
<212> TYPE: DNA
<213> ORGANISM: Artificial Sequence
<220> FEATURE:
<223> OTHER INFORMATION: based on Homo sapiens.
      Each nucleobase is part of a deoxyribonucleotide
      or ribonucleotide

<400> SEQUENCE: 277
ugcccaagaa tactaguca                                              19

<210> SEQ ID NO 278
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 4, 5, 7, 9, 10, 16
<223> OTHER INFORMATION: n = T or U

<400> SEQUENCE: 278
ancnncncnn gaaaanagg                                              19
```

```
<210> SEQ ID NO 279
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 4, 5, 7, 9, 10, 16
<223> OTHER INFORMATION: n = T or U

<400> SEQUENCE: 279
ancnncncnn gaaaanagg                                                19

<210> SEQ ID NO 280
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 4, 10, 11, 13, 15, 16, 18
<223> OTHER INFORMATION: n = T or U

<400> SEQUENCE: 280
gganaaaagn ncncnncna                                                19

<210> SEQ ID NO 281
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 7, 9, 13, 15, 16
<223> OTHER INFORMATION: n = T or U

<400> SEQUENCE: 281
gcngagncnc cananngcc                                                19

<210> SEQ ID NO 282
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 7, 9, 13, 15, 16
<223> OTHER INFORMATION: n = T or U

<400> SEQUENCE: 282
gcngagncnc cananngcc                                                19

<210> SEQ ID NO 283
<211> LENGTH: 19
<212> TYPE: DNA
<213> ORGANISM: Artificial Sequence
<220> FEATURE:
```

```
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 4, 6, 7, 8, 15, 19
<223> OTHER INFORMATION: n = T or U

<400> SEQUENCE: 283
ggcncnnngc ccacngaan                                                19

<210> SEQ ID NO 284
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 5, 6, 8, 12
<223> OTHER INFORMATION: n = T or U

<400> SEQUENCE: 284
accanncngg anaccagaa                                                19

<210> SEQ ID NO 285
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 5, 6, 8, 12
<223> OTHER INFORMATION: n = T or U

<400> SEQUENCE: 285
accanncngg anaccagaa                                                19

<210> SEQ ID NO 286
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 8, 12, 14, 15
<223> OTHER INFORMATION: n = T or U

<400> SEQUENCE: 286
aagaccanag gncnnacca                                                19

<210> SEQ ID NO 287
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 4, 5, 8, 13, 15, 17
<223> OTHER INFORMATION: n = T or U
```

<400> SEQUENCE: 287
gggnnccncg ggnanangg                                                19

<210> SEQ ID NO 288
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 5, 7, 12, 15, 16
<223> OTHER INFORMATION: n = T or U

<400> SEQUENCE: 288
ggnananggc gnccnnggg                                                19

<210> SEQ ID NO 289
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 5, 7, 10, 11, 18
<223> OTHER INFORMATION: n = T or U

<400> SEQUENCE: 289
ggnancnccn ncaccagna                                                19

<210> SEQ ID NO 290
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 9, 10, 13, 15, 17
<223> OTHER INFORMATION: n = T or U

<400> SEQUENCE: 290
angaccacnn ccncnangg                                                19

<210> SEQ ID NO 291
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 4, 8, 9, 14, 16, 17
<223> OTHER INFORMATION: n = T or U

<400> SEQUENCE: 291
ganncacnnc gaanannaa                                                19

<210> SEQ ID NO 292

```
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 4, 6, 11, 12, 16, 17
<223> OTHER INFORMATION: n = T or U

<400> SEQUENCE: 292
aannanaacg nncacnnag                                                19

<210> SEQ ID NO 293
<211> LENGTH: 27
<212> TYPE: DNA
<213> ORGANISM: Artificial Sequence
<220> FEATURE:
<223> OTHER INFORMATION: based on Homo sapiens.

<400> SEQUENCE: 293
ggtgataaag taaagtgctt tcactgt                                       27

<210> SEQ ID NO 294
<211> LENGTH: 33
<212> TYPE: DNA
<213> ORGANISM: Artificial Sequence
<220> FEATURE:
<223> OTHER INFORMATION: based on Homo sapiens.

<400> SEQUENCE: 294
caacatgcta aatggttcca gggtgcaaat atc                                33

<210> SEQ ID NO 295
<211> LENGTH: 28
<212> TYPE: DNA
<213> ORGANISM: Artificial Sequence
<220> FEATURE:
<223> OTHER INFORMATION: based on Homo sapiens.

<400> SEQUENCE: 295
tcagtagttc ttaccagaca ctcctcaa                                      28

<210> SEQ ID NO 296
<211> LENGTH: 19
<212> TYPE: DNA
<213> ORGANISM: Artificial Sequence
<220> FEATURE:
<223> OTHER INFORMATION: based on Homo sapiens.
      DNA/RNA hybrid.

<400> SEQUENCE: 296
uaagctgttc tatgtguuc                                                19

<210> SEQ ID NO 297
<211> LENGTH: 19
<212> TYPE: DNA
<213> ORGANISM: Artificial Sequence
<220> FEATURE:
<223> OTHER INFORMATION: based on Homo sapiens.

<400> SEQUENCE: 297
aagggcggcg gagtgagac                                                19

<210> SEQ ID NO 298
```

```
<211> LENGTH: 19
<212> TYPE: DNA
<213> ORGANISM: Artificial Sequence
<220> FEATURE:
<223> OTHER INFORMATION: based on Homo sapiens.

<400> SEQUENCE: 298
agaggacgga gtcggaggc                                            19

<210> SEQ ID NO 299
<211> LENGTH: 19
<212> TYPE: DNA
<213> ORGANISM: Artificial Sequence
<220> FEATURE:
<223> OTHER INFORMATION: based on Homo sapiens.

<400> SEQUENCE: 299
cggagcgtga ggatggaga                                            19

<210> SEQ ID NO 300
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 18
<223> OTHER INFORMATION: n = T or U

<400> SEQUENCE: 300
agcaaggaca agcccagnc                                            19

<210> SEQ ID NO 301
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 3, 9, 12
<223> OTHER INFORMATION: n = T or U

<400> SEQUENCE: 301
ngnaaaccng cngcccaga                                            19

<210> SEQ ID NO 302
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 6, 9, 10, 11, 12, 15, 18, 19
<223> OTHER INFORMATION: n = T or U

<400> SEQUENCE: 302
agaagncgnn nnccnccnn                                            19

<210> SEQ ID NO 303
<211> LENGTH: 19
```

```
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 7, 8, 13, 17
<223> OTHER INFORMATION: n = T or U

<400> SEQUENCE: 303
ccgagannag acnaagncc                                              19

<210> SEQ ID NO 304
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 4, 5, 6, 9, 10, 11, 13, 14, 15
<223> OTHER INFORMATION: n = T or U

<400> SEQUENCE: 304
acnnnnccnn nannnccac                                              19

<210> SEQ ID NO 305
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 14, 17, 19
<223> OTHER INFORMATION: n = T or U

<400> SEQUENCE: 305
ncccaaacac aggnacnan                                              19

<210> SEQ ID NO 306
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 4, 6, 13
<223> OTHER INFORMATION: n = T or U

<400> SEQUENCE: 306
canncncagc ggnaacagc                                              19

<210> SEQ ID NO 307
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
```

```
<221> NAME/KEY: misc_feature
<222> LOCATION: 5, 8, 9, 11, 14, 17
<223> OTHER INFORMATION: n = T or U

<400> SEQUENCE: 307
accancannc ncanccnca                                                        19

<210> SEQ ID NO 308
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 5, 10, 11, 18
<223> OTHER INFORMATION: n = T or U

<400> SEQUENCE: 308
aangnaaccn ncaaccanc                                                        19

<210> SEQ ID NO 309
<211> LENGTH: 18
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 2, 3, 5, 7, 8, 11, 15, 17
<223> OTHER INFORMATION: n = T or U

<400> SEQUENCE: 309
nnngnannca ncacngnc                                                         18

<210> SEQ ID NO 310
<211> LENGTH: 18
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 6, 8, 11, 12
<223> OTHER INFORMATION: n = T or U

<400> SEQUENCE: 310
ncacancnca nnaccaac                                                         18

<210> SEQ ID NO 311
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 6
<223> OTHER INFORMATION: n = T or U

<400> SEQUENCE: 311
ccaggnggca ggagaaaca                                                        19
```

<210> SEQ ID NO 312
<211> LENGTH: 19
<212> TYPE: DNA
<213> ORGANISM: Artificial Sequence
<220> FEATURE:
<223> OTHER INFORMATION: based on Homo sapiens.
    Each nucleobase may be part of a ribonucleotide,
    deoxyribonucleotide, or nucleotide analog
<220> FEATURE:
<221> NAME/KEY: misc_feature
<222> LOCATION: 1, 8, 9, 13, 16, 17, 18
<223> OTHER INFORMATION: n = T or U

<400> SEQUENCE: 312
ngcagacnnc aangcnnng                                               19

<210> SEQ ID NO 313
<211> LENGTH: 19
<212> TYPE: DNA
<213> ORGANISM: Artificial Sequence
<220> FEATURE:
<223> OTHER INFORMATION: based on Homo sapiens.
    Each nucleobase may be part of a ribonucleotide,
    deoxyribonucleotide, or nucleotide analog
<220> FEATURE:
<221> NAME/KEY: misc_feature
<222> LOCATION: 1, 9, 13, 15, 19
<223> OTHER INFORMATION: n = T or U

<400> SEQUENCE: 313
naagcaagnc acngnggcn                                               19

<210> SEQ ID NO 314
<211> LENGTH: 19
<212> TYPE: DNA
<213> ORGANISM: Artificial Sequence
<220> FEATURE:
<223> OTHER INFORMATION: based on Homo sapiens.
    Each nucleobase may be part of a ribonucleotide,
    deoxyribonucleotide, or nucleotide analog
<220> FEATURE:
<221> NAME/KEY: misc_feature
<222> LOCATION: 2, 6, 10, 13, 16
<223> OTHER INFORMATION: n = T or U

<400> SEQUENCE: 314
cngagncgan aanacnagc                                               19

<210> SEQ ID NO 315
<211> LENGTH: 19
<212> TYPE: DNA
<213> ORGANISM: Artificial Sequence
<220> FEATURE:
<223> OTHER INFORMATION: based on Homo sapiens.
    Each nucleobase may be part of a ribonucleotide,
    deoxyribonucleotide, or nucleotide analog
<220> FEATURE:
<221> NAME/KEY: misc_feature
<222> LOCATION: 3, 9, 10, 13
<223> OTHER INFORMATION: n = T or U

<400> SEQUENCE: 315
acnagccann agnaaagag                                               19

<210> SEQ ID NO 316
<211> LENGTH: 19
<212> TYPE: DNA
<213> ORGANISM: Artificial Sequence
<220> FEATURE:

```
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 15, 16, 18
<223> OTHER INFORMATION: n = T or U

<400> SEQUENCE: 316
caacagcaga gaccnngnc                                               19

<210> SEQ ID NO 317
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 7, 11, 12
<223> OTHER INFORMATION: n = T or U

<400> SEQUENCE: 317
anagcanacc nngaaccag                                               19

<210> SEQ ID NO 318
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 5, 7, 12, 17
<223> OTHER INFORMATION: n = T or U

<400> SEQUENCE: 318
cancngnagg cnaagangg                                               19

<210> SEQ ID NO 319
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 4, 11, 16, 18
<223> OTHER INFORMATION: n = T or U

<400> SEQUENCE: 319
agnnaccaga ngccancng                                               19

<210> SEQ ID NO 320
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 5, 8, 10, 13, 16
<223> OTHER INFORMATION: n = T or U
```

```
<400> SEQUENCE: 320
aancnacncn ganagngga                                              19

<210> SEQ ID NO 321
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 3, 4, 6, 17
<223> OTHER INFORMATION: n = T or U

<400> SEQUENCE: 321
gnnncngaag ccaacanca                                              19

<210> SEQ ID NO 322
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 6, 7, 9, 14, 17
<223> OTHER INFORMATION: n = T or U

<400> SEQUENCE: 322
ncaacnnanc accnccnga                                              19

<210> SEQ ID NO 323
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 7, 12, 13, 15
<223> OTHER INFORMATION: n = T or U

<400> SEQUENCE: 323
aagaacnaac anngnagag                                              19

<210> SEQ ID NO 324
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 13, 16
<223> OTHER INFORMATION: n = T or U

<400> SEQUENCE: 324
gnagacaaca ggngcngca                                              19

<210> SEQ ID NO 325
```

```
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 4, 7, 9, 11, 14, 15, 17
<223> OTHER INFORMATION: n = T or U

<400> SEQUENCE: 325
angnccncng naannangg                                           19

<210> SEQ ID NO 326
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 4, 5, 9, 16
<223> OTHER INFORMATION: n = T or U

<400> SEQUENCE: 326
nacnnggcna gaacangga                                           19

<210> SEQ ID NO 327
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 9, 13, 15, 16
<223> OTHER INFORMATION: n = T or U

<400> SEQUENCE: 327
gaagcaacnc aangnnaag                                           19

<210> SEQ ID NO 328
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 2, 3, 6, 8, 9, 10, 11, 16
<223> OTHER INFORMATION: n = T or U

<400> SEQUENCE: 328
nnnggncnnn nggacncag                                           19

<210> SEQ ID NO 329
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
```

```
<220> FEATURE:
<221> NAME/KEY: misc_feature
<222> LOCATION: 4, 8, 11, 18
<223> OTHER INFORMATION: n = T or U

<400> SEQUENCE: 329
ccanaganca ncaggaana                                                   19

<210> SEQ ID NO 330
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 7, 11, 18
<223> OTHER INFORMATION: n = T or U

<400> SEQUENCE: 330
caggacnggc naacacanc                                                   19

<210> SEQ ID NO 331
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 2, 3, 6, 15, 17
<223> OTHER INFORMATION: n = T or U

<400> SEQUENCE: 331
nnnaanggca ggcancncc                                                   19

<210> SEQ ID NO 332
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 2, 9, 15
<223> OTHER INFORMATION: n = T or U

<400> SEQUENCE: 332
nnaagccanc aggangcca                                                   19

<210> SEQ ID NO 333
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 10, 15, 17, 19
<223> OTHER INFORMATION: n = T or U

<400> SEQUENCE: 333
```
gcnacagagn aagcngngn                                                19

<210> SEQ ID NO 334
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 4, 12, 15, 16, 17, 18
<223> OTHER INFORMATION: n = T or U

<400> SEQUENCE: 334
cncnagggag gnagnnnng                                                19

<210> SEQ ID NO 335
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 13, 18, 19
<223> OTHER INFORMATION: n = T or U

<400> SEQUENCE: 335
aagaaaaggg acnagccnn                                                19

<210> SEQ ID NO 336
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 4, 5, 10, 17
<223> OTHER INFORMATION: n = T or U

<400> SEQUENCE: 336
cagnncacan gacaagncg                                                19

<210> SEQ ID NO 337
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 4, 7, 8, 9, 11
<223> OTHER INFORMATION: n = T or U

<400> SEQUENCE: 337
gacnccnnnc ngagacagg                                                19

<210> SEQ ID NO 338
<211> LENGTH: 19
<212> TYPE: DNA
<213> ORGANISM: Artificial Sequence

```
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 3, 12, 14, 17
<223> OTHER INFORMATION: n = T or U

<400> SEQUENCE: 338
anncacacca gngnaanag                                                19

<210> SEQ ID NO 339
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 9, 10, 11, 16, 17, 19
<223> OTHER INFORMATION: n = T or U

<400> SEQUENCE: 339
cagaagcann ngaccnngn                                                19

<210> SEQ ID NO 340
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 7
<223> OTHER INFORMATION: n = T or U

<400> SEQUENCE: 340
ccagcancag gccacaaca                                                19

<210> SEQ ID NO 341
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 2, 3, 7, 13, 15, 17
<223> OTHER INFORMATION: n = T or U

<400> SEQUENCE: 341
nnncagnagg acngncncc                                                19

<210> SEQ ID NO 342
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 7, 12, 18, 19
```

<223> OTHER INFORMATION: n = T or U

<400> SEQUENCE: 342
ngcagcnagg anacaacnn                                           19

<210> SEQ ID NO 343
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 6, 10, 11, 17, 18
<223> OTHER INFORMATION: n = T or U

<400> SEQUENCE: 343
agaggnagcn nccaagnng                                           19

<210> SEQ ID NO 344
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 5, 8, 12, 14, 16
<223> OTHER INFORMATION: n = T or U

<400> SEQUENCE: 344
gaagnaanga gngngngga                                           19

<210> SEQ ID NO 345
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 4, 5, 6, 9, 16, 17, 18
<223> OTHER INFORMATION: n = T or U

<400> SEQUENCE: 345
ggannngang gagagnnng                                           19

<210> SEQ ID NO 346
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 5, 6, 8, 11
<223> OTHER INFORMATION: n = T or U

<400> SEQUENCE: 346
gaacnncnca ncaaggcag                                           19

```
<210> SEQ ID NO 347
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 4, 7, 9, 11, 14
<223> OTHER INFORMATION: n = T or U

<400> SEQUENCE: 347
aggnccnang nagnaaaag                                              19

<210> SEQ ID NO 348
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 4, 5, 6, 7
<223> OTHER INFORMATION: n = T or U

<400> SEQUENCE: 348
caannnncca ccacaggca                                              19

<210> SEQ ID NO 349
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 4, 6, 9, 10, 14, 15
<223> OTHER INFORMATION: n = T or U

<400> SEQUENCE: 349
cannanccnn cggnnccca                                              19

<210> SEQ ID NO 350
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 7, 9, 10, 12, 17
<223> OTHER INFORMATION: n = T or U

<400> SEQUENCE: 350
cncaggngnn cngacanag                                              19

<210> SEQ ID NO 351
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
```

```
          deoxyribonucleotide, or nucleotide analog
<220> FEATURE:
<221> NAME/KEY: misc_feature
<222> LOCATION: 3, 8, 9, 16, 18
<223> OTHER INFORMATION: n = T or U

<400> SEQUENCE: 351
gcncaganna gaaacngng                                                  19

<210> SEQ ID NO 352
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 6, 8, 10, 12, 16, 19
<223> OTHER INFORMATION: n = T or U

<400> SEQUENCE: 352
cngcangngn cngcangcn                                                  19

<210> SEQ ID NO 353
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 2, 6, 14
<223> OTHER INFORMATION: n = T or U

<400> SEQUENCE: 353
nnaacnagaa cacnagagg                                                  19

<210> SEQ ID NO 354
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 6, 19
<223> OTHER INFORMATION: n = T or U

<400> SEQUENCE: 354
canaanaaaa acccgcacn                                                  19

<210> SEQ ID NO 355
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 6
<223> OTHER INFORMATION: n = T or U

<400> SEQUENCE: 355
```
caccancaca gcaaaagca 19

<210> SEQ ID NO 356
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 8, 9, 19
<223> OTHER INFORMATION: n = T or U

<400> SEQUENCE: 356
cnccagannc ccaacaccn 19

<210> SEQ ID NO 357
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 10, 11, 16, 18, 19
<223> OTHER INFORMATION: n = T or U

<400> SEQUENCE: 357
ggaaaccacn nggcangnn 19

<210> SEQ ID NO 358
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 3, 8, 12, 18
<223> OTHER INFORMATION: n = T or U

<400> SEQUENCE: 358
gnncaagnag angagggna 19

<210> SEQ ID NO 359
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 6, 7, 10, 14, 16
<223> OTHER INFORMATION: n = T or U

<400> SEQUENCE: 359
ganaanngan gacncngca 19

<210> SEQ ID NO 360
<211> LENGTH: 19
<212> TYPE: DNA

```
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 5, 7, 8, 10, 16, 17
<223> OTHER INFORMATION: n = T or U

<400> SEQUENCE: 360
anggncnncn ccaggnnca                                                19

<210> SEQ ID NO 361
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 4, 5, 8, 17, 19
<223> OTHER INFORMATION: n = T or U

<400> SEQUENCE: 361
gcannaanca cagggggnan                                               19

<210> SEQ ID NO 362
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 10, 11, 12
<223> OTHER INFORMATION: n = T or U

<400> SEQUENCE: 362
naaagcccan nnccacggc                                                19

<210> SEQ ID NO 363
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 2, 9, 15
<223> OTHER INFORMATION: n = T or U

<400> SEQUENCE: 363
nnaagccanc aggangcca                                                19

<210> SEQ ID NO 364
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
```

```
<222> LOCATION: 3, 4, 5, 6, 7, 9, 11, 16, 18
<223> OTHER INFORMATION: n = T or U

<400> SEQUENCE: 364 gannnncnc ngaacngnc                                                19

<210> SEQ ID NO 365
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 4, 7, 8, 10, 12, 17, 18
<223> OTHER INFORMATION: n = T or U

<400> SEQUENCE: 365
cnanaanncn cnccagnng                                               19

<210> SEQ ID NO 366
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 9, 12, 13, 17
<223> OTHER INFORMATION: n = T or U

<400> SEQUENCE: 366
acacaaganc anngacnag                                               19

<210> SEQ ID NO 367
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 3, 7, 8, 12, 16, 18
<223> OTHER INFORMATION: n = T or U

<400> SEQUENCE: 367
ncngcannga gnaagncna                                               19

<210> SEQ ID NO 368
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 3, 4, 5, 6, 7, 10, 14, 15, 18
<223> OTHER INFORMATION: n = T or U

<400> SEQUENCE: 368
ncnnnnnccn cagnngcnc                                               19
```

<210> SEQ ID NO 369
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 7, 8, 10, 12, 13, 15, 16
<223> OTHER INFORMATION: n = T or U

<400> SEQUENCE: 369
gngccanncn anncnnccg                                                19

<210> SEQ ID NO 370
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 7, 9, 16, 17
<223> OTHER INFORMATION: n = T or U

<400> SEQUENCE: 370
gnagacnanc cagganngg                                                19

<210> SEQ ID NO 371
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 4, 6, 8, 9, 12, 13, 15
<223> OTHER INFORMATION: n = T or U

<400> SEQUENCE: 371
agnncncnng cnngnaaag                                                19

<210> SEQ ID NO 372
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 4, 6, 10, 14, 15, 17, 19
<223> OTHER INFORMATION: n = T or U

<400> SEQUENCE: 372
ncgnancaan cagnncncn                                                19

<210> SEQ ID NO 373
<211> LENGTH: 19
<212> TYPE: DNA
<213> ORGANISM: Artificial Sequence
<220> FEATURE:
<223> OTHER INFORMATION: based on Homo sapiens.

```
        Each nucleobase may be part of a ribonucleotide,
        deoxyribonucleotide, or nucleotide analog
<220> FEATURE:
<221> NAME/KEY: misc_feature
<222> LOCATION: 9, 10, 11, 13, 17
<223> OTHER INFORMATION: n = T or U

<400> SEQUENCE: 373
gcagagagnn ncngaaanac                                                    19

<210> SEQ ID NO 374
<211> LENGTH: 19
<212> TYPE: DNA
<213> ORGANISM: Artificial Sequence
<220> FEATURE:
<223> OTHER INFORMATION: based on Homo sapiens.
        Each nucleobase may be part of a ribonucleotide,
        deoxyribonucleotide, or nucleotide analog
<220> FEATURE:
<221> NAME/KEY: misc_feature
<222> LOCATION: 2, 4, 7, 9, 10, 18
<223> OTHER INFORMATION: n = T or U

<400> SEQUENCE: 374
angnccngnn gcacaaana                                                     19

<210> SEQ ID NO 375
<211> LENGTH: 19
<212> TYPE: DNA
<213> ORGANISM: Artificial Sequence
<220> FEATURE:
<223> OTHER INFORMATION: based on Homo sapiens.
        Each nucleobase may be part of a ribonucleotide,
        deoxyribonucleotide, or nucleotide analog
<220> FEATURE:
<221> NAME/KEY: misc_feature
<222> LOCATION: 2, 9, 11, 12, 14, 16
<223> OTHER INFORMATION: n = T or U

<400> SEQUENCE: 375
cngaaacanc nncngnggg                                                     19

<210> SEQ ID NO 376
<211> LENGTH: 19
<212> TYPE: DNA
<213> ORGANISM: Artificial Sequence
<220> FEATURE:
<223> OTHER INFORMATION: based on Homo sapiens.
        Each nucleobase may be part of a ribonucleotide,
        deoxyribonucleotide, or nucleotide analog
<220> FEATURE:
<221> NAME/KEY: misc_feature
<222> LOCATION: 1, 2, 3, 5, 6, 8, 9, 11, 14, 16
<223> OTHER INFORMATION: n = T or U

<400> SEQUENCE: 376
nnncnncnng nagncnccg                                                     19

<210> SEQ ID NO 377
<211> LENGTH: 19
<212> TYPE: DNA
<213> ORGANISM: Artificial Sequence
<220> FEATURE:
<223> OTHER INFORMATION: based on Homo sapiens.
        Each nucleobase may be part of a ribonucleotide,
        deoxyribonucleotide, or nucleotide analog
<220> FEATURE:
<221> NAME/KEY: misc_feature
<222> LOCATION: 2, 3, 5, 6, 7, 9, 13
<223> OTHER INFORMATION: n = T or U
```

<400> SEQUENCE: 377
cnncnnngnc canacacac                                                    19

<210> SEQ ID NO 378
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 5, 12, 14
<223> OTHER INFORMATION: n = T or U

<400> SEQUENCE: 378
ggaanaaaca cnanggaca                                                    19

<210> SEQ ID NO 379
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 6, 9, 13
<223> OTHER INFORMATION: n = T or U

<400> SEQUENCE: 379
canacnacna gangaccac                                                    19

<210> SEQ ID NO 380
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 3, 8, 9, 12, 13, 15, 18
<223> OTHER INFORMATION: n = T or U

<400> SEQUENCE: 380
ngnacccnng anngnacnc                                                    19

<210> SEQ ID NO 381
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 5, 7, 14, 16
<223> OTHER INFORMATION: n = T or U

<400> SEQUENCE: 381
gaaangnacg aacngnacc                                                    19

<210> SEQ ID NO 382
<211> LENGTH: 19

```
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 5, 6, 7, 8, 11, 12, 14, 15, 17, 18
<223> OTHER INFORMATION: n = T or U

<400> SEQUENCE: 382
gangnnnngg nncnncnnc                                           19

<210> SEQ ID NO 383
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 4, 7, 8, 10, 12, 13, 16, 17, 18
<223> OTHER INFORMATION: n = T or U

<400> SEQUENCE: 383
cnancanncn cnnagnnnc                                           19

<210> SEQ ID NO 384
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 6, 10, 11, 14, 16, 17
<223> OTHER INFORMATION: n = T or U

<400> SEQUENCE: 384
acaccnggcn ncangnncc                                           19

<210> SEQ ID NO 385
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 4, 14
<223> OTHER INFORMATION: n = T or U

<400> SEQUENCE: 385
gacnacaggc acanaccac                                           19

<210> SEQ ID NO 386
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
```

```
<221> NAME/KEY: misc_feature
<222> LOCATION: 1, 5, 11, 17
<223> OTHER INFORMATION: n = T or U

<400> SEQUENCE: 386
ngccncagcc ngggacnac                                                  19

<210> SEQ ID NO 387
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 5, 9, 10, 16, 19
<223> OTHER INFORMATION: n = T or U

<400> SEQUENCE: 387
agganggann caaacnccn                                                  19

<210> SEQ ID NO 388
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 7, 9, 11, 15, 18
<223> OTHER INFORMATION: n = T or U

<400> SEQUENCE: 388
gagaaangng ncccnggng                                                  19

<210> SEQ ID NO 389
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 16, 17, 18
<223> OTHER INFORMATION: n = T or U

<400> SEQUENCE: 389
gccacaacag aagcannng                                                  19

<210> SEQ ID NO 390
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 2, 4, 11, 13, 14, 18
<223> OTHER INFORMATION: n = T or U

<400> SEQUENCE: 390
nncngaaaac ncnncaang                                                  19
```

```
<210> SEQ ID NO 391
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 3, 8, 13, 15, 19
<223> OTHER INFORMATION: n = T or U

<400> SEQUENCE: 391
cnnagcanaa agnancagn                                                19

<210> SEQ ID NO 392
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 9, 12, 15, 16
<223> OTHER INFORMATION: n = T or U

<400> SEQUENCE: 392
caaaaaagna cngcnnagc                                                19

<210> SEQ ID NO 393
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 6, 12, 13, 15, 18, 19
<223> OTHER INFORMATION: n = T or U

<400> SEQUENCE: 393
caaganaaaa cnngnccnn                                                19

<210> SEQ ID NO 394
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 3, 7, 10, 12, 13, 15
<223> OTHER INFORMATION: n = T or U

<400> SEQUENCE: 394
nancagncan gnngnaaac                                                19

<210> SEQ ID NO 395
<211> LENGTH: 19
<212> TYPE: DNA
<213> ORGANISM: Artificial Sequence
<220> FEATURE:
```

```
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 6, 11, 13, 14, 17
<223> OTHER INFORMATION: n = T or U

<400> SEQUENCE: 395
cnaaanaacc ngnncanca                                                19

<210> SEQ ID NO 396
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 8, 9, 10, 11, 12, 17
<223> OTHER INFORMATION: n = T or U

<400> SEQUENCE: 396
agcacacnnn nnacacngc                                                19

<210> SEQ ID NO 397
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 6, 8, 9, 11, 12, 14, 15, 18
<223> OTHER INFORMATION: n = T or U

<400> SEQUENCE: 397
accacnanna nncnnganc                                                19

<210> SEQ ID NO 398
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 3, 5, 6, 7, 9, 10, 11, 15, 16, 17
<223> OTHER INFORMATION: n = T or U

<400> SEQUENCE: 398
ngnannngnn nccannncc                                                19

<210> SEQ ID NO 399
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 5, 10, 12, 14, 16, 17, 18
<223> OTHER INFORMATION: n = T or U
```

```
<400> SEQUENCE: 399 acngnaaaacn cnancnnng                                              19

<210> SEQ ID NO 400
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 3, 7, 12, 16, 17
<223> OTHER INFORMATION: n = T or U

<400> SEQUENCE: 400
cnnaagnggg cnaaannac                                               19

<210> SEQ ID NO 401
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 4, 7, 9, 12, 18
<223> OTHER INFORMATION: n = T or U

<400> SEQUENCE: 401
ccnncanang gncacacna                                               19

<210> SEQ ID NO 402
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 4, 11, 13
<223> OTHER INFORMATION: n = T or U

<400> SEQUENCE: 402
ggnnacaagc nangaagcc                                               19

<210> SEQ ID NO 403
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 10, 12, 17
<223> OTHER INFORMATION: n = T or U

<400> SEQUENCE: 403
cnaagcaacn anagaanac                                               19

<210> SEQ ID NO 404
```

```
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 4, 5, 8, 9, 10, 11, 12
<223> OTHER INFORMATION: n = T or U

<400> SEQUENCE: 404
nccnngannn nncacagag                                                19

<210> SEQ ID NO 405
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 5, 9, 10, 18
<223> OTHER INFORMATION: n = T or U

<400> SEQUENCE: 405
anacnaacnn aaagcccng                                                19

<210> SEQ ID NO 406
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 4, 5, 7, 10, 14, 16, 17, 18
<223> OTHER INFORMATION: n = T or U

<400> SEQUENCE: 406
gggnngnagn aacncnnnc                                                19

<210> SEQ ID NO 407
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 12, 14, 15, 16
<223> OTHER INFORMATION: n = T or U

<400> SEQUENCE: 407
nagaacacaa cncnnnggg                                                19

<210> SEQ ID NO 408
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
```

```
<220> FEATURE:
<221> NAME/KEY: misc_feature
<222> LOCATION: 2, 4, 8, 9, 10, 17
<223> OTHER INFORMATION: n = T or U

<400> SEQUENCE: 408
cncngaannn ccaaganac                                              19

<210> SEQ ID NO 409
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 2, 3, 6, 10, 11, 12, 14, 16
<223> OTHER INFORMATION: n = T or U

<400> SEQUENCE: 409
nnnacnggan nnancncag                                              19

<210> SEQ ID NO 410
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 5, 9, 15, 18
<223> OTHER INFORMATION: n = T or U

<400> SEQUENCE: 410
ngagnaggng acagngcng                                              19

<210> SEQ ID NO 411
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 9, 10, 11, 12, 14, 18
<223> OTHER INFORMATION: n = T or U

<400> SEQUENCE: 411
ggaggcagnn nngngcang                                              19

<210> SEQ ID NO 412
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 4, 6, 7, 11, 12, 14, 17, 19
<223> OTHER INFORMATION: n = T or U

<400> SEQUENCE: 412
```
cnancnncca nnanacncn                                              19

<210> SEQ ID NO 413
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 2, 4, 5, 6, 8, 9, 12, 14, 15, 16, 18
<223> OTHER INFORMATION: n = T or U

<400> SEQUENCE: 413
nngnnngnng cngnnngnc                                              19

<210> SEQ ID NO 414
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 4, 5, 6, 8
<223> OTHER INFORMATION: n = T or U

<400> SEQUENCE: 414
nccnnncnga gacaggcac                                              19

<210> SEQ ID NO 415
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 18
<223> OTHER INFORMATION: n = T or U

<400> SEQUENCE: 415
accagcacga gcaagacnc                                              19

<210> SEQ ID NO 416
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 4, 5, 7, 10, 11
<223> OTHER INFORMATION: n = T or U

<400> SEQUENCE: 416
accnngncan ncacaccag                                              19

<210> SEQ ID NO 417
<211> LENGTH: 19
<212> TYPE: DNA
<213> ORGANISM: Artificial Sequence

```
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 6, 7, 9, 16
<223> OTHER INFORMATION: n = T or U

<400> SEQUENCE: 417
nccagnnanc cagcancag                                                19

<210> SEQ ID NO 418
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 4, 5, 6, 10, 16, 18
<223> OTHER INFORMATION: n = T or U

<400> SEQUENCE: 418
gcnnnngaan aggacngnc                                                19

<210> SEQ ID NO 419
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 5, 7, 9, 10, 15, 18
<223> OTHER INFORMATION: n = T or U

<400> SEQUENCE: 419
gagangncnn caacngcnc                                                19

<210> SEQ ID NO 420
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 5, 6, 9, 12, 16
<223> OTHER INFORMATION: n = T or U

<400> SEQUENCE: 420
ggggnnagnc cncgangaa                                                19

<210> SEQ ID NO 421
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 4, 5, 9, 13, 15
```

```
<223> OTHER INFORMATION: n = T or U

<400> SEQUENCE: 421
ncanngcana acngnaggg                                          19

<210> SEQ ID NO 422
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 5, 6, 12, 13, 15, 18
<223> OTHER INFORMATION: n = T or U

<400> SEQUENCE: 422
gcncnngcca anncngang                                          19

<210> SEQ ID NO 423
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 5, 7, 9, 15, 18
<223> OTHER INFORMATION: n = T or U

<400> SEQUENCE: 423
acccnancnc caggnccna                                          19

<210> SEQ ID NO 424
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 16
<223> OTHER INFORMATION: n = T or U

<400> SEQUENCE: 424
acaggcaaag caggcnacc                                          19

<210> SEQ ID NO 425
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 3, 5, 10, 15, 18
<223> OTHER INFORMATION: n = T or U

<400> SEQUENCE: 425
gnncngacan agcancanc                                          19
```

```
<210> SEQ ID NO 426
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 8, 9, 10, 12, 19
<223> OTHER INFORMATION: n = T or U

<400> SEQUENCE: 426
cncagagnnn cnagagaan                                                    19

<210> SEQ ID NO 427
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 4, 5, 7, 10, 11, 17
<223> OTHER INFORMATION: n = T or U

<400> SEQUENCE: 427
angnncncan ncgagcngc                                                    19

<210> SEQ ID NO 428
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 6, 14, 18
<223> OTHER INFORMATION: n = T or U

<400> SEQUENCE: 428
ngaacnggaa cacnagang                                                    19

<210> SEQ ID NO 429
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 9, 14
<223> OTHER INFORMATION: n = T or U

<400> SEQUENCE: 429
gcncaggcng aacnggaac                                                    19

<210> SEQ ID NO 430
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
```

```
        deoxyribonucleotide, or nucleotide analog
<220> FEATURE:
<221> NAME/KEY: misc_feature
<222> LOCATION: 1, 2, 7, 10, 13, 14
<223> OTHER INFORMATION: n = T or U

<400> SEQUENCE: 430
nngacancan canngcgac                                                    19

<210> SEQ ID NO 431
<211> LENGTH: 19
<212> TYPE: DNA
<213> ORGANISM: Artificial Sequence
<220> FEATURE:
<223> OTHER INFORMATION: based on Homo sapiens.
        Each nucleobase may be part of a ribonucleotide,
        deoxyribonucleotide, or nucleotide analog
<220> FEATURE:
<221> NAME/KEY: misc_feature
<222> LOCATION: 5, 19
<223> OTHER INFORMATION: n = T or U

<400> SEQUENCE: 431
accancacaa caaaagcan                                                    19

<210> SEQ ID NO 432
<211> LENGTH: 19
<212> TYPE: DNA
<213> ORGANISM: Artificial Sequence
<220> FEATURE:
<223> OTHER INFORMATION: based on Homo sapiens.
        Each nucleobase may be part of a ribonucleotide,
        deoxyribonucleotide, or nucleotide analog
<220> FEATURE:
<221> NAME/KEY: misc_feature
<222> LOCATION: 5, 6, 11, 13, 14, 16
<223> OTHER INFORMATION: n = T or U

<400> SEQUENCE: 432
ccacnnggca ngnncnacc                                                    19

<210> SEQ ID NO 433
<211> LENGTH: 19
<212> TYPE: DNA
<213> ORGANISM: Artificial Sequence
<220> FEATURE:
<223> OTHER INFORMATION: based on Homo sapiens.
        Each nucleobase may be part of a ribonucleotide,
        deoxyribonucleotide, or nucleotide analog
<220> FEATURE:
<221> NAME/KEY: misc_feature
<222> LOCATION: 1, 4, 6, 14
<223> OTHER INFORMATION: n = T or U

<400> SEQUENCE: 433
ncgnancaag aacncacac                                                    19

<210> SEQ ID NO 434
<211> LENGTH: 19
<212> TYPE: DNA
<213> ORGANISM: Artificial Sequence
<220> FEATURE:
<223> OTHER INFORMATION: based on Homo sapiens.
        Each nucleobase may be part of a ribonucleotide,
        deoxyribonucleotide, or nucleotide analog
<220> FEATURE:
<221> NAME/KEY: misc_feature
<222> LOCATION: 3, 5, 7, 12, 13
<223> OTHER INFORMATION: n = T or U

<400> SEQUENCE: 434
```
ggnancngaa gnngacaac                                              19

<210> SEQ ID NO 435
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 2, 3, 5, 6, 8, 13, 16, 18
<223> OTHER INFORMATION: n = T or U

<400> SEQUENCE: 435
nnncnncncc agnggnanc                                              19

<210> SEQ ID NO 436
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 2, 4, 10, 17
<223> OTHER INFORMATION: n = T or U

<400> SEQUENCE: 436
nncnccaggn ccaaaanga                                              19

<210> SEQ ID NO 437
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 7, 9, 10, 12
<223> OTHER INFORMATION: n = T or U

<400> SEQUENCE: 437
acagcancnn cngaagaac                                              19

<210> SEQ ID NO 438
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 7, 9, 11, 12, 15, 18
<223> OTHER INFORMATION: n = T or U

<400> SEQUENCE: 438
cacaggngna nncancang                                              19

<210> SEQ ID NO 439
<211> LENGTH: 19
<212> TYPE: DNA

```
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 6, 8, 10, 12, 13
<223> OTHER INFORMATION: n = T or U

<400> SEQUENCE: 439
ccaggncncn annaaagcc                                              19

<210> SEQ ID NO 440
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 2, 4, 6, 11, 12, 14
<223> OTHER INFORMATION: n = T or U

<400> SEQUENCE: 440
nncncnccag nngncagga                                              19

<210> SEQ ID NO 441
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 5, 8, 16, 18
<223> OTHER INFORMATION: n = T or U

<400> SEQUENCE: 441
gaagngcnga cacaananc                                              19

<210> SEQ ID NO 442
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 1, 2, 3, 4, 7, 8, 10, 13, 16, 18
<223> OTHER INFORMATION: n = T or U

<400> SEQUENCE: 442
nnnnccnncn ccnccncnc                                              19

<210> SEQ ID NO 443
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
```

<222> LOCATION: 3, 5, 8, 13, 14, 15, 17, 18
<223> OTHER INFORMATION: n = T or U

<400> SEQUENCE: 443
cancngangc cannncnnc                                                    19

<210> SEQ ID NO 444
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 6, 7, 9, 11, 12, 14, 15
<223> OTHER INFORMATION: n = T or U

<400> SEQUENCE: 444
agccanncng nncnnccga                                                    19

<210> SEQ ID NO 445
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 7
<223> OTHER INFORMATION: n = T or U

<400> SEQUENCE: 445
ccagganagg aagcacaca                                                    19

<210> SEQ ID NO 446
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 5, 7, 11, 15, 16, 18
<223> OTHER INFORMATION: n = T or U

<400> SEQUENCE: 446
anggnancaa ncagnncnc                                                    19

<210> SEQ ID NO 447
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 9, 10, 11, 14, 15, 16
<223> OTHER INFORMATION: n = T or U

<400> SEQUENCE: 447
ccgcagcann nccnnnaac                                                    19

<210> SEQ ID NO 448
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 4, 5, 6, 7, 8, 14, 16, 17
<223> OTHER INFORMATION: n = T or U

<400> SEQUENCE: 448
cagnnnnnga agangnngg                                          19

<210> SEQ ID NO 449
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 11, 18
<223> OTHER INFORMATION: n = T or U

<400> SEQUENCE: 449
gngacagacc ngaaacanc                                          19

<210> SEQ ID NO 450
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 6, 7, 8, 9, 11, 12
<223> OTHER INFORMATION: n = T or U

<400> SEQUENCE: 450
gggcannnnc nnagagaag                                          19

<210> SEQ ID NO 451
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 3, 8, 9, 12, 13, 15
<223> OTHER INFORMATION: n = T or U

<400> SEQUENCE: 451
agnacccnng annanaccc                                          19

<210> SEQ ID NO 452
<211> LENGTH: 19
<212> TYPE: DNA
<213> ORGANISM: Artificial Sequence
<220> FEATURE:
<223> OTHER INFORMATION: based on Homo sapiens.

```
        Each nucleobase may be part of a ribonucleotide,
        deoxyribonucleotide, or nucleotide analog
<220> FEATURE:
<221> NAME/KEY: misc_feature
<222> LOCATION: 5, 7, 16
<223> OTHER INFORMATION: n = T or U

<400> SEQUENCE: 452
gaaangnacg aacagnacc                                                 19

<210> SEQ ID NO 453
<211> LENGTH: 19
<212> TYPE: DNA
<213> ORGANISM: Artificial Sequence
<220> FEATURE:
<223> OTHER INFORMATION: based on Homo sapiens.
        Each nucleobase may be part of a ribonucleotide,
        deoxyribonucleotide, or nucleotide analog
<220> FEATURE:
<221> NAME/KEY: misc_feature
<222> LOCATION: 1, 9, 12, 15, 16
<223> OTHER INFORMATION: n = T or U

<400> SEQUENCE: 453
ngaaaaacnc anaannccc                                                 19

<210> SEQ ID NO 454
<211> LENGTH: 19
<212> TYPE: DNA
<213> ORGANISM: Artificial Sequence
<220> FEATURE:
<223> OTHER INFORMATION: based on Homo sapiens.
        Each nucleobase may be part of a ribonucleotide,
        deoxyribonucleotide, or nucleotide analog
<220> FEATURE:
<221> NAME/KEY: misc_feature
<222> LOCATION: 4, 6, 7, 8, 9
<223> OTHER INFORMATION: n = T or U

<400> SEQUENCE: 454
ccancnnnnc agaaacaag                                                 19

<210> SEQ ID NO 455
<211> LENGTH: 19
<212> TYPE: DNA
<213> ORGANISM: Artificial Sequence
<220> FEATURE:
<223> OTHER INFORMATION: based on Homo sapiens.
        Each nucleobase may be part of a ribonucleotide,
        deoxyribonucleotide, or nucleotide analog
<220> FEATURE:
<221> NAME/KEY: misc_feature
<222> LOCATION: 2, 4, 7, 8, 10, 12, 17, 18
<223> OTHER INFORMATION: n = T or U

<400> SEQUENCE: 455
cnanaanncn cnccagnng                                                 19

<210> SEQ ID NO 456
<211> LENGTH: 19
<212> TYPE: DNA
<213> ORGANISM: Artificial Sequence
<220> FEATURE:
<223> OTHER INFORMATION: based on Homo sapiens.
        Each nucleobase may be part of a ribonucleotide,
        deoxyribonucleotide, or nucleotide analog
<220> FEATURE:
<221> NAME/KEY: misc_feature
<222> LOCATION: 2, 6, 7, 11, 17
<223> OTHER INFORMATION: n = T or U
```

```
<400> SEQUENCE: 456
cncccnnagg nacacanac                                                    19

<210> SEQ ID NO 457
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 9, 15, 18
<223> OTHER INFORMATION: n = T or U

<400> SEQUENCE: 457
acaagcagng acacnacnc                                                    19

<210> SEQ ID NO 458
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 2, 6, 9, 14, 17
<223> OTHER INFORMATION: n = T or U

<400> SEQUENCE: 458
gnaacnccng aaangangc                                                    19

<210> SEQ ID NO 459
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 8, 13, 17
<223> OTHER INFORMATION: n = T or U

<400> SEQUENCE: 459
caacaaancc agnaacncc                                                    19

<210> SEQ ID NO 460
<211> LENGTH: 19
<212> TYPE: DNA
<213> ORGANISM: Artificial Sequence
<220> FEATURE:
<223> OTHER INFORMATION: based on Homo sapiens.
      Each nucleobase may be part of a ribonucleotide,
      deoxyribonucleotide, or nucleotide analog
<220> FEATURE:
<221> NAME/KEY: misc_feature
<222> LOCATION: 6, 10, 12, 15
<223> OTHER INFORMATION: n = T or U

<400> SEQUENCE: 460
caccanaacn cngangaac                                                    19
```

ANTISENSE IAP NUCLEOBASE OLIGOMERS AND USES THEREOF

CROSS-REFERENCE TO RELATED APPLICATIONS

This application is a continuation of U.S. patent application Ser. No. 10/400,382 filed Mar. 27, 2003, now U.S. Pat. No. 7,091,333, which claims benefit from U.S. provisional application 60/367,853 filed Mar. 27, 2002.

BACKGROUND OF THE INVENTION

The invention relates to anti sense IAP nucleobase oligomers and methods of using them to induce apoptosis.

One way by which cells die is referred to as apoptosis, or programmed cell death. Apoptosis often occurs as a normal part of the development and maintenance of healthy tissues. The process may occur so rapidly that it is difficult to detect.

The apoptosis pathway is now known to play a critical role in embryonic development, viral pathogenesis, cancer, autoimmune disorders, and neurodegenerative diseases, as well as other events. The failure of an apoptotic response has been implicated in the development of cancer, autoimmune disorders, such as lupus erythematosis and multiple sclerosis, and in viral infections, including those associated with herpes virus, poxvirus, and adenovirus.

The importance of apoptosis in cancer has become clear in recent years. The identification of growth promoting oncogenes in the late 1970's gave rise to an almost universal focus on cellular proliferation that dominated research in cancer biology for many years. Long-standing dogma held that anti-cancer therapies preferentially targeted rapidly dividing cancer cells relative to "normal" cells. This explanation was not entirely satisfactory, since some slow growing tumors are easily treated, while many rapidly dividing tumor types are extremely resistant to anti-cancer therapies. Progress in the cancer field has now led to a new paradigm in cancer biology wherein neoplasia is viewed as a failure to execute normal pathways of programmed cell death. Normal cells receive continuous feedback from their neighbors through various growth factors, and commit "suicide" if removed from this context. Cancer cells somehow bypass these commands and continue inappropriate proliferation. It is now believed that many cancer therapies, including radiation and many chemotherapies, previously thought to act by causing cellular injury, actually work by triggering apoptosis.

Both normal cell types and cancer cell types display a wide range of susceptibility to apoptotic triggers, although the determinants of this resistance are only now under investigation. Many normal cell types undergo temporary growth arrest in response to a sub-lethal dose of radiation or cytotoxic chemical, while cancer cells in the vicinity undergo apoptosis. This differential effect at a given dose provides the crucial treatment window that allows successful anti-cancer therapy. It is therefore not surprising that resistance of tumor cells to apoptosis is emerging as a major category of cancer treatment failure.

Several potent endogenous proteins that inhibit apoptosis have been identified, including Bcl-2, and IAP (inhibitor-of apoptosis) families in mammalian cells. Certain members of the latter family directly inhibit terminal effector caspases, i.e. casp-3 and casp-7, engaged in the execution of cell death, as well as the key mitochondrial initiator caspase, casp-9, important to the mediation of cancer chemotherapy induced cell death. The IAPs are the only known endogenous caspase inhibitors, and thus play a central role in the regulation of apoptosis.

The IAPs have been postulated to contribute to the development of some cancers, and a postulated causal chromosomal translocation involving one particular IAP (cIAP2/HIAP1) has been identified in MALT lymphoma. A recent correlation between elevated XIAP, poor prognosis, and short survival has been demonstrated in patients with acute myelogenous leukemia. XIAP was highly over-expressed in many tumor cell lines of the NCI panel.

There exists a need for improved cancer therapeutics and, in particular, therapeutics that can induce cancer cells to undergo apoptosis and override anti-apoptotic signals provided in such cells.

SUMMARY OF THE INVENTION

In general, the invention features methods and reagents useful for inducing apoptosis in a cell. The methods and reagents of the invention are useful in treating cancers, and other proliferative diseases.

The present invention features nucleobase oligomers, particularly oligonucleotides, for use in modulating the function of a polynucleotide encoding an IAP. These oligomers reduce the amount of an IAP produced, allowing a cell normally expressing the IAP to undergo apoptosis. This is accomplished by providing nucleobase oligomers that specifically hybridize with one or more polynucleotides encoding an IAP. The specific hybridization of the nucleobase oligomer with an IAP polynucleotide (e.g., RNA, DNA) interferes with the normal function of that IAP polynucleotide, reducing the amount of IAP protein produced. This modulation of function of a target nucleic acid by compounds that specifically hybridize to the target is generally referred to as "antisense."

In one aspect, the invention features a nucleobase oligomer of up to 30 nucleobases in length, the oligomer including at least eight consecutive nucleobases of a sequence selected from SEQ ID NOs: 1-99, 143, 147, 151, 163-260, 287, 289, and 300-460. Desirably, when administered to a cell, the oligomer inhibits expression of an IAP.

In certain embodiments, the nucleobase oligomer includes a sequence selected from SEQ ID NOs: 1-99, 143, 147, 151, 163-260, 287, 289, and 300-460. It is desirable that the nucleobase oligomer consists of (or essentially of) one or more of the foregoing SEQ ID NOs. For example, the nucleobase oligomer may be a XIAP antisense nucleic acid that includes a sequence chosen from SEQ ID NOs 97, 98, 99, 143, 147, 151, 287, and 289, a HIAP1 antisense nucleic acid that includes a sequence chosen from SEQ ID NOs 300-389, or a HIAP2 antisense nucleic acid includes a sequence chosen from SEQ ID NOs 390-460. In a particularly desirable embodiment, the invention features a nucleobase oligomer having eleven DNA residues flanked on each side by four 2'-O-methyl RNA residues, and consists of one of the following sequences: 5'-AUUGGTTC CAATGTGUUCU-3' (SEQ ID NO: 155); 5'-ACACGACCGCTAAGAAACA-3' (SEQ ID NO: 16); 5'-ACAGGACTACCACTTGGAA-3' (SEQ ID NO: 157); 5'-UGCCAGTGTTGATGCUGAA-3' (SEQ ID NO: 27); 5'-GCUGAGTCTCCATATUGCC-3' (SEQ ID NO: 141); 5'-UCGGGTATATGGTGTCUGA-3' (SEQ. ID NO: 41); 5'-AAGCACTGCACTTGGUCAC-3' (SEQ ID NO: 47); 5'-CCGGCCCAAAACAAAGAAG-3' (SEQ ID NO: 51); 5'-ACCCTGGATACCATTUAGC-3' (SEQ ID NO: 63); 5'-UGUCAGTACATGTTGGCUC-3' (SEQ ID NO: 161); and 5'-UGCACCCTGGATA CCAUUU-3' (SEQ ID NO: 151).

A nucleobase oligomer of the present invention may include at least one modified linkage (e.g., a phosphorothioate, a methylphosphonate, a phosphotriester, a phosphorodithioate, or a phosphoselenate linkage), modified nucleobase (e.g., a 5-methyl cytosine), and/or a modified sugar moiety (e.g., a 2'-O-methoxyethyl group or a 2'-O-methyl group). In one embodiment, the oligomer is a chimeric oligomer (e.g., an oligonucleotide that includes DNA residues linked together by phosphorothioate or phosphodiester linkages, flanked on each side by at least one, two, three, or four 2'-O-methyl RNA residue linked together by a phosphorothioate linkage).

In another aspect, the invention features a method of enhancing apoptosis in a cell. This method includes the step of administering to the cell a nucleobase oligomer of the present invention so that expression of an IAP (e.g., XIAP, HIAP1, or HIAP2) is inhibited. The nucleobase oligomer may be, e.g., a component of an antisense compound, a double-stranded RNA, or a ribozyme. This administering step may be performed alone, or in combination with a second step (e.g., administration of a chemotherapeutic agent, a biological response modifying agent, and/or a chemosensitizer). The cell can be in vitro or in vivo. In one embodiment, the cell is a cancer cell (e.g., a human cancer cell) or a cell of lymphoid or myeloid origin.

In a related aspect, the invention features a method for treating an animal (e.g., a human) having a proliferative disease (e.g., a cancer, lymphoproliferative disorder, or myelodysplastic syndrome) or preventing the development of such a disease, by administering to the animal an effective amount of a nucleobase oligomer of the present invention.

The cancer may be, for example, acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, myelodysplastic syndrome, chronic lymphocytic leukemia, polycythemia vera, lymphoma, Hodgkin's disease, Waldenstrom's macroglubulinemia, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, or retinoblastoma. When treating a cancer, it may be desirable to also administer one or more chemotherapeutic agents, biological response modifying agents, and/or chemosensitizers. Desirably, the administration of one or more of these agents is within five days of the administration of the nucleobase oligomer. Exemplary chemotherapeutic agents are adriamycin (doxorubicin), vinorelbine, etoposide, taxol, and cisplatin. While any route of administration that results in an effective amount at the desired site may be used, particularly desirable routes are by intravenous and intratumoral administration.

In another aspect, the invention features a pharmaceutical composition that includes a nucleobase oligomer of the present invention and a pharmaceutically acceptable carrier. If desirable, the pharmaceutical composition may further include additional components (e.g., a colloidal dispersion system or a chemotherapeutic agent).

The invention also features a catalytic RNA molecule capable of cleaving XIAP, HIAP1, or HIAP2 mRNA. In desirable embodiments, the catalytic RNA molecule includes, in its binding arms, at least eight consecutive nucleobases corresponding to a nucleobase oligomer of the invention (e.g., a nucleobase sequence of any one of Tables 1, 2, 6, and 7). The RNA molecule is desirably in a hammerhead motif, but may also be in a hairpin, hepatitis delta virus, group 1 intron, VS RNA or RNAseP RNA motif.

The invention also features an expression vector including a nucleic acid encoding one or more catalytic RNA molecules of the invention positioned for expression in a mammalian cell.

The invention also features a method of treating an animal having a cancer or lymphoproliferative disorder by administering to the animal an effective amount of a catalytic RNA molecule described above, or an expression vector encoding such a catalytic RNA molecule.

In still another aspect, the invention features a double-stranded RNA molecule having between 21 and 29 nucleobases, wherein at least eight consecutive nucleobases corresponding to a sequence of any one of Tables 1, 2, 6, and 7 are present.

In a related aspect, the invention also features a double-stranded RNA molecule having between 50 and 70 nucleobases, the RNA molecule having a first domain of between 21 and 29 nucleobases that include least eight consecutive nucleobases corresponding to a sequence of any one of Tables 1, 2, 6, and 7; a second domain complementary to the first domain, and a loop domain situated between the first and second domains such that the first and second domains are capable of duplexing to form a double-stranded RNA molecule. The invention also features an expression vector (e.g., an adenoviral vector or a retroviral vector) encoding such a double stranded RNA.

The invention also features a method of treating an animal having a cancer or lymphoproliferative disorder by administering to the animal an effective amount of a double-stranded RNA molecule described above By a "nucleobase oligomer" is meant a compound that includes a chain of at least eight nucleobases joined together by linkage groups. Included in this definition are natural and non-natural oligonucleotides, both modified and unmodified, as well as oligonucleotide mimetics such as Protein Nucleic Acids, locked nucleic acids, and arabinonucleic acids. Numerous nucleobases and linkage groups may be employed in the nucleobase oligomers of the invention, including those described in detail herein in the section entitled "Oligonucleotides and other nucleobase oligomers," infra.

"Protein" or "polypeptide" or "polypeptide fragment" means any chain of more than two amino acids, regardless of post-translational modification (e.g., glycosylation or phosphorylation), constituting all or part of a naturally occurring polypeptide or peptide, or constituting a non-naturally occurring polypeptide or peptide.

"Apoptosis" means the process of cell death wherein a dying cell displays a set of well-characterized biochemical hallmarks that include cell membrane blebbing, cell soma shrinkage, chromatin condensation, and DNA laddering. Cells that die by apoptosis include neurons (e.g., during the course of neurodegenerative diseases such as stroke, Parkinson's disease, and Alzheimer's disease), cardiomyocytes (e.g., after myocardial infarction or over the course of congestive heart failure), and cancer cells (e.g., after exposure to radiation or chemotherapeutic agents). Environmental stress (e.g., hypoxic stress) that is not alleviated may cause a cell to enter the early phase of the apoptotic pathway, which is reversible (i.e., cells at the early stage of the apoptotic pathway can be rescued). At a later phase of apoptosis (the commitment phase), cells cannot be rescued, and, as a result, are committed to die.

Proteins and compounds known to stimulate and inhibit apoptosis in a diverse variety of cells are well known in the art. For example, intracellular expression and activation of the caspase (ICE) family induces or stimulates apoptotic cell death, whereas expression of the IAPs or some members of the Bcl-2 family inhibit apoptotic cell death. In addition, there are survival factors that inhibit cell death in specific cell types. For example, neurotrophic factors, such as NGF inhibit neuronal apoptosis.

By "IAP gene" is meant a gene encoding a polypeptide having at least one BIR domain and that is capable of modulating (inhibiting or enhancing) apoptosis in a cell or tissue when provided by other intracellular or extracellular delivery methods (see, e.g., U.S. Pat. No. 5,919,912). In preferred embodiments, the IAP gene is a gene having about 50% or greater nucleotide sequence identity (e.g., at least 85%, 90%, or 95%) to at least one of human or murine XIAP, HIAP1, or HIAP2 (each of which is described in U.S. Pat. No. 6,156,535). Preferably the region of sequence over which identity is measured is a region encoding at least one BIR domain and a ring zinc finger domain. Mammalian IAP genes include nucleotide sequences isolated from any mammalian source. Preferably the mammal is a human.

By "IAP protein" or "IAP polypeptide" is meant a polypeptide, or fragment thereof, encoded by an IAP gene.

By "IAP biological activity" is meant any activity known to be caused in vivo or in vitro by an IAP polypeptide.

By "enhancing apoptosis" is meant increasing the number of cells that apoptose in a given cell population (e.g., cancer cells, lymphocytes, fibroblasts, or any other cells). It will be appreciated that the degree of apoptosis enhancement provided by an apoptosis-enhancing compound in a given assay will vary, but that one skilled in the art can determine the statistically significant change in the level of apoptosis that identifies a nucleobase oligomer that enhances apoptosis otherwise limited by an IAP. Preferably, "enhancing apoptosis" means that the increase in the number of cells undergoing apoptosis is at least 10%, more preferably the increase is 25% or even 50%, and most preferably the increase is at least one-fold, relative to cells not administered a nucleobase oligomer of the invention but otherwise treated in a substantially similar manner. Preferably the sample monitored is a sample of cells that normally undergo insufficient apoptosis (i.e., cancer cells). Methods for detecting changes in the level of apoptosis (i.e., enhancement or reduction) are described herein.

By a nucleobase oligomer that "inhibits the expression" of a target gene (e.g., an IAP) is meant one that reduces the amount of a target mRNA, or protein encoded by such mRNA, by at least about 5%, more desirable by at least about 10%, 25%, or even 50%, relative to an untreated control. Methods for measuring both mRNA and protein levels are well-known in the art; exemplary methods are described herein.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "proliferative disease" is meant a disease that is caused by or results in inappropriately high levels of cell division, inappropriately low levels of apoptosis, or both. For example, cancer is an example of a proliferative disease. Examples of cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma). Lymphoproliferative disorders are also considered to be proliferative diseases.

Preferably, a nucleobase oligomer of the invention is capable of enhancing apoptosis and/or decreasing IAP mRNA or protein levels when present in a cell that normally does not undergo sufficient apoptosis. Preferably the increase is by at least 10%, relative to a control, more preferably 25%, and most preferably 1-fold or more. Preferably a nucleobase oligomer of the invention includes from about 8 to 30 nucleobases, wherein at least eight consecutive nucleobases are from a sequence selected from SEQ ID NOs: 1-99, 143, 147, 151, 163-260, 287, 289, and 300-460. A nucleobase oligomer of the invention may also contain, e.g., an additional 20, 40, 60, 85, 120, or more consecutive nucleobases that are complementary to an IAP polynucleotide. The nucleobase oligomer (or a portion thereof) may contain a modified backbone. Phosphorothioate, phosphorodithioate, and other modified backbones are known in the art. The nucleobase oligomer may also contain one or more non-natural linkages.

By "chemotherapeutic agent" is meant an agent that is used to kill cancer cells or to slow their growth. Accordingly, both cytotoxic and cytostatic agents are considered to be chemotherapeutic agents.

By "biological response modifying agent" is meant an agent that stimulates or restores the ability of the immune system to fight disease. Some, but not all, biological response modifying agents may slow the growth of cancer cells and thus are also considered to be chemotherapeutic agents." Examples of biological response modifying agents are interferons (alpha, beta, gamma), interleukin-2, rituximab, and trastuzumab.

By "chemosensitizer" is meant an agent that makes tumor cells more sensitive to the effects of chemotherapy.

By "an effective amount" is meant the amount of a compound (e.g., a nucleobase oligomer) required to ameliorate the symptoms of a disease, inhibit the growth of the target cells, reduce the size or number of tumors, inhibit the expression of an IAP, or enhance apoptosis of target cells, relative to an untreated patient. The effective amount of active compound(s) used to practice the present invention for therapeutic treatment of abnormal proliferation (i.e., cancer) varies depending upon the manner of administration, the age, body weight, and general health of the subject. Ultimately, the attending physician or veterinarian will decide the appropriate amount and dosage regimen. Such amount is referred to as an "effective" amount.

By "lymphoproliferative disorder" is meant a disorder in which there is abnormal proliferation of cells of the lymphatic system (e.g., T-cells and B-cells), and includes multiple sclerosis, Crohn's disease, lupus erythematosus, rheumatoid arthritis, and osteoarthritis.

By "ribozyme" is meant an RNA that has enzymatic activity, possessing site specificity and cleavage capability for a target RNA molecule. Ribozymes can be used to decrease expression of a polypeptide. Methods for using ribozymes to decrease polypeptide expression are described, for example, by Turner et al., (Adv. Exp. Med. Biol. 465:303-318, 2000) and Norris et al., (Adv. Exp. Med. Biol. 465:293-301, 2000).

By "reporter gene" is meant a gene encoding a polypeptide whose expression may be assayed; such polypeptides include, without limitation, glucuronidase (GUS), luciferase, chloramphenicol transacetylase (CAT), and beta-galactosidase.

By "promoter" is meant a polynucleotide sufficient to direct transcription.

By "operably linked" is meant that a first polynucleotide is positioned adjacent to a second polynucleotide that directs transcription of the first polynucleotide when appropriate molecules (e.g., transcriptional activator proteins) are bound to the second polynucleotide.

Other features and advantages of the invention will be apparent from the following description of the preferred embodiments thereof, and from the claims.

BRIEF DESCRIPTION OF THE DRAWINGS

FIGS. 1A-1L are graphs showing the effect of antisense XIAP oligonucleotides on XIAP protein expression, relative to total protein (FIGS. 1A, 1C, 1E, 1G, 1I, and 1K). FIGS. 1B, 1D, 1F, 1H, 1J, and 1L are the total protein concentration values for each oligonucleotide transfection compared to mock transfection results that were used to normalize the above XIAP protein results.

FIGS. 2A-2C are graphs showing the effects of various antisense XIAP oligonucleotides, alone or in combination, on XIAP RNA (FIG. 2A) and protein (FIG. 2B). FIG. 2C is a graph of the total protein concentration values for each oligonucleotide transfection compared to mock transfection results, which were used to normalize the XIAP protein results shown in FIG. 2B.

FIG. 12A shows the percentage of cells having sub-G0/G1 (apoptotic) DNA content, as measured by propidium iodide (PI) staining and flow cytometry. FIG. 12B shows nuclear morphology of oligonucleotide-treated H460 cells stained with DAPI. Arrows indicate cells that have characteristic apoptotic morphology of nuclear DNA condensation or fragmentation.

FIG. 19A depicts tumor sections stained with hematoxylin and eosin. FIG. 19B shows immunohistochemistry of ubiquitin expression in tumor sections. Representative tumor photomicrographs are shown. Internal scale markers equal 100 µm.

FIG. 20A depicts antitumor activity of single agents, while FIG. 20B depicts antitumor activity of VNB and G4 oligonucleotides in combination. All data are expressed as means±SEM (n=6 mice/group).

DETAILED DESCRIPTION OF THE INVENTION

Figure 1A:
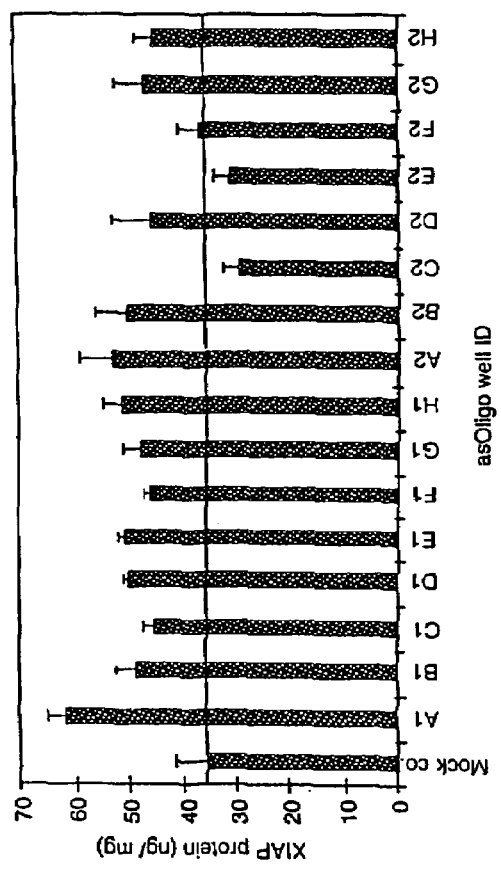
Figure 1B:
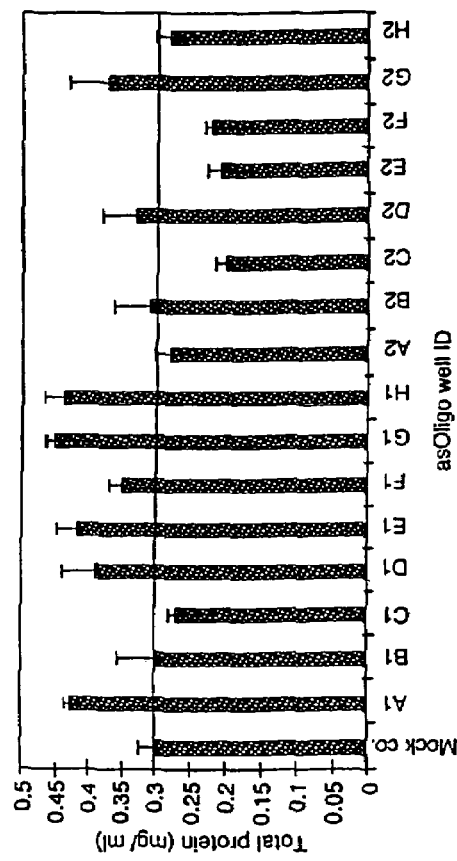
Figure 1C:
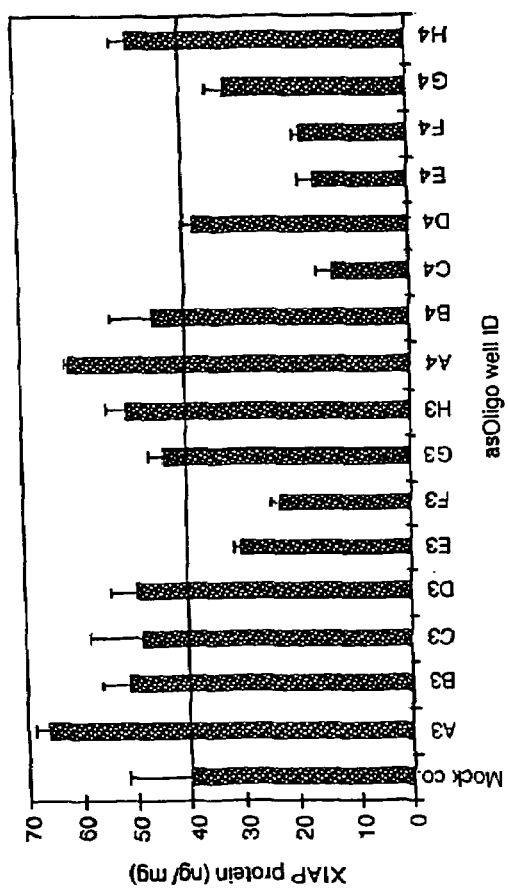
Figure 1D:
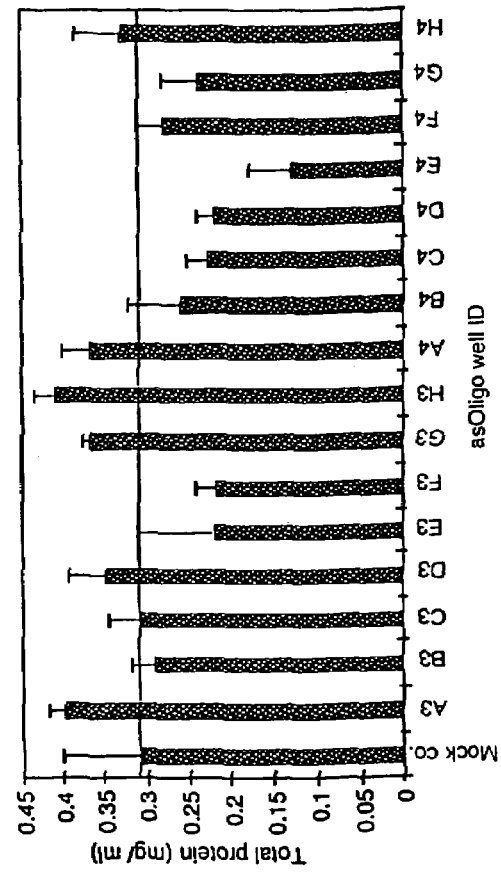
Figure 1E:
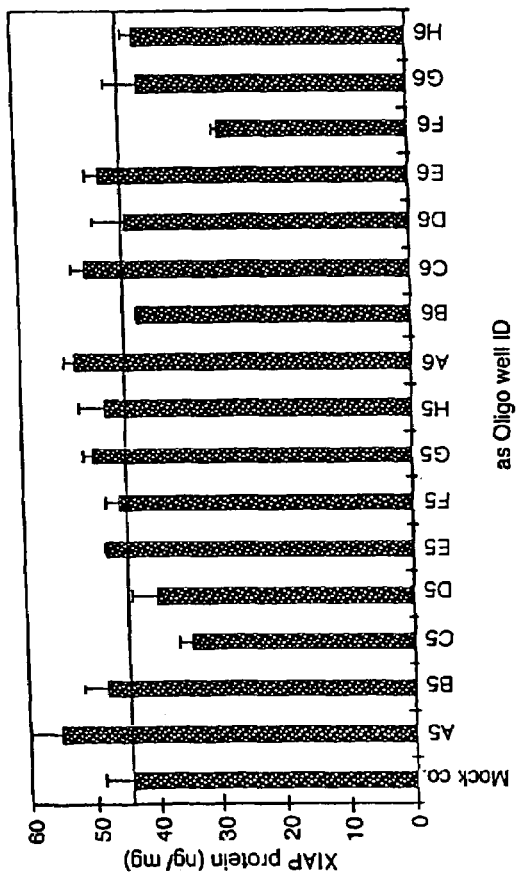
Figure 1F:
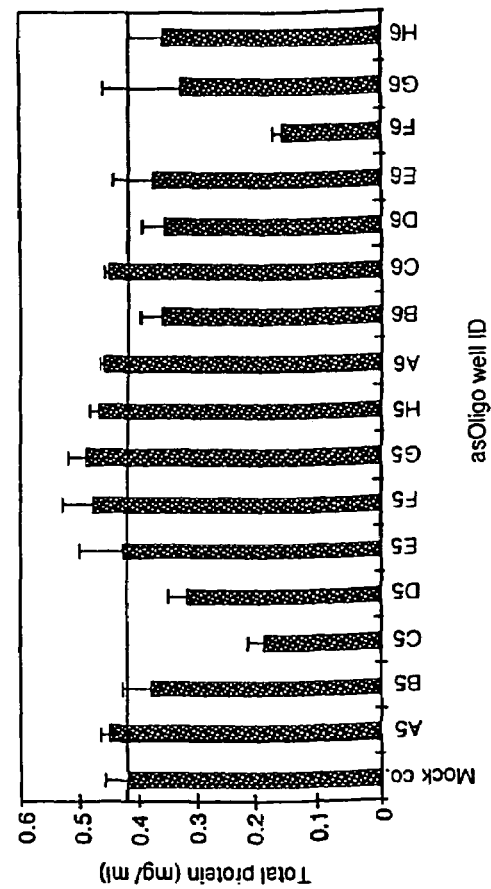
Figure 1G:
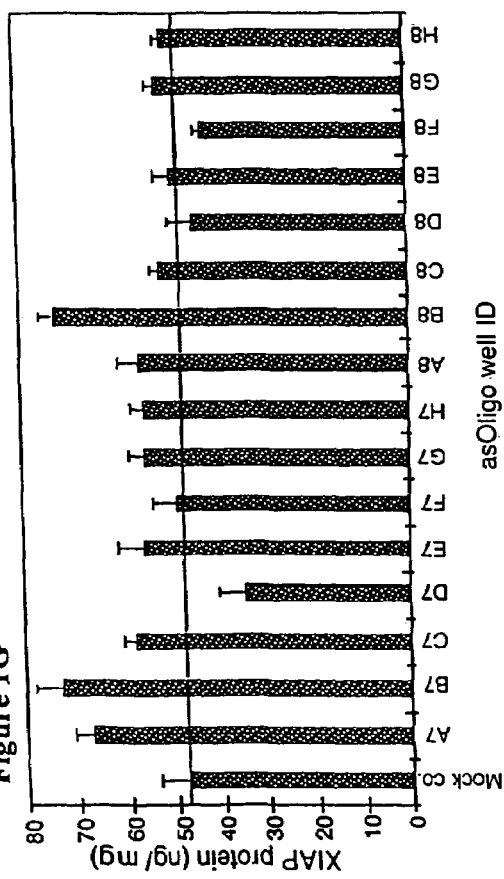
Figure 1H:
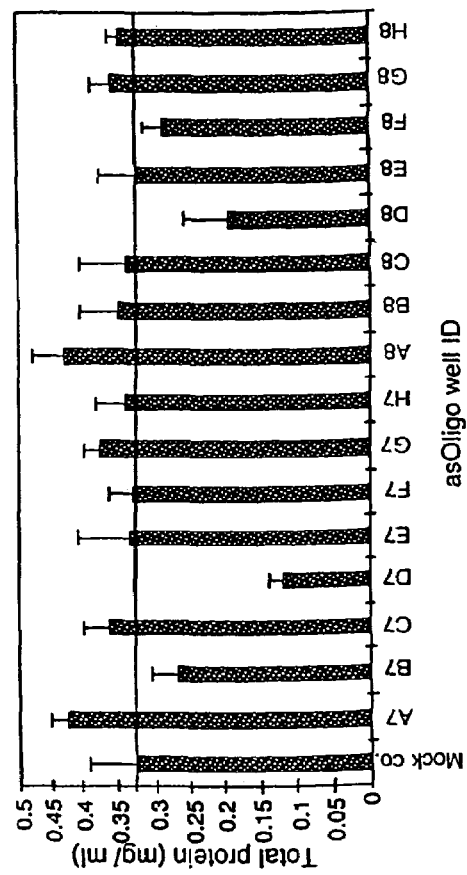
Figure 1K:
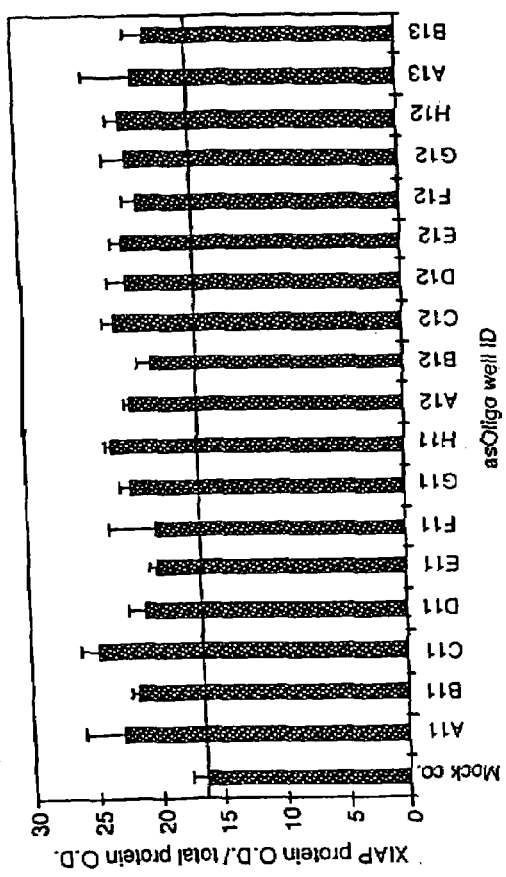
Figure 1L:
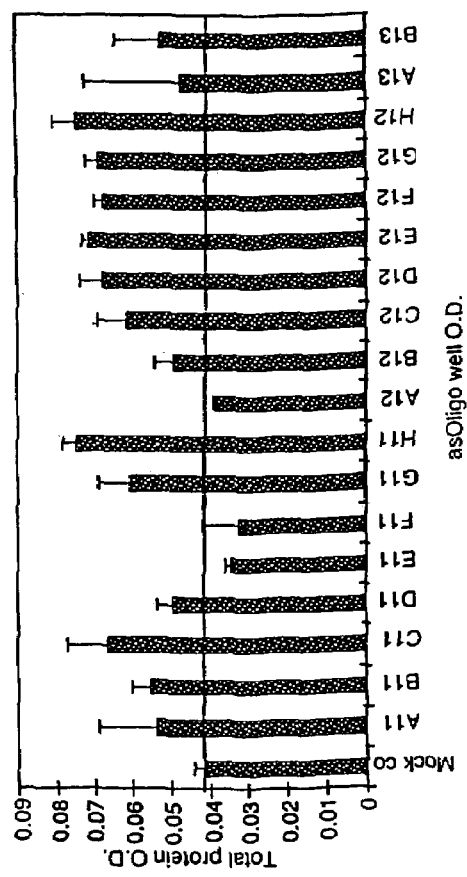

The present invention provides nucleobase oligomers that inhibit expression of an LAP, and methods for using them to induce apoptosis in a cell. The nucleobase oligomers of the present invention may also be used to form pharmaceutical compositions. The invention also features methods for enhancing apoptosis in a cell by administering an oligonucleotide of the invention in combination with a chemotherapeutic agent such as a cytotoxic agent, cytostatic agent, or biological response modifying agent (e.g., adriamycin, vinorelbine, etoposide, taxol, cisplatin, interferon, interleukin-2, monoclonal antibodies). The chemotherapeutic agent may be, for example. If desirable, a chemosensitizer (i.e., an agent that makes the proliferating cells more sensitive to the chemotherapy) may also be administered. Any combination of the foregoing agents may also be used to form a pharmaceutical composition. These pharmaceutical compositions may be used to treat a proliferative disease, for example, cancer or a lymphoproliferative disorder, or a symptom of a proliferative disease. The nucleobase oligomer of the invention may also be used in combination with radiotherapy for the treatment of cancer or other proliferative disease.

Activation of apoptosis in cancer cells offers novel, and potentially useful approaches to improve patient responses to conventional chemotherapy or radiotherapy. XIAP is the most potent member of the IAP gene family in terms of its ability to directly inhibit caspases and to suppress apoptosis. We investigated the effect of XIAP down-regulation by antisense (AS) oligonucleotides on human non-small cell lung cancer (NIH-H460) growth in vitro and in vivo. In cultured H460 human lung cancer cells, oligonucleotide G4 AS was identified as the most potent compound, effectively down-regulated XIAP mRNA by 55% and protein levels up to 60%, as determined by real-time RT-PCR and western blotting, respectively, and induced 60% cell death at 1.2 µM concentrations. In contrast, the scrambled control G4 oligonucleotide caused little XIAP loss and less than 10% cell death. Treatment with G4 AS induced apoptosis, as revealed by degradation of pro-caspase-3 and PARP proteins, with significant nuclear DNA condensation and fragmentation at 1.2 µM concentrations. Moreover, XIAP AS oligonucleotides sensitized H460 cells to the cytotoxic effects of doxorubicin, taxol, vinorelbine, and etoposide. In animal models, we demonstrate that G4 AS at 15 mg/kg had significant sequence-specific growth inhibitory effects on human H460 tumors in xenograft models of SCID/RAG2-immunodeficient mice by systemic intraperitoneal administration. Systemic AS ODN administration was associated with an 85% down-regulation of XIAP protein in tumor xenografts. The combination of 15 mg/kg G4 AS with 5 mg/kg vinorelbine significantly inhibited tumor growth, more than either agent alone. These studies indicate that down-regulation of XIAP is a potent death signal in lung carcinoma cells and is able to induce apoptosis in vitro as well as inhibit tumor growth in vivo. These studies support the contention that IAPs are suitable targets for cancer therapy in human non-small cell lung cancer, as well as other solid tumors.

Therapy

Therapy may be provided wherever cancer therapy is performed: at home, the doctor's office, a clinic, a hospital's outpatient department, or a hospital. Treatment generally begins at a hospital so that the doctor can observe the therapy's effects closely and make any adjustments that are needed. The duration of the therapy depends on the kind of cancer being treated, the age and condition of the patient, the stage and type of the patient's disease, and how the patient's body responds to the treatment. Drug administration may be performed at different intervals (e.g., daily, weekly, or monthly). Therapy may be given in on-and-off cycles that include rest periods so that the patient's body has a chance to build healthy new cells and regain its strength.

Depending on the type of cancer and its stage of development, the therapy can be used to slow the spreading of the cancer, to slow the cancer's growth, to kill or arrest cancer cells that may have spread to other parts of the body from the original tumor, to relieve symptoms caused by the cancer, or to prevent cancer in the first place.

As used herein, the terms "cancer" or "neoplasm" or "neoplastic cells" is meant a collection of cells multiplying in an abnormal manner. Cancer growth is uncontrolled and progressive, and occurs under conditions that would not elicit, or would cause cessation of, multiplication of normal cells.

A nucleobase oligomer of the invention, or other negative regulator of the IAP anti-apoptotic pathway, may be administered within a pharmaceutically-acceptable diluent, carrier, or excipient, in unit dosage form. Conventional pharmaceutical practice may be employed to provide suitable formulations or compositions to administer the compounds to patients suffering from a disease that is caused by excessive cell proliferation. Administration may begin before the patient is symptomatic. Any appropriate route of administration may be employed, for example, administration may be parenteral, intravenous, intraarterial, subcutaneous, intratumoral, intramuscular, intracranial, intraorbital, ophthalmic, intraventricular, intrahepatic, intracapsular, intrathecal, intracisternal, intraperitoneal, intranasal, aerosol, suppository, or oral administration. For example, therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington: The Science and Practice of Pharmacy" Ed. A. R. Gennaro, Lippincourt Williams & Wilkins, Philadelphia, Pa., 2000. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for IAP modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The formulations can be administered to human patients in therapeutically effective amounts (e.g., amounts which prevent, eliminate, or reduce a pathological condition) to provide therapy for a disease or condition. The preferred dosage of a nucleobase oligomer of the invention is likely to depend on such variables as the type and extent of the disorder, the overall health status of the particular patient, the formulation of the compound excipients, and its route of administration.

As described above, if desired, treatment with a nucleobase oligomer of the invention may be combined with therapies for the treatment of proliferative disease (e.g., radiotherapy, surgery, or chemotherapy).

For any of the methods of application described above, a nucleobase oligomer of the invention is desirably administered intravenously or is applied to the site of the needed apoptosis event (e.g., by injection).

Oligonucleotides and Other Nucleobase Oligomers

At least two types of oligonucleotides induce the cleavage of RNA by RNase H: polydeoxynucleotides with phosphodiester (PO) or phosphorothioate (PS) linkages. Although 2'-OMe-RNA sequences exhibit a high affinity for RNA targets, these sequences are not substrates for RNase H. A desirable oligonucleotide is one based on 2'-modified oligonucleotides containing oligodeoxynucleotide gaps with some or all internucleotide linkages modified to phosphorothioates for nuclease resistance. The presence of methylphosphonate modifications increases the affinity of the oligonucleotide for its target RNA and thus reduces the $IC_{50}$. This modification also increases the nuclease resistance of the modified oligonucleotide. It is understood that the methods and reagents of the present invention may be used in conjunction with any technologies that may be developed, including covalently-closed multiple antisense (CMAS) oligonucleotides (Moon et al., Biochem J. 346:295-303, 2000; PCT Publication No. WO 00/61595), ribbon-type antisense (RiAS) oligonucleotides (Moon et al., J. Biol. Chem. 275:4647-4653, 2000; PCT Publication No. WO 00/61595), and large circular antisense oligonucleotides (U.S. Patent Application Publication No. US 2002/0168631 A1).

As is known in the art, a nucleoside is a nucleobase-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric structure can be further joined to form a circular structure; open linear structures are generally preferred. Within the oligonucleotide structure, the phosphate groups are commonly referred to as forming the backbone of the oligonucleotide. The normal linkage or backbone of RNA and DNA is a 3' to 5' phosphodiester linkage.

Specific examples of preferred nucleobase oligomers useful in this invention include oligonucleotides containing modified backbones or non-natural internucleoside linkages.

As defined in this specification, nucleobase oligomers having modified backbones include those that retain a phosphorus atom in the backbone and those that do not have a phosphorus atom in the backbone. For the purposes of this specification, modified oligonucleotides that do not have a phosphorus atom in their internucleoside backbone are also considered to be nucleobase oligomers.

Nucleobase oligomers that have modified oligonucleotide backbones include, for example, phosphorothioates, chiral phosphorothioates, phosphorodithioates, phosphotriesters, aminoalkyl-phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity, wherein the adjacent pairs of nucleoside units are linked 3'-5' to 5'-3' or 2'-5' to 5'-2'. Various salts, mixed salts and free acid forms are also included. Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Nucleobase oligomers having modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative United States patents that teach the preparation of the above oligonucleotides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other nucleobase oligomers, both the sugar and the internucleoside linkage, i.e., the backbone, are replaced with novel groups. The nucleobase units are maintained for hybridization with an IAP. One such nucleobase oligomer, is referred to as a Peptide Nucleic Acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Methods for making and using these nucleobase oligomers are described, for example, in "Peptide Nucleic Acids: Protocols and Applications" Ed. P. E. Nielsen, Horizon Press, Norfolk, United Kingdom, 1999. Representative United States patents that teach the preparation of PNAs include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

In particular embodiments of the invention, the nucleobase oligomers have phosphorothioate backbones and nucleosides with heteroatom backbones, and in particular —$CH_2$—NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$—, and —O—N($CH_3$)—$CH_2$—$CH_2$—. In other embodiments, the oligonucleotides have morpholino backbone structures described in U.S. Pat. No. 5,034,506.

Nucleobase oligomers may also contain one or more substituted sugar moieties. Nucleobase oligomers comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl, and alkynyl may be substituted or unsubstituted $C_1$ to $C_{10}$ alkyl or $C_2$ to $C_{10}$ alkenyl and alkynyl. Particularly preferred are O[$(CH_2)_n$O]$_m$$CH_3$, O$(CH_2)_n$O$CH_3$, O$(CH_2)_n$$NH_2$, O$(CH_2)_n$$CH_3$, O$(CH_2)_n$O$NH_2$, and O$(CH_2)_n$ON[$(CH_2)_n$$CH_3$)]$_2$, where n and m are from 1 to about 10. Other preferred nucleobase oligomers include one of the following at the 2' position: $C_1$ to $C_{10}$ lower alkyl, substituted lower alkyl, alkaryl, aralkyl, O-alkaryl, or O-aralkyl, SH, S$CH_3$, OCN, Cl, Br, CN, $CF_3$, O$CF_3$, SO$CH_3$, $SO_2$$CH_3$, $ONO_2$, $NO_2$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of a nucleobase oligomer, or a group for improving the pharmacodynamic properties of an nucleobase oligomer, and other substituents having similar properties. Preferred modifications are 2'-O-methyl and 2'-methoxyethoxy (2'-O—$CH_2$$CH_2$O$CH_3$, also known as 2'-O-(2-methoxyethyl) or 2'-MOE). Another desirable modification is 2'-dimethylaminooxyethoxy (i.e., O$(CH_2)_2$ON$(CH_3)_2$), also known as 2'-DMAOE. Other modifications include, 2'-aminopropoxy (2'-O$CH_2$$CH_2$$CH_2$$NH_2$) and 2'-fluoro (2'-F). Similar modifications may also be made at other positions on an oligonucleotide or other nucleobase oligomer, particularly the 3' position of the sugar on the 3' terminal nucleotide or in 2'-5' linked oligonucleotides and the 5' position of 5' terminal nucleotide. Nucleobase oligomers may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Nucleobase oligomers may also include nucleobase modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine; 2-propyl and other alkyl derivatives of adenine and guanine; 2-thiouracil, 2-thiothymine and 2-thiocytosine; 5-halouracil and cytosine; 5-propynyl uracil and cytosine; 6-azo uracil, cytosine and thymine; 5-uracil (pseudouracil); 4-thiouracil; 8-halo, 8-amino, 8-thiol, 8-thioalkyl, 8-hydroxyl and other 8-substituted adenines and guanines; 5-halo (e.g., 5-bromo), 5-trifluoromethyl and other 5-substituted uracils and cytosines; 7-methylguanine and 7-methyladenine; 8-azaguanine and 8-azaadenine; 7-deazaguanine and 7-deazaadenine; and 3-deazaguanine and 3-deazaadenine. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are particularly useful for increasing the binding affinity of an antisense oligonucleotide of the invention. These include 5-substituted pyrimidines, 6-azapyrimidines, and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2.degree. C. (Sanghvi, Y. S., Crooke, S. T. and Lebleu, B., eds., Antisense Research and Applications, CRC Press, Boca Raton, 1993, pp. 276-278) and are desirable base substitutions, even more particularly when combined with 2'-O-methoxyethyl or 2'-O-methyl sugar modifications. Representative United States patents that teach the preparation of certain of the above noted modified nucleobases as well as other modified nucleobases include U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; and 5,750,692, each of which is herein incorporated by reference.

Another modification of a nucleobase oligomer of the invention involves chemically linking to the nucleobase oligomer one or more moieties or conjugates that enhance the activity, cellular distribution, or cellular uptake of the oligonucleotide. Such moieties include but are not limited to lipid moieties such as a cholesterol moiety (Letsinger et al., Proc. Natl. Acad. Sci. USA, 86:6553-6556, 1989), cholic acid (Manoharan et al., Bioorg. Med. Chem. Let, 4:1053-1060, 1994), a thioether, e.g., hexyl-S-tritylthiol (Manoharan et al., Ann. N.Y. Acad. Sci., 660:306-309, 1992; Manoharan et al., Bioorg. Med. Chem. Let., 3:2765-2770, 1993), a thiocholesterol (Oberhauser et al., Nucl. Acids Res., 20:533-538: 1992), an aliphatic chain, e.g., dodecandiol or undecyl residues (Saison-Behmoaras et al., EMBO J., 10:1111-1118, 1991; Kabanov et al., FEBS Lett., 259:327-330, 1990; Svinarchuk et al., Biochimie, 75:49-54, 1993), a phospholipid, e.g., di-hexadecyl-rac-glycerol or triethylammonium 1,2-di-O-hexadecyl-rac-glycero-3—H-phosphonate (Manoharan et al., Tetrahedron Lett., 36:3651-3654, 1995; Shea et al., Nucl. Acids Res., 18:3777-3783, 1990), a polyamine or a polyethylene glycol chain (Manoharan et al., Nucleosides & Nucleotides, 14:969-973, 1995), or adamantane acetic acid (Manoharan et al., Tetrahedron Lett., 36:3651-3654, 1995), a palmityl moiety (Mishra et al., Biochim. Biophys. Acta, 1264:229-237, 1995), or an octadecylamine or hexylamino-carbonyl-oxycholesterol moiety (Crooke et al., J. Pharmacol. Exp. Ther., 277:923-937, 1996. Representative United States patents that teach the preparation of such nucleobase oligomer conjugates include U.S. Pat. Nos. 4,587,044; 4,605,735; 4,667,025; 4,762,779; 4,789,737; 4,824,941; 4,828,979; 4,835,263; 4,876,335; 4,904,582; 4,948,882; 4,958,013; 5,082,830; 5,109,124; 5,112,963; 5,118,802; 5,138,045; 5,214,136; 5,218,105; 5,245,022; 5,254,469; 5,258,506; 5,262,536; 5,272,250; 5,292,873; 5,317,098; 5,371,241; 5,391,723; 5,414,077; 5,416,203; 5,451,463; 5,486,603; 5,510,475; 5,512,439; 5,512,667; 5,514,785; 5,525,465; 5,541,313; 5,545,730; 5,552,538; 5,565,552; 5,567,810; 5,574,142; 5,578,717; 5,578,718; 5,580,731; 5,585,481; 5,587,371; 5,591,584; 5,595,726; 5,597,696; 5,599,923; 5,599,928; 5,608,046; and 5,688,941, each of which is herein incorporated by reference.

The present invention also includes nucleobase oligomers that are chimeric compounds. "Chimeric" nucleobase oligomers are nucleobase oligomers, particularly oligonucleotides, that contain two or more chemically distinct regions, each made up of at least one monomer unit, i.e., a nucleotide in the case of an oligonucleotide. These nucleobase oligomers typically contain at least one region where the nucleobase oligomer is modified to confer, upon the nucleobase oligomer, increased resistance to nuclease degradation, increased cellular uptake, and/or increased binding affinity for the target nucleic acid. An additional region of the nucleobase oligomer may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of nucleobase oligomer inhibition of gene expression. Consequently, comparable results can often be obtained with shorter nucleobase oligomers when chimeric nucleobase oligomers are used, compared to phosphorothioate deoxyoligonucleotides hybridizing to the same target region.

Chimeric nucleobase oligomers of the invention may be formed as composite structures of two or more nucleobase oligomers as described above. Such nucleobase oligomers, when oligonucleotides, have also been referred to in the art as hybrids or gapmers. Representative United States patents that teach the preparation of such hybrid structures include U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

The nucleobase oligomers used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The nucleobase oligomers of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The nucleobase oligomers of the invention encompass any pharmaceutically acceptable salts, esters, or salts of such esters, or any other compound that, upon administration to an animal, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention can be prepared as SATE [(S-acetyl-2-thioethyl)phosphate] derivatives according to the methods disclosed in PCT publication Nos. WO 93/24510 or WO 94/26764.

The term "pharmaceutically acceptable salts" refers to salts that retain the desired biological activity of the parent compound and do not impart undesired toxicological effects thereto. Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., J. Pharma Sci., 66:1-19, 1977). The base addition salts of acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides and other nucleobase oligomers, suitable pharmaceutically acceptable salts include (i) salts formed with cations such as sodium, potassium, ammonium, magnesium, calcium, polyamines such as spermine and spermidine, etc.; (ii) acid addition salts formed with inorganic acids, for example hydrochloric acid, hydrobromic acid, sulfuric acid, phosphoric acid, nitric acid and the like; (iii) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (iv) salts formed from elemental anions such as chlorine, bromine, and iodine.

The present invention also includes pharmaceutical compositions and formulations that include the nucleobase oligomers of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral, or parenteral. Parenteral administration includes intravenous, intraarterial, subcutaneous, intraperitoneal, or intramuscular injection or infusion; or intracranial, e.g., intrathecal or intraventricular, administration.

Locked Nucleic Acids

Locked nucleic acids (LNAs) are nucleobase oligomers that can be employed in the present invention. LNAs contain a 2'O, 4'-C methylene bridge that restrict the flexibility of the ribofuranose ring of the nucleotide analog and locks it into the rigid bicyclic N-type conformation. LNAs show improved resistance to certain exo- and endonucleases and activate RNAse H, and can be incorporated into almost any nucleobase oligomer. Moreover, LNA-containing nucleobase oligomers can be prepared using standard phosphoramidite synthesis protocols. Additional details regarding LNAs can be found in PCT publication No. WO 99/14226 and U.S. Patent Application Publication No. US 2002/0094555 A1, each of which is hereby incorporated by reference.

Arabinonucleic Acids

Arabinonucleic acids (ANAs) can also be employed in methods and reagents of the present invention. ANAs are nucleobase oligomers based on D-arabinose sugars instead of the natural D-2'-deoxyribose sugars. Underivatized ANA analogs have similar binding affinity for RNA as do phosphorothioates. When the arabinose sugar is derivatized with fluorine (2' F-ANA), an enhancement in binding affinity results, and selective hydrolysis of bound RNA occurs efficiently in the resulting ANA/RNA and F-ANA/RNA duplexes. These analogs can be made stable in cellular media by a derivatization at their termini with simple L sugars. The use of ANAs in therapy is discussed, for example, in Damha et al., Nucleosides Nucleotides & Nucleic Acids 20: 429-440, 2001.

Delivery of Nucleobase Oligomers

We demonstrate herein that naked oligonucleotides are capable on entering tumor cells and inhibiting IAP expression. Nonetheless, it may be desirable to utilize a formulation that aids in the delivery of oligonucleotides or other nucleobase oligomers to cells (see, e.g., U.S. Pat. Nos. 5,656,611, 5,753,613, 5,785,992, 6,120,798, 6,221,959, 6,346,613, and 6,353,055, each of which is hereby incorporated by reference).

Ribozymes

Catalytic RNA molecules or ribozymes that include an antisense IAP sequence of the present invention can be used to inhibit expression of an IAP polynucleotide in vivo. The inclusion of ribozyme sequences within antisense RNAs confers RNA-cleaving activity upon them, thereby increasing the activity of the constructs. The design and use of target RNA-specific ribozymes is described in Haseloff et al., Nature 334:585-591. 1988, and U.S. Patent Application Publication No. 2003/0003469 A1, each of which is incorporated by reference.

Accordingly, the invention also features a catalytic RNA molecule that includes, in the binding arm, an antisense RNA having between eight and nineteen consecutive nucleobases corresponding to a sequence of any one of Tables 1, 2, 6, and 7. In preferred embodiments of this invention, the catalytic nucleic acid molecule is formed in a hammerhead or hairpin motif, but may also be formed in the motif of a hepatitis delta virus, group I intron or RNaseP RNA (in association with an RNA guide sequence) or Neurospora VS RNA. Examples of such hammerhead motifs are described by Rossi et al., Aids Research and Human Retroviruses, 8:183, 1992. Example of hairpin motifs are described by Hampel et al., "RNA Catalyst for Cleaving Specific RNA Sequences," filed Sep. 20, 1989, which is a continuation-in-part of U.S. Ser. No. 07/247,100 filed Sep. 20, 1988, Hampel and Tritz, Biochemistry, 28:4929, 1989, and Hampel et al., Nucleic Acids Research, 18: 299, 1990. An example of the hepatitis delta virus motif is described by Perrotta and Been, Biochemistry, 31:16, 1992. The RNaseP motif is described by Guerrier-Takada et al., Cell, 35:849, 1983. The Neurospora VS RNA ribozyme motif is described by Collins et al. (Saville and Collins, Cell 61:685-696, 1990; Saville and Collins, Proc. Natl. Acad. Sci. USA 88:8826-8830, 1991; Collins and Olive, Biochemistry 32:2795-2799, 1993). These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

RNA interference

The nucleobase oligomers of the present invention may be employed in double-stranded RNAs for RNA interference (RNAi)-mediated knock-down of IAP expression. RNAi is a method for decreasing the cellular expression of specific proteins of interest (reviewed in Tuschl, Chembiochem 2:239-245, 2001; Sharp, Genes & Devel. 15:485-490, 2000; Hutvagner and Zamore, Curr. Opin. Genet. Devel. 12:225-232, 2002; and Hannon, Nature 418:244-251, 2002). In RNAi, gene silencing is typically triggered post-transcriptionally by the presence of double-stranded RNA (dsRNA) in a cell. This dsRNA is processed intracellularly into shorter pieces called small interfering RNAs (siRNAs). The introduction of siRNAs into cells either by transfection of dsRNAs or through expression of siRNAs using a plasmid-based expression system is increasingly being used to create loss-of-function phenotypes in mammalian cells.

In one embodiment of the invention, double-stranded RNA (dsRNA) molecule is made that includes between eight and nineteen consecutive nucleobases of a nucleobase oligomer of the invention. The dsRNA can be two distinct strands of RNA that have duplexed, or a single RNA strand that has self-duplexed (small hairpin (sh)RNA). Typically, dsRNAs are about 21 or 22 base pairs, but may be shorter or longer (up to about 29 nucleobases) if desired. dsRNA can be made using standard techniques (e.g., chemical synthesis or in vitro transcription). Kits are available, for example, from Ambion (Austin, Tex.) and Epicentre (Madison, Wis.). Methods for expressing dsRNA in mammalian cells are described in Brummelkamp et al. Science 296:550-553, 2002; Paddison et al. Genes & Devel. 16:948-958, 2002. Paul et al. Nature Biotechnol. 20:505-508, 2002; Sui et al. Proc. Natl. Acad. Sci. USA 99:5515-5520, 2002; Yu et al. Proc. Natl. Acad. Sci. USA 99:6047-6052, 2002; Miyagishi et al. Nature Biotechnol. 20:497-500, 2002; and Lee et al. Nature Biotechnol. 20:500-505 2002, each of which is hereby incorporated by reference.

Small hairpin RNAs consist of a stem-loop structure with optional 3' UU-overhangs. While there may be variation, stems can range from 21 to 31 bp (desirably 25 to 29 bp), and the loops can range from 4 to 30 bp (desirably 4 to 23 bp). For expression of shRNAs within cells, plasmid vectors containing either the polymerase III H1-RNA or U6 promoter, a cloning site for the stem-looped RNA insert, and a 4-5-thymidine transcription termination signal can be employed. The Polymerase III promoters generally have well-defined initiation and stop sites and their transcripts lack poly(A) tails. The termination signal for these promoters is defined by the polythymidine tract, and the transcript is typically cleaved after the second uridine. Cleavage at this position generates a 3' UU overhang in the expressed shRNA, which is similar to the 3' overhangs of synthetic siRNAs. Additional methods for expressing the shRNA in mammalian cells are described in the references cited above.

The following examples are to illustrate the invention. They are not meant to limit the invention in any way.

EXAMPLE 1

Nucleobase Oligomer Selection

We selected 96 and 98, mostly non-overlapping, 19-mer nucleobase sequences for human XIAP and HIAP1, respectively, based on the selection criteria listed below. In the case of XIAP, we selected 96 sequences (each being 19 nucleobases in length) (SEQ ID NOs: 1 through 96; Table 1), from a region approximately 1 kb upstream of the start codon to approximately 1 kb downstream of the stop codon of the cDNA sequence. This blanketed approximately 50% of the coding region, and immediate 5' and 3' UTR sequences (i.e., 96 19-mers span 1.8 kb of sequence, while the targeted region is approximately 3.5 kb in length, comprised of a coding region of 1.5 kb plus 1 kb at either side of UTR sequences).

TABLE 1

| SEQ ID NO: | Code | Nucleobase Sequence | XIAP down-regulation T24 RNA | XIAP down-regulation T24 protein | XIAP down-regulation H460 RNA |
|---|---|---|---|---|---|
| 1 | A1 | AAAATTCTAAGTACCTGCA | — | — | 48% |
| 2 | B1 | TCTAGAGGGTGGCTCAGGA | — | — | 66% |
| 3 | C1 | CAGATATATATGTAACACT | — | — | 66% |
| 4 | D1 | TGAGAGCCCTTTTTTGTT | — | — | 75% |
| 5 | E1 | AGTATGAAATATTTCTGAT | — | — | 69% |
| 6 | F1 | ATTGGTTCCAATGTGTTCT | — | — | 81% |
| 7 | G1 | TTAGCAAAATATGTTTTAA | — | — | 33% |
| 8 | H1 | TGAATTAATTTTTAATATC | — | — | 13% |
| 9 | A2 | ATTCAAGGCATCAAAGTTG | — | — | 58% |
| 10 | B2 | GTCAAATCATTAATTAGGA | — | — | 55% |
| 11 | C2 | AATATGTAAACTGTGATGC | 36% | 45% | 70% |
| 12 | D2 | GCAGAATAAAACTAATAAT | — | — | 39% |
| 13 | E2 | GAAAGTAATATTTAAGCAG | 54% | 51% | 60% |
| 14 | F2 | TTACCACATCATTCAAGTC | — | — | 34% |
| 15 | G2 | CTAAATACTAGAGTTCGAC | — | — | 55% |
| 16 | H2 | ACACGACCGCTAAGAAACA | — | — | 46% |
| 17 | A3 | TATCCACTTATGACATAAA | — | — | 27% |
| 18 | B3 | GTTATAGGAGCTAACAAAT | — | — | 34% |
| 19 | C3 | AATGTGAAACACAAGCAAC | — | — | 43% |
| 20 | D3 | ACATTATATTAGGAAATCC | — | — | 30% |
| 21 | E3 | CTTGTCCACCTTTTCTAAA | 53% | 64% | 55% |
| 22 | F3 | ATCTTCTCTTGAAAATAGG | 44% | 53% | — |
| 23 | G3 | CCTTCAAAACTGTTAAAAG | — | — | — |
| 24 | H3 | ATGTCTGCAGGTACACAAG | — | — | — |
| 25 | A4 | ATCTATTAAACTCTTCTAC | — | — | — |
| 26 | B4 | ACAGGACTACCACTTGGAA | — | — | 76% |
| 27 | C4 | TGCCAGTGTTGATGCTGAA | 28% | 56% | 77% |
| 28 | D4 | GTATAAAGAAACCCTGCTC | 12% | 43% | 51% |
| 29 | E4 | CGCACGGTATCTCCTTCAC | 47% | 34% | 51% |
| 30 | F4 | CTACAGCTGCATGACAACT | 33% | 43% | — |
| 31 | G4 | GCTGAGTCTCCATATTGCC | 34% | 48% | 51% |
| 32 | H4 | ATACTTTCCTGTGTCTTCC | — | — | — |
| 33 | A5 | GATAAATCTGCAATTTGGG | — | — | — |
| 34 | B5 | TTGTAGACTGCGTGGCACT | — | — | 61% |
| 35 | C5 | ACCATTCTGGATACCAGAA | 71% | 54% | — |
| 36 | D5 | AGTTTTCAACTTTGTACTG | 39% | 33% | — |
| 37 | E5 | ATGATCTCTGCTTCCCAGA | — | — | 46% |

TABLE 1-continued

| SEQ ID NO: | Code | Nucleobase Sequence | XIAP down-regulation T24 RNA | XIAP down-regulation T24 protein | XIAP down-regulation H460 RNA |
|---|---|---|---|---|---|
| 38 | F5 | AGATGGCCTGTCTAAGGCA | — | — | — |
| 39 | G5 | AGTTCTCAAAAGATAGTCT | — | — | 30% |
| 40 | H5 | GTGTCTGATATATCTACAA | — | — | 39% |
| 41 | A6 | TCGGGTATATGGTGTCTGA | — | — | 72% |
| 42 | B6 | CAGGGTTCCTCGGGTATAT | 51% | 47% | — |
| 43 | C6 | GCTTCTTCACAATACATGG | — | — | — |
| 44 | D6 | GGCCAGTTCTGAAAGGACT | — | — | 60% |
| 45 | E6 | GCTAACTCTCTTGGGGTTA | — | — | — |
| 46 | F6 | GTGTAGTAGAGTCCAGCAC | 34% | 39% | — |
| 47 | G6 | AAGCACTGCACTTGGTCAC | — | — | 69% |
| 48 | H6 | TTCAGTTTTCCACCACAAC | — | — | 68% |
| 49 | A7 | ACGATCACAAGGTTCCCAA | — | — | — |
| 50 | B7 | TCGCCTGTGTTCTGACCAG | — | — | — |
| 51 | C7 | CCGGCCCAAAACAAAGAAG | — | — | 72% |
| 52 | D7 | GATTCACTTCGAATATTAA | 56% | 88% | 46% |
| 53 | E7 | TATCAGAACTCACAGCATC | — | — | — |
| 54 | F7 | GGAAGATTTGTTGAATTTG | — | — | 69% |
| 55 | G7 | TCTGCCATGGATGGATTTC | — | — | 41% |
| 56 | H7 | AAGTAAAGATCCGTGCTTC | — | — | 63% |
| 57 | A8 | CTGAGTATATCCATGTCCC | — | — | — |
| 58 | B8 | GCAAGCTGCTCCTTGTTAA | — | — | — |
| 59 | C8 | AAAGCATAAAATCCAGCTC | — | — | 16% |
| 60 | D8 | GAAAGCACTTTACTTTATC | 38% | 26% | 49% |
| 61 | H8 | ACTGGGCTTCCAATCAGTT | — | — | — |
| 62 | E8 | GTTGTTCCCAAGGGTCTTC | 72% | 56% | 44% |
| 63 | F8 | ACCCTGGATACCATTTAGC | — | — | 47% |
| 64 | G8 | TGTTCTAACAGATATTTGC | — | — | 49% |
| 65 | A9 | TATATATTCTTGTCCCTTC | — | — | 62% |
| 66 | B9 | AGTTAAATGAATATTGTTT | — | — | 38% |
| 67 | C9 | GACACTCCTCAAGTGAATG | — | — | — |
| 68 | D9 | TTTCTCAGTAGTTCTTACC | — | — | 39% |
| 69 | E9 | GTTAGTGATGGTGTTTTCT | — | — | 43% |
| 70 | F9 | AGATGGTATCATCAATTCT | — | — | 19% |
| 71 | G9 | TGTACCATAGGATTTTGGA | — | — | — |
| 72 | H9 | CCCCATTCGTATAGCTTCT | — | — | — |
| 73 | A10 | ATTATTTTCTTAATGTCCT | — | — | 29% |

TABLE 1-continued

| SEQ ID NO: | Code | Nucleobase Sequence | XIAP down-regulation T24 RNA | XIAP down-regulation T24 protein | XIAP down-regulation H460 RNA |
|---|---|---|---|---|---|
| 74 | B10 | CAAGTGATTTATAGTTGCT | — | — | — |
| 75 | C10 | TAGATCTGCAACCAGAACC | — | — | 53% |
| 76 | D10 | CATCTTGCATACTGTCTTT | — | — | 55% |
| 77 | E10 | CCTTAGCTGCTCTTCAGTA | — | — | — |
| 78 | F10 | AAGCTTCTCCTCTTGCAGG | — | — | 51% |
| 79 | G10 | ATATTTCTATCCATACAGA | — | — | 56% |
| 80 | H10 | CTAGATGTCCACAAGGAAC | — | — | — |
| 81 | A11 | AGCACATTGTTTACAAGTG | — | — | 68% |
| 82 | B11 | AGCACATGGGACACTTGTC | — | — | 63% |
| 83 | C11 | CTTGAAAGTAATGACTGTG | — | — | 52% |
| 84 | D11 | CCTACTATAGAGTTAGATT | — | — | — |
| 85 | E11 | ATTCAATCAGGGTAATAAG | — | — | 48% |
| 86 | F11 | AAGTCAGTTCACATCACAC | — | — | 64% |
| 87 | G11 | CAGTAAAAAAAATGGATAA | — | — | 33% |
| 88 | H11 | TTCAGTTATAGTATGATGC | — | — | — |
| 89 | A12 | TACACTTAGAAATTAAATC | — | — | 46% |
| 90 | B12 | TCTCTATCTTTCCACCAGC | — | — | — |
| 91 | C12 | AGAATCCTAAAACACAACA | — | — | — |
| 92 | D12 | ATTCGCACAAGTACGTGTT | — | — | 77% |
| 93 | E12 | TGTCAGTACATGTTGGCTC | — | — | 74% |
| 94 | F12 | ACATAGTGTTTTGCCACTT | — | — | 74% |
| 95 | G12 | CTTTGATCTGGCTCAGACT | — | — | 76% |
| 96 | H12 | GAAACCACATTTAACAGTT | — | — | 52% |

Note that in any of the foregoing nucleobase oligomers, or any other nucleobase oligomers described herein, each nucleobase may independently be a DNA residue or RNA residue, such as a 2'-O-methyl or 2'-O-methoxyethyl RNA residue. For example, the nucleobase sequence of SEQ ID NO: 3 may be, for example, 5'-CAGATATATATG TAA-CACT-3', 5'-CAGATATATATGTAACACU-3', or 5'-mCmA-GATATATATGTA ACAmCmU-3' (wherein mX represents a 2'-O-methyl X residue). Additional modified nucleobases are known in the art. The linkages may be phosphodiester (PO), phosphorothioate (PS), or methylphosphonate (MP) linkages, or may have a mixed backbone (MB). The backbone may be any suitable backbone that allows hybridization of the nucleobase oligomer to the target IAP polynucleotide. Exemplary backbones are described herein. In other embodiments, the nucleobase oligomers include acridine-protected linkages, cholesteryl or psoralen components, C5-propynyl pyrimidines, or C5-methyl pyrimidines. Suitable modifications to the nucleobase oligomers of the invention include those described above, as well as those in U.S. Patent Application Publication No. US 2002/0128216 A1, hereby incorporated by reference.

Examples of nucleobase oligomers are provided in Table 2, below (wherein mX represents a 2'-O-methyl X RNA residue).

TABLE 2

| 2 × 2 MB PO | | SEQ ID NO: |
|---|---|---|
| DE4 as | mGmGTATCTCCTTCACCAGmUmA | 97 |
| DE4 rev | mAmUGACCACTTCCTCTATmGmG | 98 |
| δBC5 as | mGmATACCAGAATTTmGmU | 99 |
| δBC5 rev | mUmGTTTAAGACCATmAmG | 100 |

TABLE 2-continued

| | | SEQ ID NO: |
|---|---|---|
| mG4 as | mGmCTGAGTCTCCATACTGmCmC | 101 |
| mG4 sm | mGmGCTCTCTGCCCACTGAmAmU | 102 |
| 3 × 3 MB PO | | |
| F3 as | mAmUmCTTCTCTTGAAAATmAmGmG | 103 |
| F3 scr | mCmCmAmGAGATTTCATTTAAmCmGmU | 104 |
| F3 mm | mAmUmCTTGACTTGATTATmAmGmG | 105 |
| F3 rev | mGmGmATAAAAGTTCTCTTmCmUmA | 106 |
| E4 as | mCmGmCACGGTATCTCCTTmCmAmC | 107 |
| E4 scr | mCmUmACGCTCGCCATCGTmUmCmA | 108 |
| E4 rev | mCmAmCTTCCTCTATGGCAmCmGmC | 109 |
| E4 mm | mCmGmCACCCTATCTGGTTmCmAmC | 110 |
| G4 as | mGmCmUGAGTCTCCATATTmGmCmC | 111 |
| G4 scr | mGmCmCTCTTTCGCCACTGmAmAmU | 112 |
| G4 rev | mCmCmGTTATACCTCTGAGmUmCmG | 113 |
| G4 mm | mGmCmUGACACTCCAATTTmGmCmC | 114 |
| C5 as | mAmCmCATTCTGGTAACCAmGmAmA | 115 |
| C5 scr | mUmGmCCCAAGAATACTAGmUmCmA | 116 |
| C5 mm | mAmCmCATAGTGGATTGCAmGmAmA | 117 |
| C5 rev | mAmAmGACCATAGGTCTTAmCmCmA | 118 |
| D7 as | mGmAmUTCACTTCTTCGAATATmUmAmA | 119 |
| D7 scr | mUmGmAAATGTAAATCATCmUmUmC | 120 |
| D7 mm | mGmAmUTCTGTTCGATAATmUmAmA | 121 |
| D7 rev | mAmAmUTATAAGCTTCACTmUmAmG | 122 |
| Phosphorothioate | | |
| PS-G4 as | GCTGAGTCTCCATATTGCC | 123 |
| PS-G4 sm | GGCTCTTTGCCCACTGAAT | 124 |
| PS-C5 as | ACCATTCTGGATACCAGAA | 125 |
| PS-C5 rev | AAGACCATAGGTCTTACCA | 126 |
| PS-F3 as | ATCTTCTCTTGAAAATAGG | 127 |
| PS-F3 rev | GGATAAAAGTTCTCTTCTA | 128 |
| PS-DE4 as | GGTATCTCCTTCACCAGTA | 129 |
| PS-DE4 rev | ATGACCACTTCCTCTATGG | 130 |
| PS-BC5 as | TCTGGATACCAGAATTTGT | 131 |
| PS-BC5 rev | TGTTTAAGACCATAGGTCT | 132 |
| PS-AB6 as | GGGTTCCTCGGGTATATGG | 133 |
| PS-AB6 rs | GGTATATGGCGTCCTTGGG | 134 |
| PS-D7 as | GATTCACTTCGAATATTAA | 135 |
| PS-D7 rs | AATTATAACGTTCACTTAG | 136 |

TABLE 2-continued

| | | SEQ ID NO: |
|---|---|---|
| Penetratin | | |
| F3 as | ATCTTCTCTTGAAAATAGG | 137 |
| G4 as | GCTGAGTCTCCATATTGCC | 138 |
| D7 as | GATTCACTTCGAATATTAA | 139 |
| C5 cs | TGCCCAAGAATACTAGTCA | 140 |
| 4 × 4 MBO PS (phosphorothioate linkages throughout) | | |
| G4 as | mGmCmUmGAGTCTCCATATmUmGmCmC | 141 |
| G4 sm | mGmGmCmUCTTTGCCCACTmGmAmAmU | 142 |
| DE4 as | mGmGmUmATCTCCTTCACCmAmGmUmA | 143 |
| DE4 rev | mAmUmGmACCACTTCCTCTmAmUmGmG | 144 |
| E2 as | mGmAmAmAGTAATATTTAAmGmCmAmG | 145 |
| E2 rm | mGmAmGmCAATTTATAATGmAmAmAmG | 146 |
| H2G as | mAmCmCmGCTAAGAAACATmUmCmUmA | 147 |
| H2G rm | mAmUmCmUTACAAAGAATCmCmGmCmA | 148 |
| A3 as | mUmAmUmCCACTTATGACAmUmAmAmA | 149 |
| A3 rev | mAmAmAmUACAGTATTCACmCmUmAmU | 150 |
| FG8 as | mUmGmCmACCCTGGATACCmAmUmUmU | 151 |
| FG8 rm | mUmUmUmACCATAGGTCCCmAmGmGmU | 152 |
| mG4 as | mGmCmUmGAGTCTCCATACmUmGmCmC | 153 |
| mG4 sm | mGmGmCmUCTCTGCCCACTmGmAmAmU | 154 |
| F1 as | mAmUmUmGGTTCCAATGTGmUmUmCmU | 155 |
| F1 rev | mUmCmUmUGTGTAACCTTGmGmUmUmA | 156 |
| B4 as | mAmCmAmGGACTACCACTTmGmGmAmA | 157 |
| B4 rev | mAmAmGmGTTCACCATCAGmGmAmCmA | 158 |
| G6 as | mAmAmGmCACTGCACTTGGmUmCmAmC | 159 |
| G6 sm | mCmAmCmTGGTTGACCTCAmCmAmAmG | 160 |
| E12 as | mUmGmUmCAGTACATGTTGmCmCmUmC | 161 |
| E12 sm | mCmUmAmGGTTGTCCATGAmCmUmGmU | 162 |

Penetratin and its use in mediating entry of nucleobase oligomers into cells are described in PCT patent application No. FR 91/00444.

A similar identification approach was taken for designing nucleobase oligomers against HIAP1. Initially, 98 19-mer nucleobase oligomers were chosen (SEQ ID NOs: 163-260; Table 3). Of these 98 nucleobase oligomers targeted to the HIAP1 sequence, fifteen (SEQ ID NOs: 163-170, 173, 179, 202, 222, 223, 247, and 259) were selected for further evaluation. These fifteen candidate nucleobase oligomers included four nucleobase oligomers targeting the coding region (SEQ ID NOs: 202, 222, 223, and 247), one nucleobase oligomer targeting the 3' UTR (SEQ ID NO: 259), seven nucleobase oligomers targeting the 5' UTR (SEQ ID NOs: 166-170, 173, and 179; one of the seven nucleobase oligomers overlapped the start codon), and three other oligonucleotides (SEQ ID NOs: 163-165) that were designed to target an intronic segment of the 5' UTR.

TABLE 3

| SEQ ID NO: | Code | Nucleobase Oligomer Sequence |
|---|---|---|
| 163 | APO 1 | TCATTTGAGCCTGGGAGGT |
| 164 | APO 2 | CGGAGGCTGAGGCAGGAGA |
| 165 | APO 3 | GGTGTGGTGGTACGCGCCT |
| 166 | APO 4 | ACCCATGCACAAAACTACC |
| 167 | APO 5 | AGAATGTGCCAGTAGGAGA |
| 168 | APO 6 | TCTCACAGACGTTGGGCTT |
| 169 | APO 7 | CCAGTGGTTTGCAAGCATG |
| 170 | APO 8 | GAAATTTAGTGGCCAGGAA |
| 171 |  | AGAAATACACAATTGCACC |
| 172 |  | TACTGATACATTTTAAGGA |
| 173 | APO 9 | TTCAACATGGAGATTCTAA |
| 174 |  | ATTTCTATGCATTTAGAGT |
| 175 |  | AATACTAGGCTGAAAAGCC |
| 176 |  | GGCTTTGCTTTTATCAGTT |
| 177 |  | TCTAGGGAGGTAGTTTTGT |
| 178 |  | GGGAAGAAAAGGGACTAGC |
| 179 | APO 10 | GTTCATAATGAAATGAATG |
| 180 |  | ATAAGAATATGCTGTTTTC |
| 181 |  | TTCAAACGTGTTGGCGCTT |
| 182 |  | ATGACAAGTCGTATTTCAG |
| 183 |  | AAGTGGAATACGTAGACAT |
| 184 |  | AGACAGGAACCCCAGCAGG |
| 185 |  | CGAGCAAGACTCCTTTCTG |
| 186 |  | AGTGTAATAGAAACCAGCA |
| 187 |  | TGACCTTGTCATTCACACC |
| 188 |  | TTATCCAGCATCAGGCCAC |
| 189 |  | ACTGTCTCCTCTTTTCCAG |
| 190 |  | TTTTATGCTTTTCAGTAGG |
| 191 |  | ACGAATCTGCAGCTAGGAT |
| 192 |  | CAAGTTGTTAACGGAATTT |
| 193 |  | TAGGCTGAGAGGTAGCTTC |
| 194 |  | GTTACTGAAGAAGGAAAAG |
| 195 |  | GAATGAGTGTGTGGAATGT |
| 196 |  | TGTTTTCTGTACCCGGAAG |
| 197 |  | GAGCCACGGAAATATCCAC |
| 198 |  | TGATGGAGAGTTTGAATAA |

TABLE 3-continued

| SEQ ID NO: | Code | Nucleobase Oligomer Sequence |
|---|---|---|
| 199 |  | GATTTGCTCTGGAGTTTAC |
| 200 |  | GGCAGAAAATTCTTGATTT |
| 201 |  | GGACAGGGGTAGGAACTTC |
| 202 | APO 11 | GCATTTTCGTTATTCATTG |
| 203 |  | CTGAAAAGTAAGTAATCTG |
| 204 |  | GGCGACAGAAAAGTCAATG |
| 205 |  | CCACTCTGTCTCCAGGTCC |
| 206 |  | CCACCACAGGCAAAGCAAG |
| 207 |  | TTCGGTTCCCAATTGCTCA |
| 208 |  | TTCTGACATAGCATTATCC |
| 209 |  | TGGGAAATGTCTCAGGTG |
| 210 |  | TATAAATGGGCATTTGGGA |
| 211 |  | TGTCTTGAAGCTGATTTTC |
| 212 |  | GAAACTGTGTATCTTGAAG |
| 213 |  | TGTCTGCATGCTCAGATTA |
| 214 |  | GAATGTTTTAAAGCGGGCT |
| 215 |  | CACTAGAGGGCCAGTTAAA |
| 216 |  | CCGCACTTGCAAGCTGCTC |
| 217 |  | CATCATCACTGTTACCCAC |
| 218 |  | CCACCATCACAGCAAAAGC |
| 219 |  | TCCAGATTCCCAACACCTG |
| 220 |  | CCCATGGATCATCTCCAGA |
| 221 |  | AACCACTTGGCATGTTGAA |
| 222 | APO 12 | CAAGTACTCACACCTTGGA |
| 223 | APO 13 | CCTGTCCTTTAATTCTTAT |
| 224 |  | TGAACTTGACGGATGAACT |
| 225 |  | TAGATGAGGGTAACTGGCT |
| 226 |  | TGGATAGCAGCTGTTCAAG |
| 227 |  | CATTTTCATCTCCTGGGCT |
| 228 |  | TGGATAATTGATGACTCTG |
| 229 |  | GTCTTCTCCAGGTTCAAAA |
| 230 |  | TATTCATCATGATTGCATC |
| 231 |  | CATTTCCACGGCAGCATTA |
| 232 |  | CCAGGCTTCTACTAAAGCC |
| 233 |  | GCTAGGATTTTCTCTGAA |
| 234 |  | TCTATAATTCTCTCCAGTT |
| 235 |  | ACACAAGATCATTGACTAG |

TABLE 3-continued

| SEQ ID NO: | Code | Nucleobase Oligomer Sequence |
|---|---|---|
| 236 | | TCTGCATTGAGTAAGTCTA |
| 237 | | CTCTTCCCTTATTTCATCT |
| 238 | | TCCTCAGTTGCTCTTTCTC |
| 239 | | GCCATTCTATTCTTCCGGA |
| 240 | | AGTCAAATGTTGAAAAAGT |
| 241 | | CCAGGATTGGAATTACACA |
| 242 | | ATTCCGGCAGTTAGTAGAC |
| 243 | | TAACATCATGTTCTTGTTC |
| 244 | | GTCTGTGTCTTCTGTTTAA |
| 245 | | TTCTCTTGCTTGTAAAGAC |
| 246 | | CTAAAATCGTATCAATCAG |
| 247 | APO 14 | GGCTGCAATATTTCCTTTT |
| 248 | | GAGAGTTTCTGAATACAGT |
| 249 | | ACAGCTTCAGCTTCTTGCA |
| 250 | | AAATAAATGCTCATATAAC |
| 251 | | GAAACATCTTCTGTGGGAA |
| 252 | | GTTCTTCCACTGGTAGATC |
| 253 | | CTTCTTGTAGTCTCCGCAA |
| 254 | | TTGTCCATACACACTTTAC |
| 255 | | AACCAAATTAGGATAAAAG |
| 256 | | ATGTTCATATGGTTTAGAT |
| 257 | | TAAGTTTTACTTCACTTAC |
| 258 | | ATGTTCCCGGTATTAGTAC |
| 259 | APO 15 | GGGCTCAAGTAATTCTCTT |
| 260 | | GCCCAGGATGGATTCAAAC |

Nucleobase Oligomer Selection Criteria

The computer program OLIGO (previously distributed by National Biosciences Inc.) was used to select candidate nucleobase oligomers based on the following criteria:

1) no more than 75% GC content, and no more than 75% AT content;
2) preferably no nucleobase oligomers with four or more consecutive G residues (due to reported toxic effects, although one was chosen as a toxicity control);
3) no nucleobase oligomers with the ability to form stable dimers or hairpin structures; and
4) sequences around the translation start site are a preferred region.

In addition, accessible regions of the target mRNA were predicted with the help of the RNA secondary structure folding program MFOLD (M. Zuker, D. H. Mathews & D. H. Turner, Algorithms and Thermodynamics for RNA Secondary Structure Prediction: A Practical Guide. In: *RNA Biochemistry and Biotechnology*, J. Barciszewski & B. F. C. Clark, eds., NATO ASI Series, Kluwer Academic Publishers, (1999). Sub-optimal folds with a free energy value within 5% of the predicted most stable fold of the mRNA were predicted using a window of 200 bases within which a residue can find a complimentary base to form a base pair bond. Open regions that did not form a base pair were summed together with each suboptimal fold and areas that consistently were predicted as open were considered more accessible to the binding to nucleobase oligomers. Additional nucleobase oligomer that only partially fulfilled some of the above selection criteria were also chosen as possible candidates if they recognized a predicted open region of the target mRNA.

EXAMPLE 2

Oligonucleotide Synthesis

The ability of nucleobase oligomers to inhibit IAP expression was tested using oligonucleotides as exemplary nucleobase oligomers. The oligonucleotides were synthesized by IDT (Integrated DNA Technologies, USA) as chimeric, second-generation oligonucleotides, consisting of a core of phosphodiester DNA residues flanked on either side by two 2'-O-methyl RNA residues with a phosphorothioate linkage between the flanking RNA residues. The oligonucleotides were provided in a 96-well plate, as well as matching tubes, with a minimum of 12 ODs of nucleobase oligomer, which provided ample material for transfections (greater than a hundred assays in the 96-well format) when the detection method is a sensitive method, such as TaqMan quantitative PCR, or an ELISA. Once the positive hits were identified (see below), oligonucleotides were re-synthesized with three, instead of two, flanking RNA residues to further increase stability/nuclease resistance. In addition, for validation purposes, appropriate controls (such as scrambled, 4-base mismatch, and reverse polarity oligonucleotides) were synthesized for some of the targets that yielded the highest activity.

EXAMPLE 3

Screening Assays and Optimization of Nucleobase Oligomers

Our approach to identifying nucleobase oligomers capable of inhibiting expression of an IAP was to screen the above-described oligonucleotide libraries for specific decreases (knock-down) of the RNA and/or protein for the specific IAP gene targeted. Any number of standard assays may be used to detect RNA and protein levels in cells. For example, RNA levels can be measured using standard northern blot analysis or RT-PCR techniques. Protein levels can be measured, for example, by standard western blot analyses or immunoprecipitation techniques. Alternatively, cells administered an antisense IAP nucleic acid may be examined for cell viability, according to methods described, for example, in U.S. Pat. Nos. 5,919,912, 6,156,535, and 6,133,437, incorporated herein by reference.

We used TaqMan quantitative PCR (described below) to assay for changes in mRNA levels after oligonucleotide treatment. We employed ELISA for determining XIAP protein levels and western blotting for determining HIAP1 protein levels. Transfection conditions were optimized with Lipofectamine plus or Lipofectamine 2000 (Life Technologies, Canada) on T24 bladder carcinoma cells or H460 non-small cell lung carcinoma cells, or lipofectin on SF-295 glioblastoma cells, using a fluorescein-tagged sense oligonucleotide (5'-mGmAGAAGATGACTGGTAAmCmA-3'; SEQ ID NO:

261) from XIAP spanning the start codon as a control. The results were visualized and gauged by epi-fluorescence microscopy. In the case of T24 cells, transfections were further optimized based on the ability of a published oligonucleotide to downregulate survivin expression (Li et al., Nat. Cell Biol. 1:461-466, 1999) (5'-U/TGTGCTATTCTGTGAA U/TU/T-3' SEQ ID NO: 262). We optimized the transfection conditions based on the TaqMan results of survivin RNA knock-down detected with PCR primers and fluorescent probe, described in detail below. Optimal conditions for oligonucleotide uptake by the cells were found to be 940 nM oligonucleotide and 4 µL PLUS reagent and 0.8 µL Lipofectamine in a total of 70 µL for three hours. We then applied these conditions to screen for XIAP protein knock-down using the oligo library against T24 cells.

HIAP1 knock-down was studied in SF-295 cells because these cells had easily detectable and discernable 70 kDa HIAP1 protein, while many cell lines do not express high levels of the protein, or are not distinguishable from the large amounts of the similarly sized 68 kDa HIAP2 protein.

Real-Time PCR

RNA was extracted from cells lysed in RLT buffer (QIAGEN, Valencia, Calif.), and purified using QIAGEN RNeasy columns/kits. Real-time quantitative PCR was performed on a Perkin-Elmer ABI 7700 Prism PCR machine. RNA was reverse transcribed and amplified according to the TaqMan Universal PCR Master Mix protocol of PE Biosystems, using primers and probes designed to specifically recognize XIAP, HIAP1, survivin, or GAPDH. For human survivin, the forward primer was 5'-TCTGCTTCAAGGAGCTGGAA-3' (SEQ ID NO: 263), the reverse primer was 5'-GAAAGGAAAGCGCAACCG-3' (SEQ ID NO: 264), and the probe was 5'-(FAM)AGCCA-GATGACGACCCCATAGAGGAACATA(TAMRA)-3' (SEQ ID NO: 265). For human HIAP1, the forward primer was 5'-TGGAGATGATCCATGGGTTCA-3' (SEQ ID NO: 266), the reverse primer was 5'-GAACTCCTGTCCTT-TAATTCTTATCAAGT-3' (SEQ ID NO: 267), and the probe was 5'-(FAM)CTCACACCTTGGAAACCACTTGGCATG (TAMRA)-3' (SEQ ID NO: 268). For human XIAP, the forward primer was 5'-GGTGATAAAGTAAAGT-GCTTTCACTGT-3' (SEQ ID NO: 269), the reverse primer was 5'-TCAGTAGTTCTTACCAGACACTCCTCAA-3' (SEQ ID NO: 270), and the probe was 5'-(FAM)CAACAT-GCTAAATGGTATCCAGGGTGCAAATATC(TAMRA)-3' (SEQ ID NO: 271). For human GAPDH, the forward primer was 5'-GAAGGTGAAGGTCGGAGTC-3' (SEQ ID NO: 272), the reverse primer was 5'-GAAGATGGTGATGG-GATTC-3' (SEQ ID NO: 273), and the probe was 5'-(JOE) CAAGCTTCCCGTTCTCA GCC(TAMRA)-3' (SEQ ID NO: 274). FAM is 6-carboxyfluoroscein, JOE is 6-carboxy-4,5-dichloro-2,7-dimethoxyfluoroscein, and TAMRA is 6-carboxy-N,N,N',N'-tetramethylrhodamine. FAM and JOE are 5' reporter dyes, while TAMRA is a 3' quencher dye.

Relative quantification of gene expression was performed as described in the PE Biosystems manual using GAPDH as an internal standard. The comparative Ct (cycle threshold) method was used for relative quantitation of IAP mRNA levels compared to GAPDH mRNA levels. Briefly, real-time fluorescence measurements were taken at each PCR cycle and the threshold cycle (Ct) value for each sample was calculated by determining the point at which fluorescence exceeded a threshold limit of 30 times the baseline standard deviation. The average baseline value and the baseline SD are calculated starting from the third cycle baseline value and stopping at the baseline value three cycles before the signal starts to expo-nentially rise. The PCR primers and/or probes for the specific IAPs were designed to span at least one exon-intron boundary separated by 1 kb or more of genomic DNA, to reduce the possibility of amplifying and detecting genomic DNA contamination. The specificity of the signal, and possible contamination from DNA, were verified by treating some RNA samples with either DNase or RNase, prior to performing the reverse transcription and PCR reaction steps.

XIAP ELISA and HIAP1 Western Immunoblots

A standard colorimetric XIAP ELISA assay was performed using an affinity-purified rabbit polyclonal antibody to XIAP as a capture antibody, and was detected with a XIAP monoclonal antibody (MBL, Japan) and a biotinylated anti-mouse Ig antibody and horseradish peroxidase-conjugated streptavidin and TMB substrate. Alternatively, a polyclonal XIAP or HIAP1 antibody may be used to measure XIAP or HIAP1 protein levels, respectively.

HIAP1 was detected on a western immunoblot using an affinity-purified anti-rat HIAP1 rabbit polyclonal antibody as a primary antibody and was detected by ECL (Amersham) on X-ray film with a secondary horseradish-peroxidase-conjugated anti-rabbit Ig antibody and a chemiluminescent substrate. The anti-HIAP1 polyclonal antibody is raised against a GST-fusion of the rat HIAP1. This antibody cross-reacts with both human and murine HIAP1 and HIAP2.

EXAMPLE 4

Antisense XIAP Oligonucleotides Decrease XIAP RNA and Polypeptide Expression

The XIAP synthetic library of 96 antisense oligonucleotides was first screened for decreases in XIAP protein levels. Specifically, T24 cells ($1.5 \times 10^4$ cells/well) were seeded in wells of a 96-well plate on day 1, and were cultured in antibiotic-free McCoy's medium for 24 hours. On day 2, the cells were transfected with XIAP antisense oligonucleotides as described above (oligonucleotides are labeled according to their plated position, i.e., A1 to H12, and include two repeats, A13 and B13 that contain lyophilized DNA pellets that stuck to the sealing membrane). Briefly, the nucleobase oligomers were diluted in 10 µl/well of serum-free, antibiotic-free McCoy's medium and then PLUS reagent was added. Lipofectamine was diluted in 10 µl/well of serum-free, antibiotic-free McCoy's medium, and both mixes were incubated for 15 minutes at room temperature. The mixes were then combined and incubated for 15 minutes at room temperature.

In the meantime, the complete medium was removed from the cells and 50 µl/well of serum-free, antibiotic-free medium was added to the cells. The transfection mixes were added to the well, and the cells were incubated for three hours. Then 30 µl/well of serum-free, antibiotic-free medium and 100 µl/well of antibiotic-free complete medium, containing 20% fetal bovine serum were added to each well.

At day 3, XIAP RNA levels were measured using quantitative real-time PCR techniques, as described above. At day 4, XIAP protein levels were measured by ELISA (FIGS. 1A, 1C, 1E, 1G, 1I, and 1K), and total cellular protein was measured biochemically (FIGS. 1B, 1D, 1F, 1H, 1J, and 1L; used to normalize the XIAP protein levels). The results were compared to a mock transfection sample (treated with the transfection agent but no oligonucleotide DNA was added, and then processed as for the other samples). Time course experiments determined that the optimal time for protein knock-down to be around 12 to 24 hours.

The oligonucleotide library was also screened for decreases in RNA levels, using TaqMan-specific PCR primers and fluorescent probes at the appropriate optimal time, using the primers and probes described above. Time course experiments determined mRNA to be optimally decreased at 6 to 9 hours. These results agree well with the protein results.

The first screen (although performed at a sub-optimal time point when XIAP levels are returning to normal, possibly due to an outgrowth of non-transfected cells) identified 16 antisense oligonucleotides (Table 1: C2, E2, E3, F3, C4, D4, E4, F4, G4, C5, D5, B6, F6, D7, D8, F8) out of the 96 nucleobase oligomers tested that showed some decrease in XIAP protein levels relative to total protein, compared to mock (no nucleobase oligomer) transfection levels (FIGS. 1A, 1C, 1E, 1G, 1I, and 1K). Total protein was decreased for each of these 16 nucleobase oligomers, which indicates a toxic or cytostatic effect of these nucleobase oligomers (FIGS. 1B, 1D, 1F, 1H, 1J, 1L). Nucleobase oligomers B9 and C9 showed a clear drop in total protein but no relative drop in XIAP protein levels.

Figure 2C:
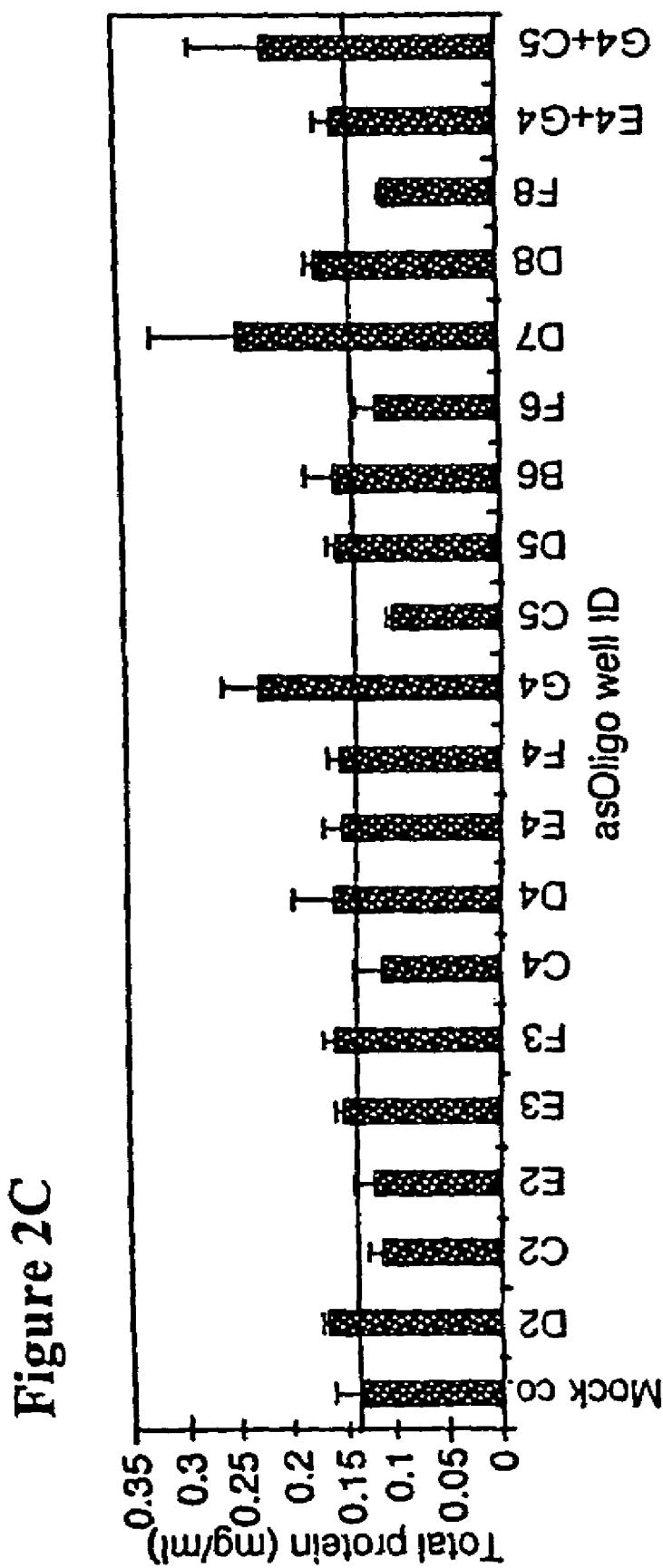

The 16 antisense nucleobase oligomers that showed some decrease in relative XIAP protein levels compared to mock transfection, were re-tested alone or in combination, with one control nucleobase oligomer (D2) included, for their ability to knock-down XIAP protein at a more optimal time point (12 hours) based on the above described time course studies (FIG. 2B). These nucleobase oligomers were also examined for their ability to decrease XIAP mRNA levels at 12 hours, normalized against GAPDH levels, and compared to mock transfection. Total protein concentrations at 12 hours were also determined (FIG. 2C).

There was a good correlation between the ability of a nucleobase oligomer to decrease XIAP protein levels (FIG. 2B) with its ability to decrease XIAP mRNA levels (FIG. 2A). In addition, there is no major loss of total protein at this early time point, and the decrease in XIAP mRNA and protein precede the decrease in total protein that is seen at later time points. The nucleobase oligomers that showed greater than 50% loss of XIAP protein or mRNA levels alone, or in a combination of two nucleobase oligomers added at a 1:1 ratio, were identified as the best nucleobase oligomers and validated further. Of these 16 oligonucleotides, ten (E2, E3, F3, E4, F4, G4, C5, B6, D7, F8) showed a consistent ability to decrease XIAP protein or RNA levels by more than 50%, depending on the transfection conditions used, or when used in combination (as for C5 and G4). Moreover, these 16 oligonucleotides that demonstrated antisense activity clustered in four different target regions of the XIAP mRNA, with adjacent nucleobase oligomers showing some knock-down activity. Little or no antisense activity was observed with nucleobase oligomers that target sequences between these regions or islands of sensitivity. Presumably, these regions represent open areas on the mRNA that are accessible to nucleobase oligomers inside the cell. Two nucleobase oligomers, E3 and F3, target XIAP just upstream of the start codon in the intervening region between the IRES and the translation start site, and partially overlap the end of the IRES element. C2, D2, and E2 target a XIAP region upstream of the minimal IRES element, providing further evidence that the minimal IRES region is a highly structured region of RNA that is not readily accessible to nucleobase oligomers in vivo. All the other nucleobase oligomers are complimentary to a portion of the coding region, including a cluster of activity at positions 856-916 of the XIAP sequence (E4, F4, and G4) and smaller separate areas, as demonstrated by nucleobase oligomers C5 and D5, for example.

A portion of the 96 nucleobase oligomers depicted in Table 1 were rescreened for their ability to knock-down XIAP mRNA in NCI-H460 cells at 9 hours post-transfection. The data are summarized in Table 4, below.

TABLE 4

| 2 × 2 MBO | XIAP RNA | Std. Dev. |
|---|---|---|
| Untrf. Co. | 1.04 | 0.055 |
| Mock Co. | 1.01 | 0.006 |
| G4 sm | 0.97 | 0.071 |
| DE4 rev | 1.06 | 0.121 |
| A1 as | 0.46 | 0.01 |
| B1 as | 0.34 | 0.03 |
| C1 as | 0.3 | 0.04 |
| D1 as | 0.25 | 0.03 |
| E1 as | 0.31 | 0.01 |
| F1 as | 0.19 | 0.01 |
| G1 as | 0.67 | 0.03 |
| H1 as | 0.87 | 0.03 |
| A2 as | 0.42 | 0.02 |
| B2 as | 0.45 | 0.03 |
| C2 as | 0.33 | 0.02 |
| D2 as | 0.66 | 0.01 |
| E2 as | 0.44 | 0.01 |
| F2 as | 0.64 | 0.02 |
| G2 as | 0.44 | 0.01 |
| H2 as | 0.56 | 0.04 |
| A3 as | 0.71 | 0.03 |
| B3 as | 0.64 | 0.08 |
| C3 as | 0.55 | 0.04 |
| D3 as | 0.68 | 0.02 |
| E3 as | 0.48 | 0.02 |
| B4 as | 0.23 | 0.01 |
| C4 as | 0.22 | 0.04 |
| D4 as | 0.48 | 0.04 |
| E4 as | 0.44 | 0.01 |
| G4 as | 0.48 | 0.02 |
| B5 as | 0.38 | 0.03 |
| E5 as | 0.52 | 0.05 |
| G5 as | 0.68 | 0.05 |
| H5 as | 0.59 | 0.09 |
| A6 as | 0.27 | 0 |
| D6 as | 0.39 | 0.03 |
| G6 as | 0.3 | 0.01 |
| H6 as | 0.31 | 0.01 |
| C7 as | 0.27 | 0.02 |
| D7 as | 0.52 | 0.04 |
| F7 as | 0.3 | 0.04 |
| G7 as | 0.66 | 0.04 |
| H7 as | 0.49 | 0.01 |
| C8 as | 1.01 | 0.08 |
| D8 as | 0.55 | 0.04 |
| F8 as | 0.62 | 0 |
| G8 as | 0.64 | 0.06 |
| H8 as | 0.61 | 0.06 |
| A9 as | 0.46 | 0.02 |
| B9 as | 0.74 | 0.07 |
| D9 as | 0.73 | 0.04 |
| E9 as | 0.69 | 0.06 |
| F9 as | 0.97 | 0.15 |
| A10 as | 0.85 | 0.04 |
| C10 as | 0.56 | 0.01 |
| D10 as | 0.54 | 0.01 |
| F10 as | 0.64 | 0 |
| G10 as | 0.49 | 0 |
| A11 as | 0.36 | 0.03 |
| B11 as | 0.39 | 0.02 |
| C11 as | 0.44 | 0.03 |
| E11 as | 0.52 | 0.04 |
| F11 as | 0.36 | 0.05 |
| G11 as | 0.67 | 0.02 |
| A12 as | 0.54 | 0.03 |
| D12 as | 0.23 | 0.05 |
| E12 as | 0.26 | 0.01 |
| F12 as | 0.26 | 0.03 |
| G12 as | 0.24 | 0.05 |
| H12 as | 0.48 | 0.06 |

Figure 3:
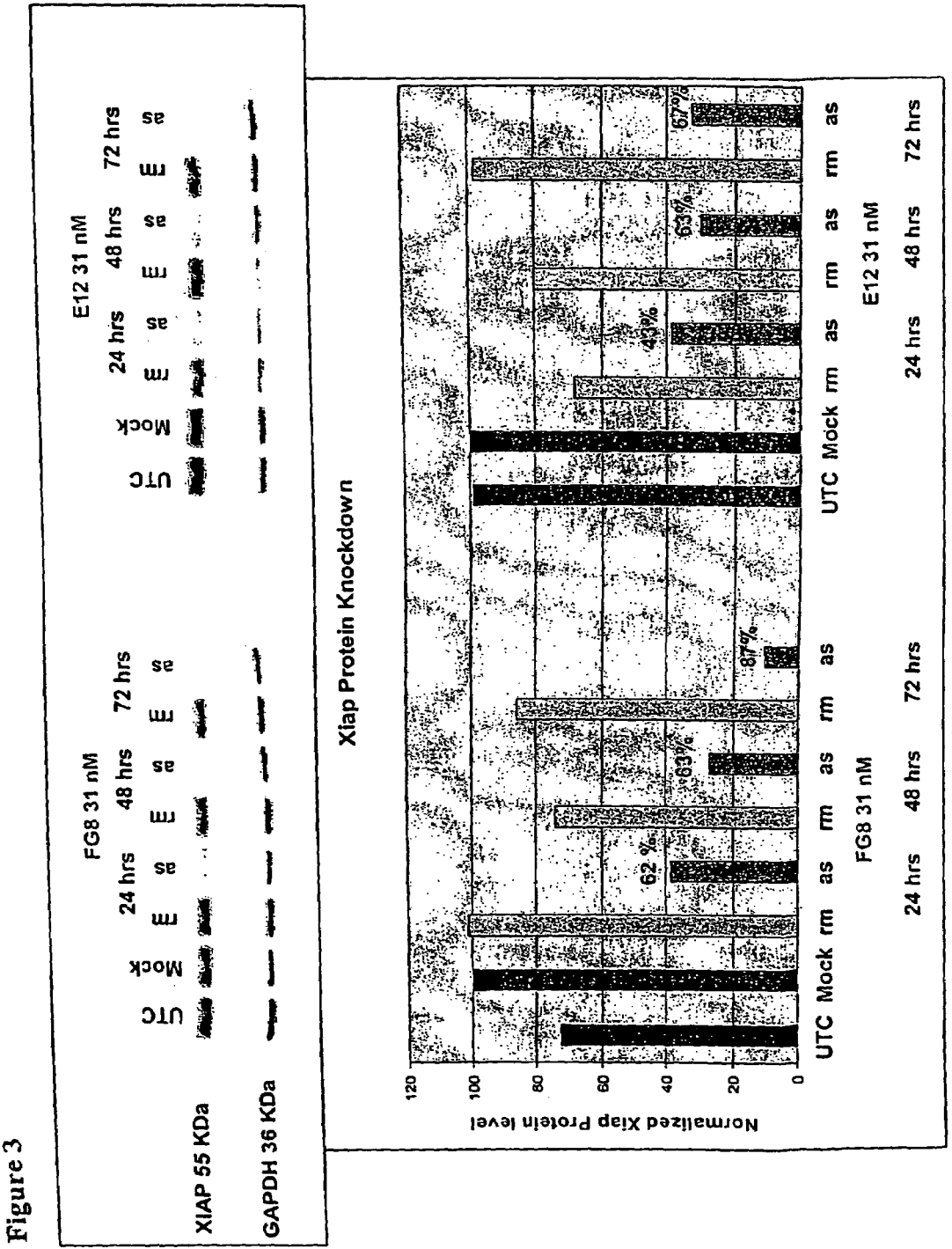
FIGS. 3 and 4 are graphs showing the effects of 4×4 mixed backbone (MBO) FG8 or E12 oligonucleotides in amounts of 31 nM (FIG. 3) or 63 nM (FIG. 4). H460 lung carcinoma cells were transfected for 18 hours on one, two, or three consecutive days using 125 nM MBOs and Lipofectamine 2000. Samples for western analysis were harvested at the indicated time. Scanning densitometry was performed, and XIAP protein levels were normalized to GAPDH and compared to a mock control set to 100%. The indicated percentages express % XIAP protein knockdown versus specific scrambled controls.
Figure 4:
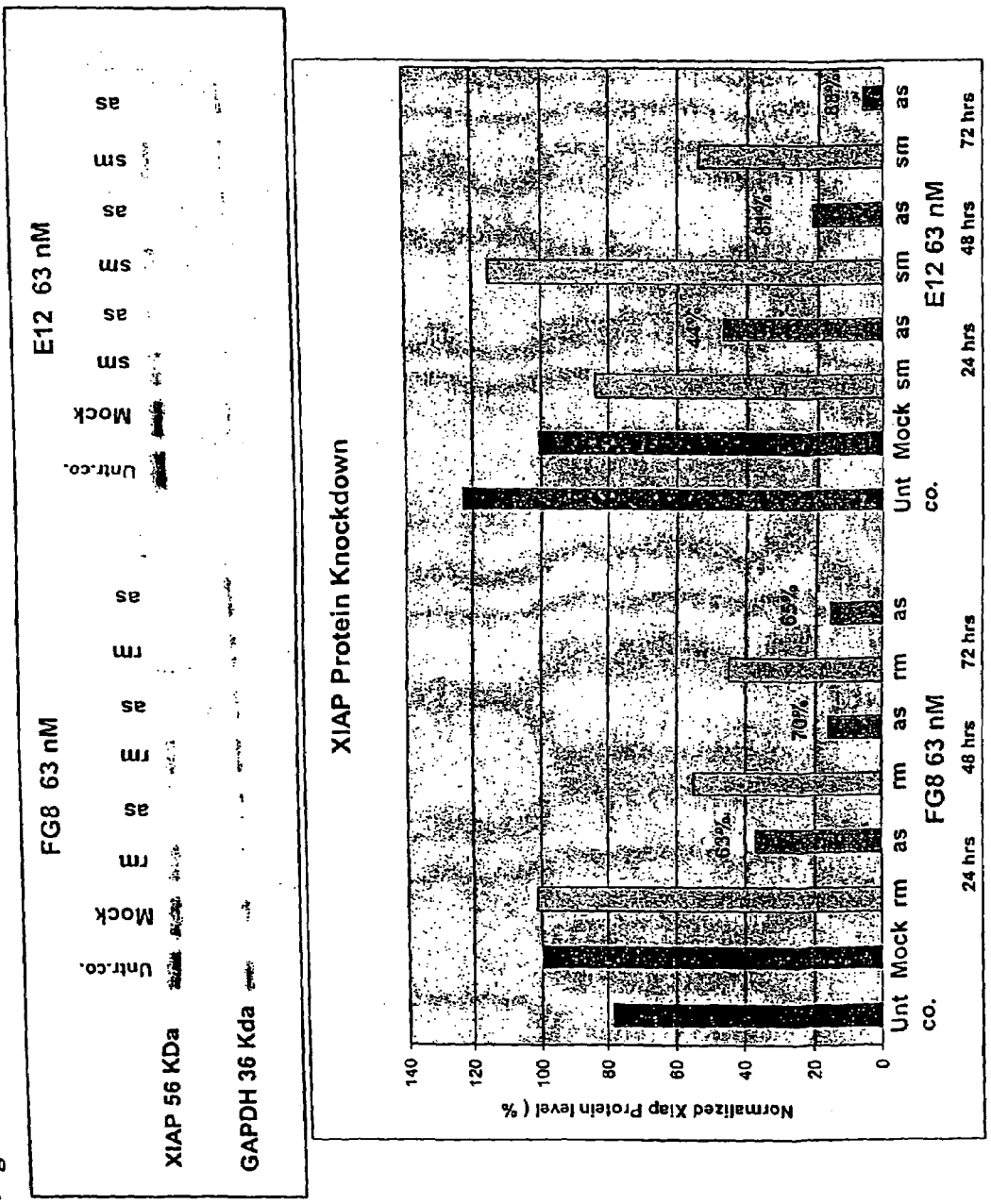

We also determined whether 4×4 MBOs (all PS, DNA residues flanked on both sides by four 2'-O-methyl RNA residues) were capable of knocking-down XIAP protein in H460 cells. As shown in FIGS. 3 and 4, 4×4 MBs of E12 and another oligonucleotide, FG8, were effective in amounts as low as 31 nM.

EXAMPLE 5

XIAP Antisense Nucleobase Oligomers Increase Cytotoxicity and Chemosensitization We investigated if XIAP antisense nucleobase oligomers could chemosensitize the highly drug resistant T24 cells to traditional chemotherapeutic agents, such as adriamycin or cisplatin. Antisense oligonucleotides were chosen to represent some of the different XIAP target regions and tested for their cytotoxic effects, alone or in combination with other oligonucleotides or drugs. Five XIAP antisense oligonucleotides were tested for their ability to kill or chemosensitize T24 bladder carcinoma cells, and were compared to the effects of three corresponding scrambled control oligonucleotides.

Figure 5A:
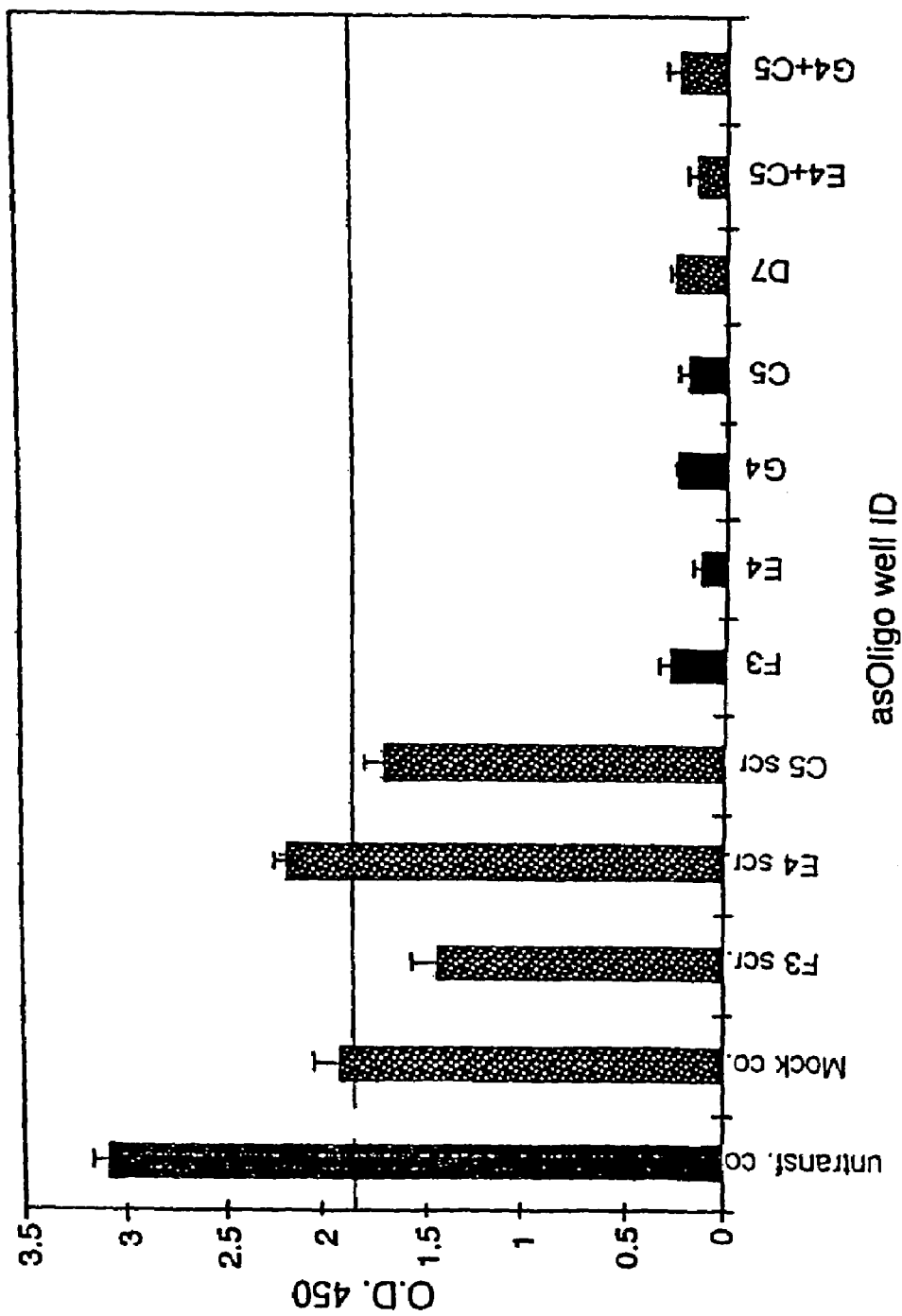
FIGS. 5A-5D are graphs of the effects of antisense XIAP oligonucleotides on cell viability (FIGS. 5A, 5C, and 5D), and chemosensitization in the presence of adriamycin (FIG. 5B).

T24 cells were transfected with XIAP antisense oligonucleotides, scrambled oligonucleotides, no oligonucleotides (mock transfected), or were left untreated. The cells were tested for viability 20 hours after transfection (with the exception of the untreated control) using the WST-1 tetrazolium dye assay in which WST-1 tetrazolium dye is reduced to a colored formazan product in metabolically active cells (FIG. 5A).

Figure 5B:
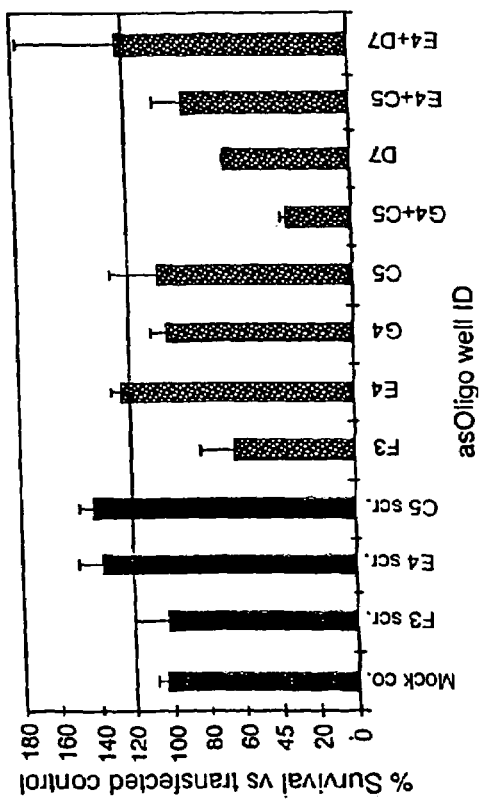

The occurrence of cytotoxicity induced by oligonucleotide E4 was examined by visually inspecting T24 cells that were left untreated, mock transfected, or transfected with E4, E4 scrambled, E4 reverse polarity, or E4 mismatched oligonucleotides. Twenty hours after transfection, the cells were examined for morphology (FIG. 5D). Only the cell transfected with antisense E4 oligonucleotides showed signs of toxicity.

To examine the effects of the nucleobase oligomers on the chemosensitization of the T24 cells to cisplatin or adriamycin, oligonucleotides were tested for their ability to further kill T24 cells in the presence of a fixed dose of adriamycin (0.5 µg/ml). Cells were first transfected with a oligonucleotide, then adriamycin was added for another 20 hours. Viability was measured by WST-1 at the end of the 20-hour drug treatment (FIG. 5B). Results are shown in FIG. 5C as percentage viability compared to nucleobase oligomer treatment alone.

All five nucleobase oligomers tested (F3, E4, G4, C5, D7) as well as combinations of E4+C5 and G4+C5, killed the T24 cells, leaving only 10-15% surviving cells after 24 hours, as compared to the mock (no oligonucleotide) transfected cells, or to cells transfected with three corresponding scrambled controls to F3 (5'-mCmAmGAGATTTCATTTAAmC-mGmU-3'; SEQ ID NO: 275), E4 (5'-mCmUmACGCTCGC-CATCGTm UmCmA-3'; SEQ ID NO: 276) and C5 (5'-mUmGmCCCAAGAATACTAGmUmC mA-3'; SEQ ID NO: 277)(FIGS. 5A and 5C). Therefore, the toxicity is sequence-specific to those nucleobase oligomers that reduce XIAP levels, and not to a non-sequence specific toxicity due to nucleobase oligomers this chemistry in general. This cytotoxicity may result from the combined effect of XIAP protein knock-down (and the expected loss of anti-apoptotic protection afforded by XIAP) and the cytotoxicity of the transfection itself.

Figure 5C:
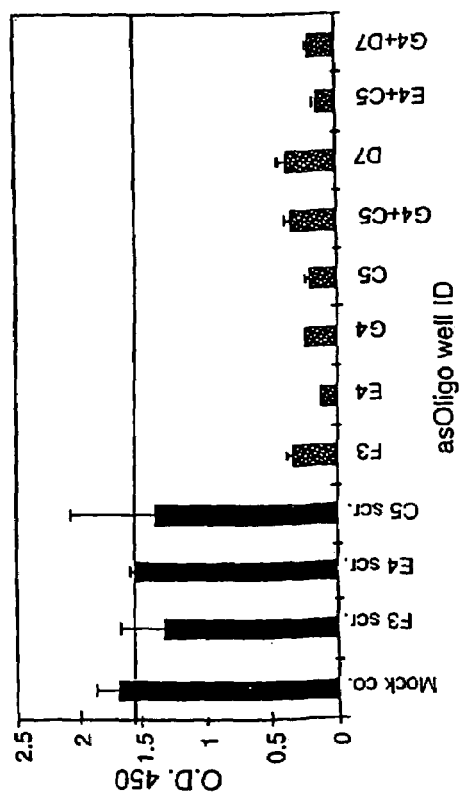
Figure 5D:
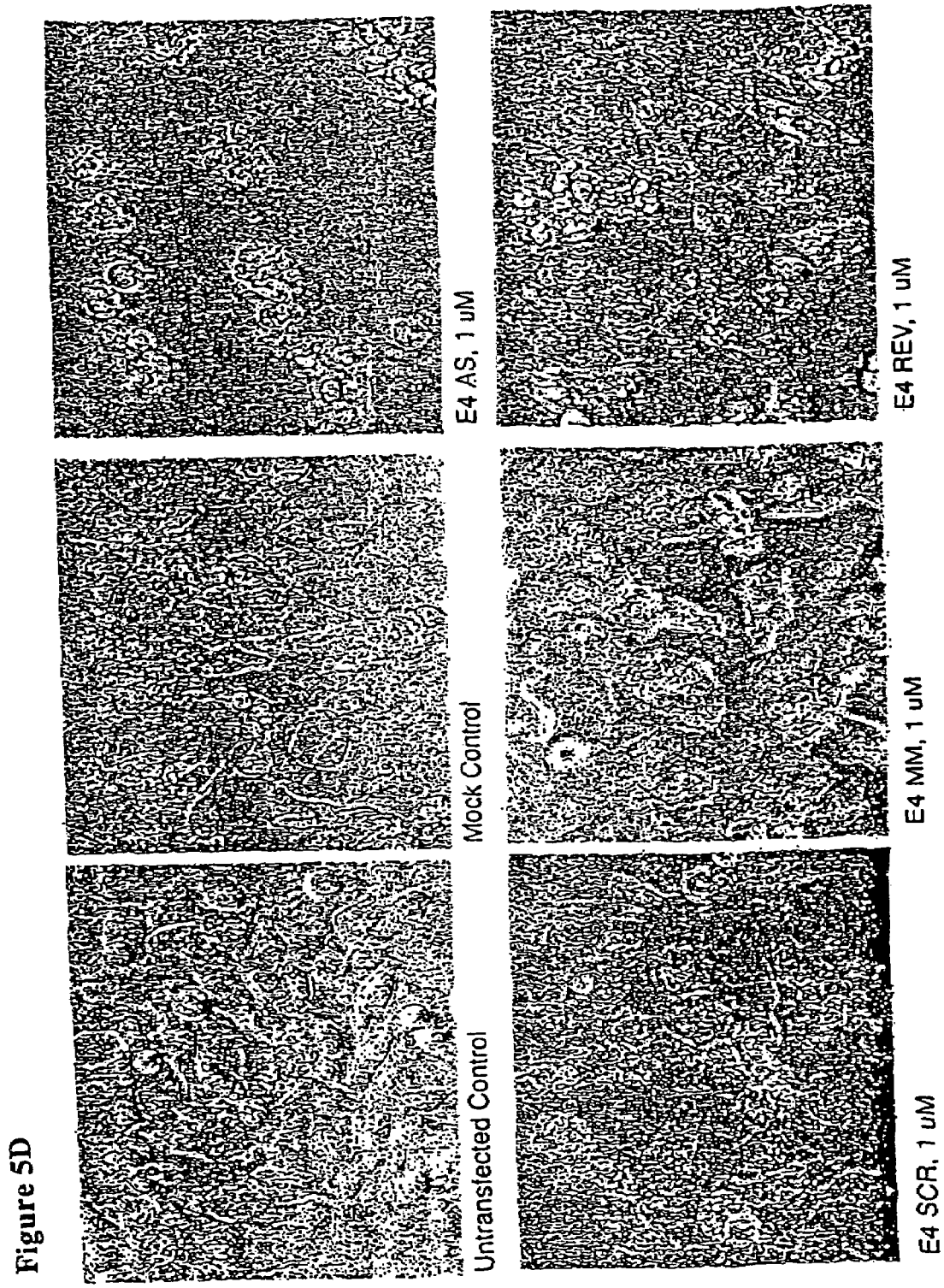

The addition of a fixed dose of adriamycin or cisplatin at the end of the three hour transfection period resulted in a further decrease in survival for some of the tested oligonucleotides, a further 40% drop in survival after 20 hours for nucleobase oligomers F3, D7 and G4+C5 combination (FIG. 5B), compared to their corresponding oligonucleotide-treated values (FIG. 5C). The values in FIG. 5B (oligonucleotide plus drug) are compared to the values of oligonucleotide alone in FIG. 5C, which is set a 100% for each ODN. Only the results for adriamycin chemosensitization are shown; similar results were obtained when the cells were chemosensitized with cisplatin. At the fixed doses used, the mock and scrambled control transfections did not show any increased loss of survival when either treated with adriamycin (FIG. 5B). Chemosensitization is only seen when XIAP levels are decreased by a specific antisense oligonucleotide.

EXAMPLE 6

Figure 6:
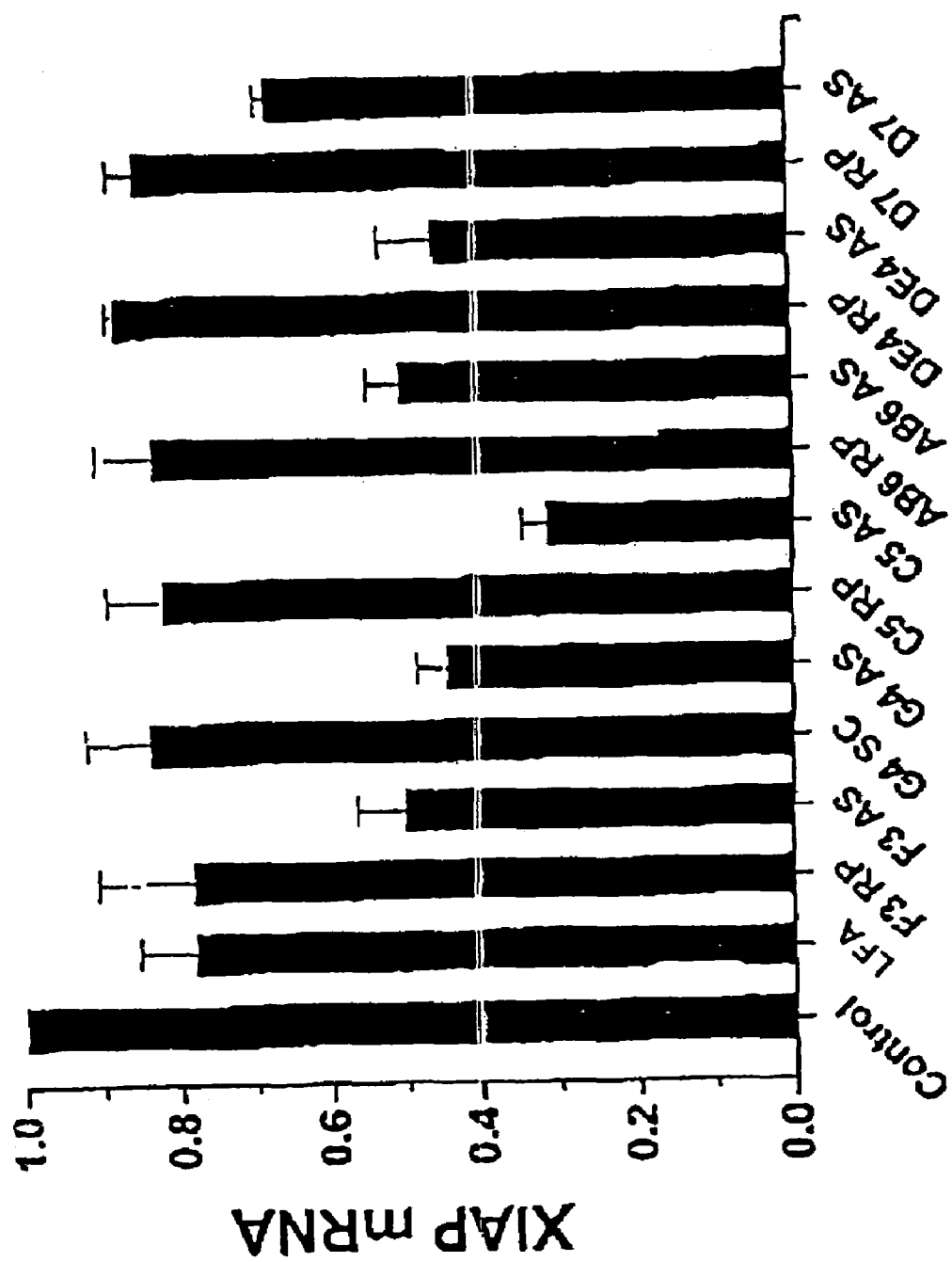
FIG. 6 is a graph showing oligonucleotide-mediated specific down-regulation of XIAP mRNA in H460 cells in vitro. Depicted are XIAP mRNA levels in H460 cells treated with Lipofectamine 2000 alone (LFA) or Lipofectamine 2000 with 1.2 □M of oligonucleotides F3, G4, C5, AB6, DE4 or D7, or a respective reverse polarity (RP) or scrambled (SC) oligonucleotide control. Real-time RT-PCR quantification of the relative amount of XIAP mRNA was performed at 6 hours of transfection. All data are presented as the mean±standard deviation (SD) of triplicates from a representative experiment. The level of XIAP mRNA in untreated cells (control) maintained under identical experimental conditions was assigned a value of 1.
Figure 7:
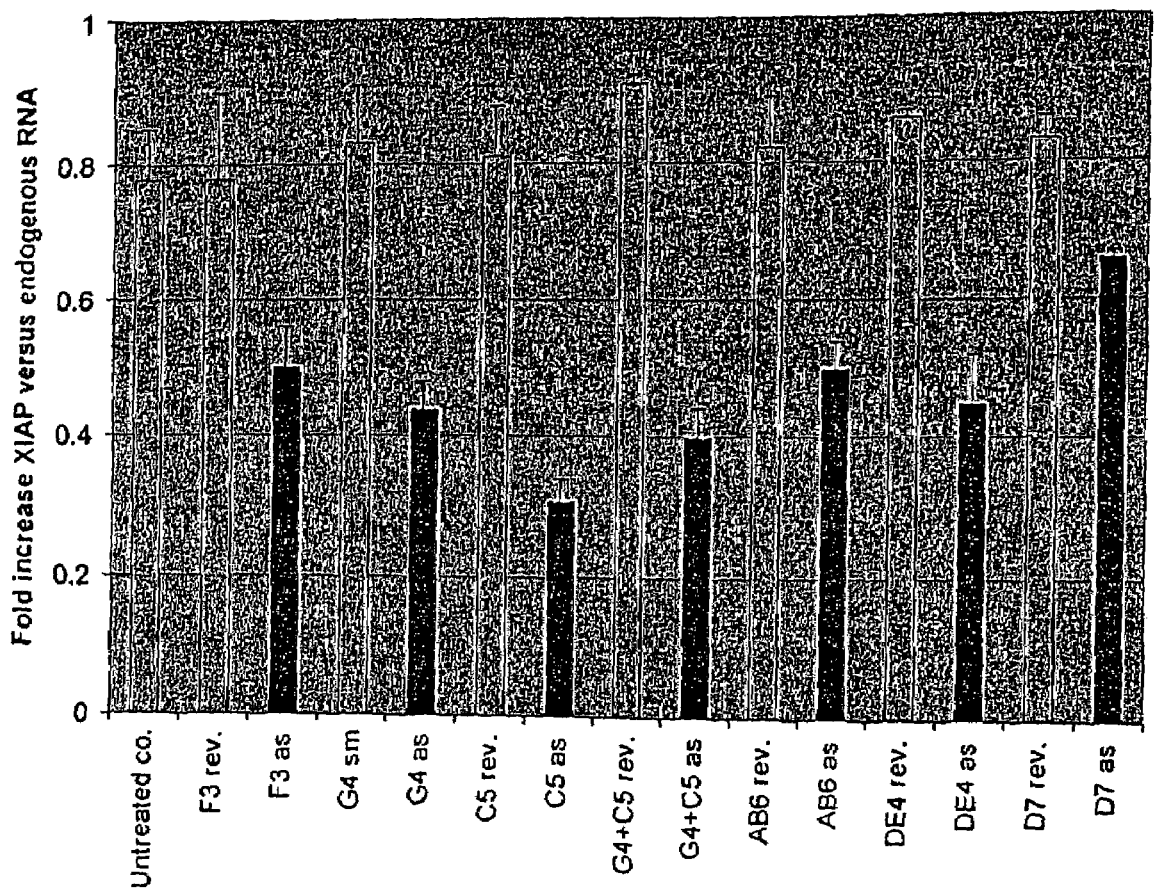
FIG. 7 is a graph showing XIAP RNA levels in H460 cells after transfection with various PS-XIAP oligonucleotides. H460 human lung cancer cells were transfected for 6 hours using 1 µM PS-oligonucleotides and Lipofectamine 2000. Cells were then harvested for Taqman analysis.
Figure 8:
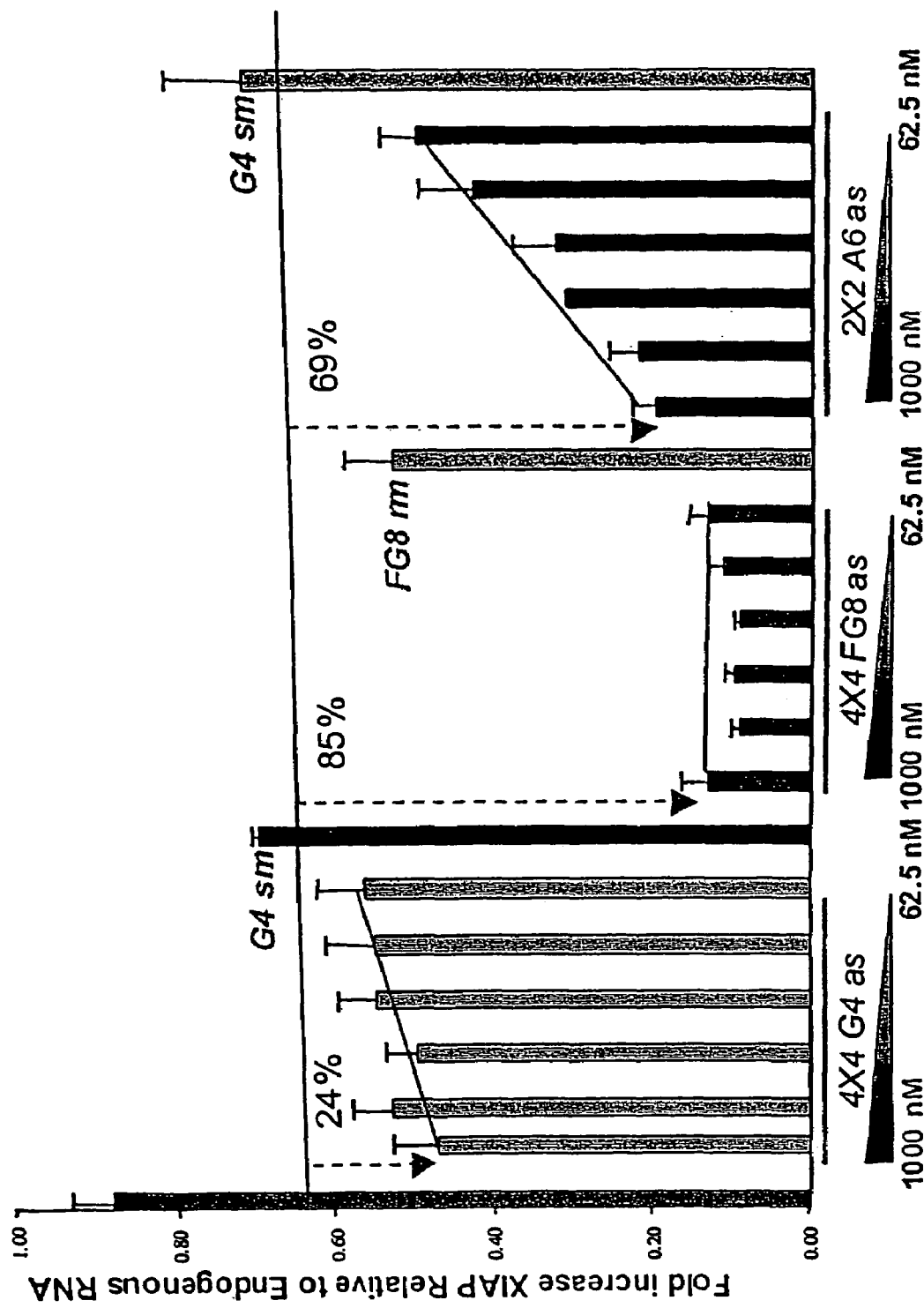
FIG. 8 is a graph showing XIAP RNA levels in H460 cells 9 hours post-transfection with 4×4 MBOs. H460 cells were transfected for 9 hours using 4×4 MBOs at 62.5 nM to 1 µM and Lipofectamine 2000. The cells were then harvested for Taqman analysis.

Down-Regulating Effects of Antisense Oligonucleotides on XIAP mRNA in H460 Cells By using real-time PCR, antisense oligonucleotides (2×2 MBO, composed of two flanking 2'-O-methyl RNA residues at either end with phosphorothioate linkages, and a central core of 15 phosphodiester DNA residues) were examined for their effects on XIAP mRNA in H460 cells. In this configuration, nucleobase oligomers F3, G4, C5, AB6 and DE4 reduced the mRNA level by 50-70%, compared to untreated control, while D7 AS nucleobase oligomers reduced the mRNA level by 30% (FIG. 6). In contrast, control nucleobase oligomers and transfectant agent alone (LFA) each only reduced the mRNA level to less than 20% of untreated control (FIG. 6). Nucleobase oligomers F3, G4 and C5 were selected for further study in vitro and in vivo. Additional knockdown of XIAP mRNA observed by TaqMan analysis is depicted in FIGS. 7 and 8.

EXAMPLE 7

Down-Regulating Effects of Antisense Oligonucleotides on XIAP Protein

Figure 9:
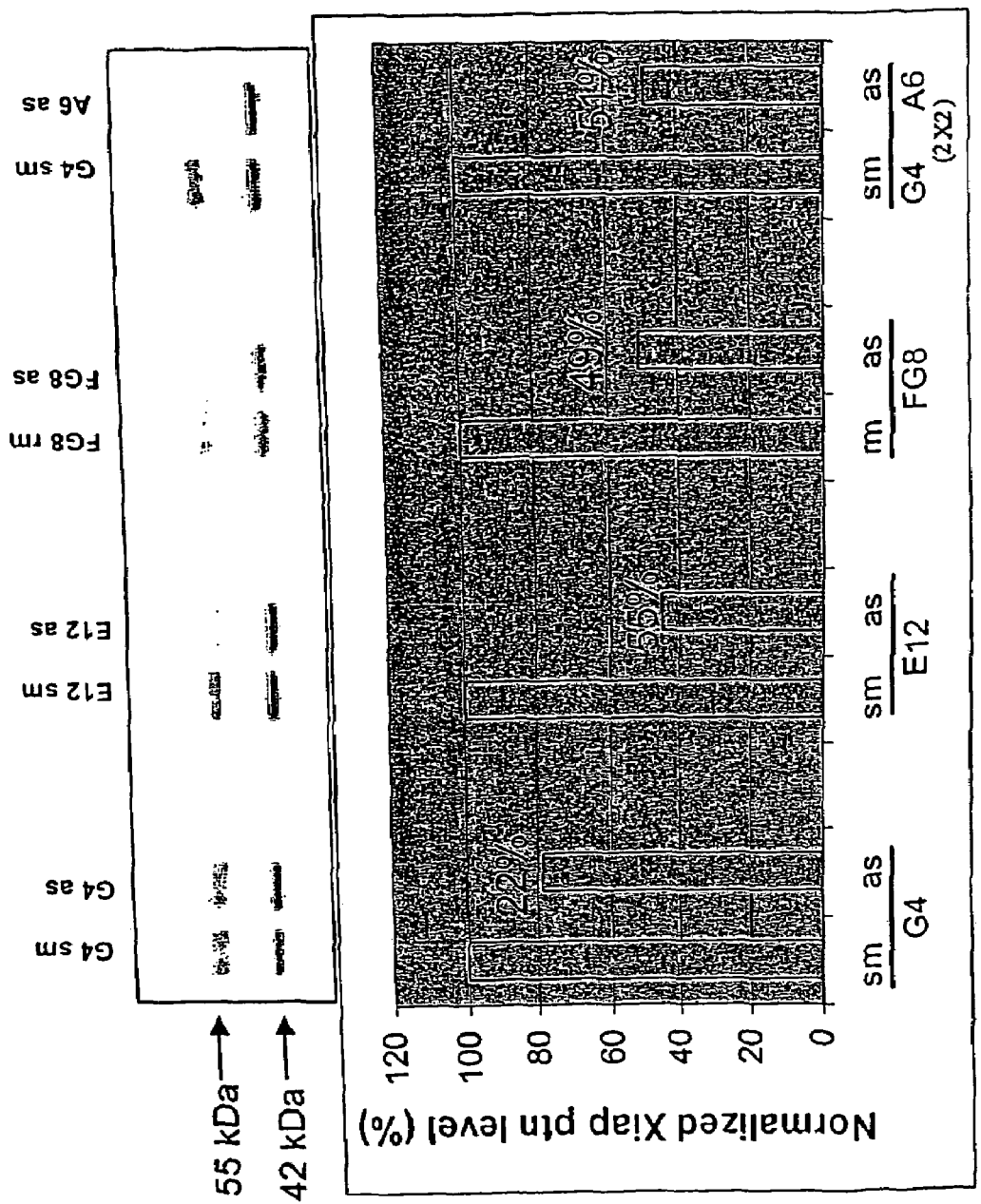
FIG. 9 is a graph showing XIAP protein knockdown in H460 cells 24 hours after transfection with 4×4 MBOs. H460 cells were transfected for 24 hours using 1 µM 4×4 MBOs at 1 µM and Lipofectamine 2000. The cells were then harvested for western blot analysis. Scanning densitometry was performed, and XIAP protein levels were normalized to actin and compared to their specific scrambled (sm, rm) controls, which were set at 100%.
Figure 10A:
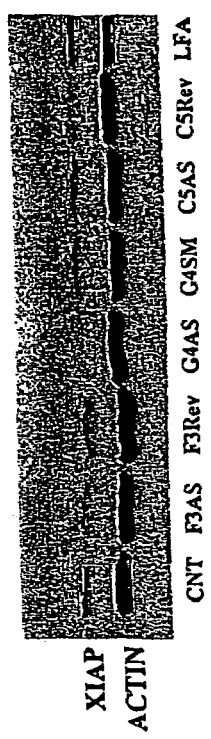
FIGS. 10A and 10B are schematic illustrations showing antisense-mediated specific downregulation of XIAP protein in H460 cells in vitro. Depicted are XIAP protein levels in H460 cells treated with Lipofectamine 2000 alone (LFA) or LFA plus 1.2 µM of XIAP oligonucleotides F3, G4, or C5, or their respective oligonucleotide controls (RP, SC). XIAP protein levels were analyzed by western blotting (FIG. 10A), and the amount of protein was quantified by densitometry (FIG. 10B). XIAP levels were normalized to cellular actin levels and compared to untreated control (CNT) levels.
Figure 10B:
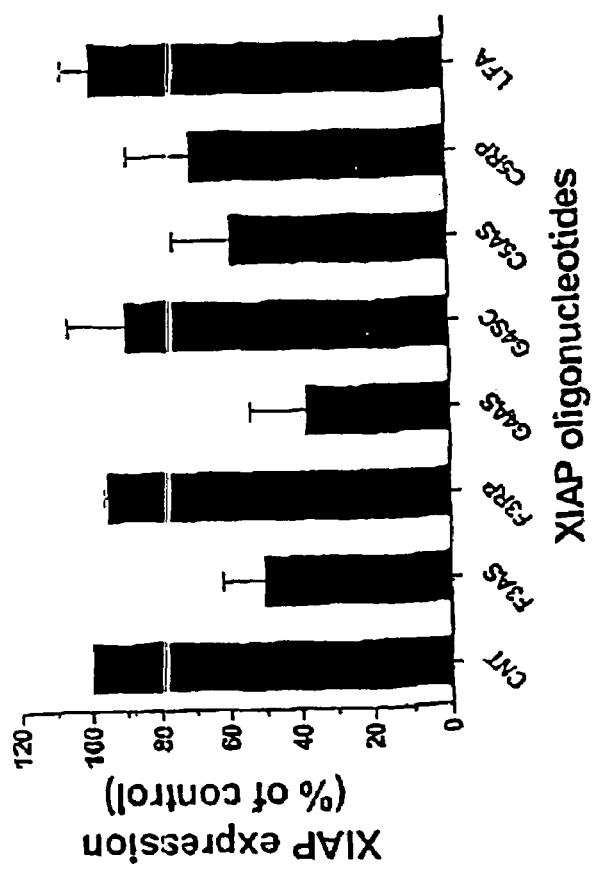

We characterized the potency of nucleobase oligomers F3, G4 and C5 in oligonucleotide configuration on the XIAP protein expression by western blot analysis (FIGS. 9, 10A, and 10B). G4 AS oligonucleotides exhibited the strongest down-regulating effect on XIAP protein, reducing XIAP protein levels by 62% at 24 h after the end of transfection at a concentration of 1.2 µM (FIGS. 10A and 10B). F3 AS oligonucleotides at 1.2 µM reduced XIAP protein level by 50%, while C5 AS oligonucleotides did not show sequence specific effects compared to its control (FIG. 10B). In additional studies, E12 and FG8 AS oligonucleotides significantly reduced XIAP protein levels (FIG. 9).

EXAMPLE 8

Induction of Apoptosis by XIAP as Oligonucleotides

Figure 11A:
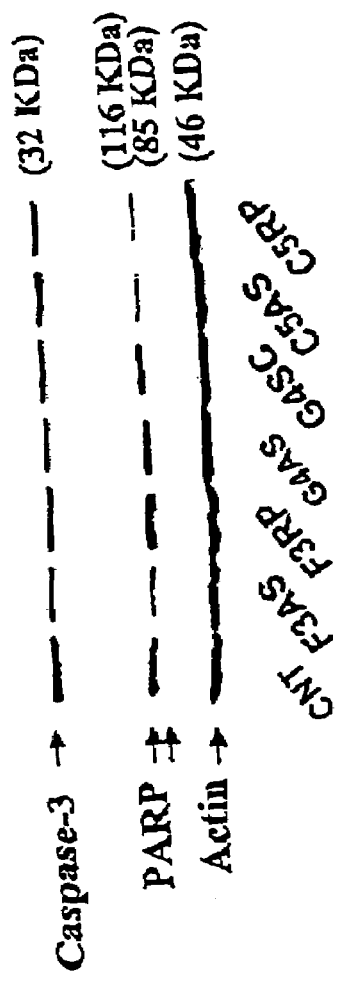
FIGS. 11A and 11B are schematic illustrations showing XIAP oligonucleotide-mediated effects on caspase activation. The effect of XIAP oligonucleotides F3, G4, or C5, or their respective RP and SC ODN controls at 1.2 µM on the expression of pro-caspase-3, PARP (both full length (116 kDa) and processed (85 kDa)) (FIG. 10A) and Bcl-2 and Bax protein levels (FIG. 10B) in transfected H460 cells compared to control is shown. Proteins expression was analyzed by western blotting. Bcl-2 and Bax protein levels were normalized to cellular actin levels and quantified by densitometry. The ratio of Bcl-2/Bax is presented as the mean of two or three independent experiments, and the ratio in control (CNT) cells set at 1.
Figure 11B:
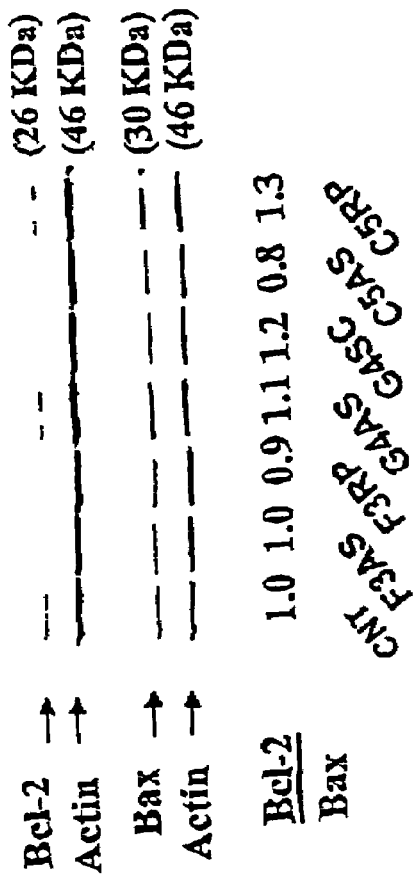
Figure 12:
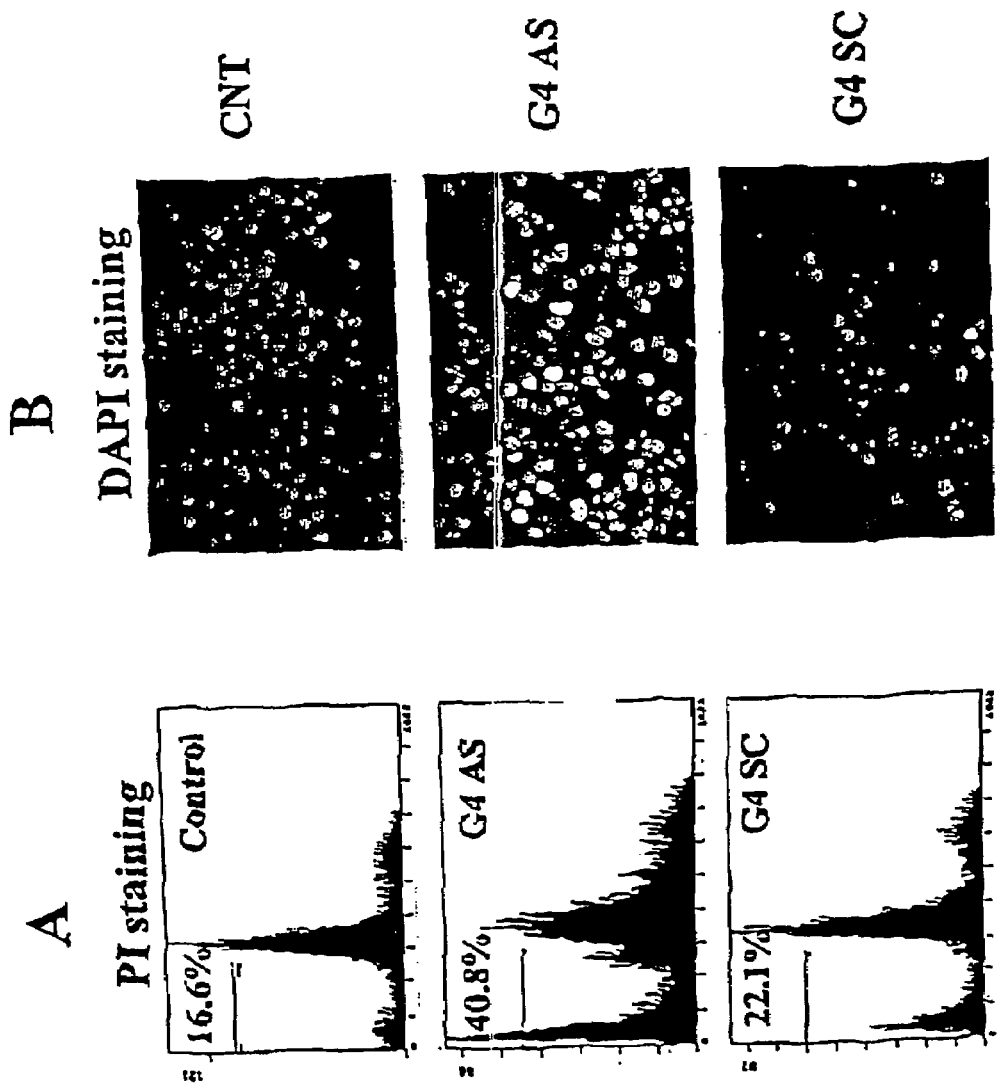
FIGS. 12A and 12B are schematic illustrations showing XIAP oligonucleotide-specific induction of apoptosis. Induction of apoptosis was measured in H460 cells treated with 1.2 µM of XIAP G4 AS oligonucleotide, G4 SC oligonucleotide or untreated control (CNT).

Having demonstrated that XIAP AS nucleobase oligomers were capable of reducing viability of H460 cells and T24 bladder carcinoma cells after, we determined whether the observed cell death was due to the induction of apoptosis. As shown in FIG. 11A, H460 cells treated with F3 or G4 AS oligonucleotides at 1.2 µM activated and degraded pro-caspase-3 protein with a reduction of 40% or 60% of protein levels, respectively, compared to untreated control cells. PARP was also to its predicted caspase-3-generated fragment (FIG. 11A). In contrast, F3 and G4 SC oligonucleotide controls at 1.2 µM did not have any effect on caspase-3 or PARP protein expression (FIG. 11A). The ratio of Bcl-2:Bax was unchanged in H460 cells treated with F3 and G4 AS oligonucleotides and their respective controls at 1.2 µM. Flow cytometry was used to detect the hypo-diploid DNA content in H460 cells treated with G4 AS oligonucleotides and stained with PI (FIG. 12A). When H460 cells were treated with G4 AS oligonucleotides or scrambled control oligonucleotides at 1.2 µM, the hypo-diploid DNA content of cells was 40.8 and 22.1%, respectively, compared to 16.6% for untreated control cells. DAPI staining was used to detect the nuclear morphological changes of the H460 cells treated with G4 AS oligonucleotides or scrambled control oligonucleotides at 1.2 µM. As shown in FIG. 12B, cells treated with G4 AS oligonucleotides underwent morphological changes characteristic of apoptosis, including chromatin condensation and nuclear DNA fragmentation. Few cells showed these morphological changes in G4 SC-treated control cells.

EXAMPLE 9

Figure 13A:
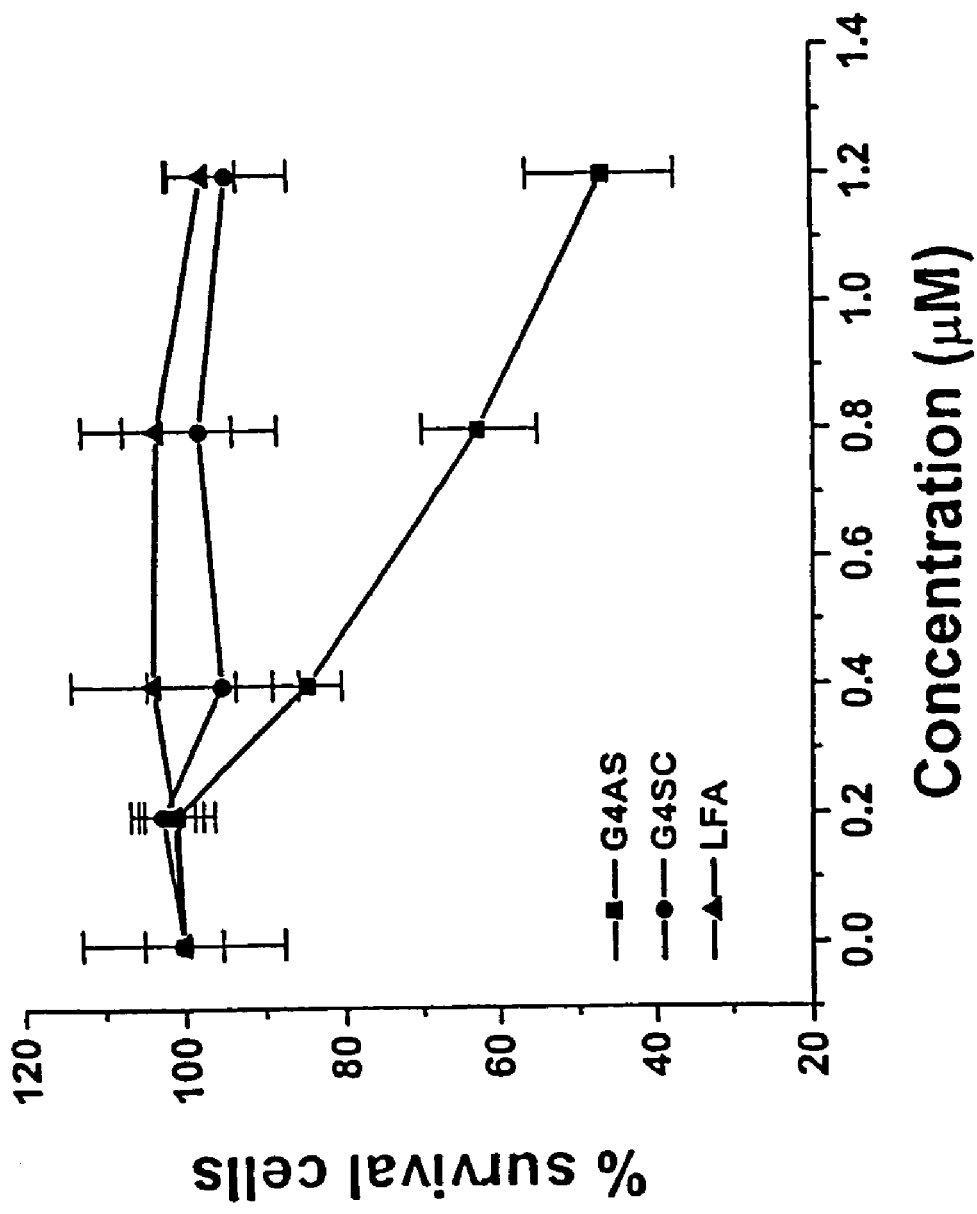
FIG. 13A is a graph showing the effect of XIAP G4 AS oligonucleotide treatment on the viability of H460 cells. Cells were treated with an increasing concentration of LFA alone or LFA-oligonucleotide complexes with G4 AS oligonucleotides or G4 SC oligonucleotides, and cells viability was determined by MTT assay after 24 hours of treatment. The data represent the mean±SD of three independent experiments.

Inhibition of Cell Growth and Sensitization of H460 Cells to Anticancer Agents by AS Oligonucleotides To analyze biological effects of nucleobase oligomers associated with down-regulation of XIAP expression and apoptosis, the growth of H460 cells treated with G4 AS oligonucleotides was investigated by MTT assay. Forty-eight hours after the transfection, G4 AS oligonucleotides had reduced H460 cell growth in a dose-dependent manner, exhibiting a 55% reduction relative to untreated control levels at 1.2 µM (FIG. 13A). In contrast, the growth-inhibitory effect of G4 SC oligonucleotides, or transfectant agent alone, was comparatively low, only less than 10% of their untreated control.

Figure 13B:
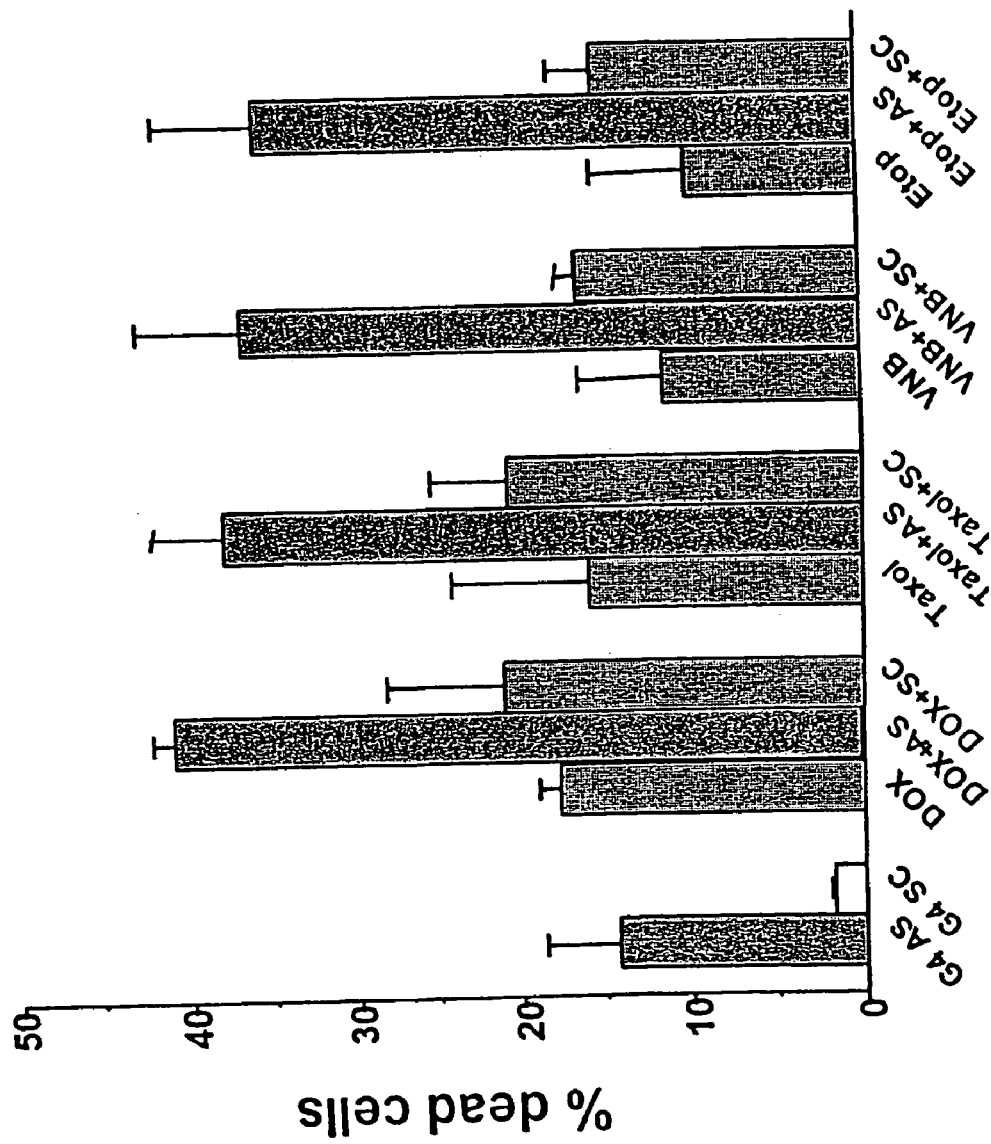
FIG. 13B is a graph showing the percentage of dead H460 cells after treatment with LFA and complexes with G4 AS oligonucleotides or G4 SC oligonucleotides at 0.4 µM dose in the presence or absence of doxorubicin (DOX), taxol, vinorelbine (VNB) or etoposide (Etop), as determined by MTT assay. The data represent the mean±SD of three independent experiments.

To investigate whether down-regulation of XIAP expression has the potential to sensitize H460 cells to chemotherapy, combination treatments using G4 AS oligonucleotides and one of the following anticancer drugs: doxorubicin (DOX), taxol, vinorelbine (VNB) and etoposide (Etop) were performed. FIG. 13B demonstrates that each of the combinations resulted in at least an additive cytotoxic effect on the cell death, compared to treatment with either G4 AS oligonucleotides or the anticancer drugs alone.

EXAMPLE 10

Antitumor Efficacy of G4 AS Oligonucleotides on H460 and LCC6 Tumor Xenografts

Figure 14:
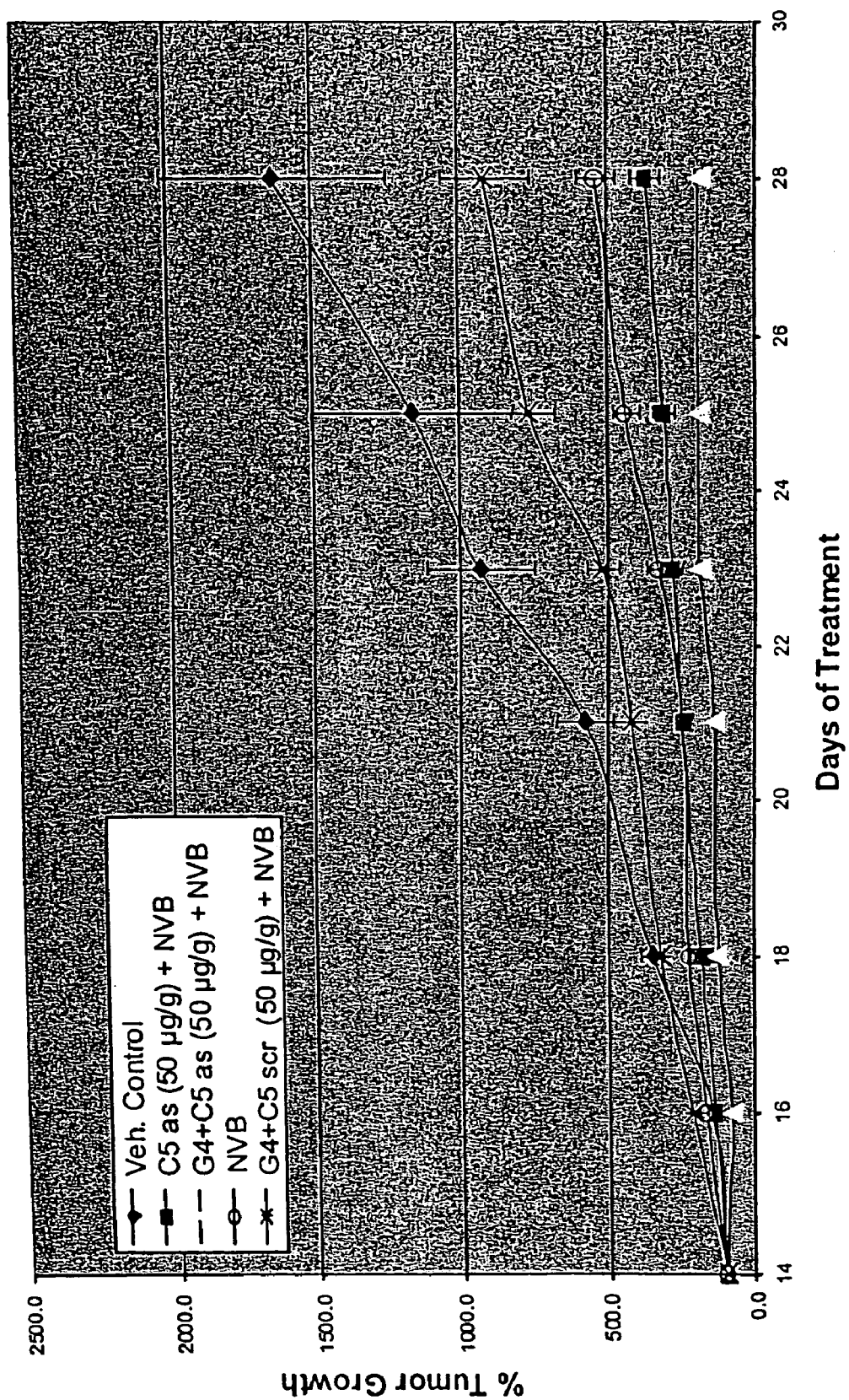
FIG. 14 is a graph showing relative H460 tumor growth in mice treated with XIAP AS 2×2 MBOs and vinorelbine. Intratumoral injection of oligonucleotides at 50 µg/g tumor mass was performed in SCID-RAG2 mice carrying subcutaneous H460 cell xenografts. This treatment was combined with administration of vinorelbine.

We first determined whether intra-tumoral injection of XIAP antisense 2×2-MBOs into SCID-RAG2 mice carrying sub-cutaneous H460 human lung carcinoma xenografts reduced the amount of tumor growth. Treatment started 14 days after tumor cell inoculation (s.c. shoulder injection of $10^6$ cells) by injecting MBOs (50 µg 2'-O-methyl RNA oligonucleotides per g tumor) into the palpable tumor mass three times per week for two weeks. Vinorelbine (VNB; also referred to as navelbine) (NVB) (15 mg/kg i.p.) was injected on days 17 and 24. Tumor size was measured with calipers three times per week. At the end of the treatment period (day 24), the mean relative tumor growth of mice treated with a combination of C5+G4 AS MBOs and VNB was ~70% reduced compared to those treated with scrambled control MBOs and VNB. Treatments with C5 AS MBO and VNB resulted in a ~60% reduction of tumor size, compared to scrambled control (FIG. 14).

Figure 15:
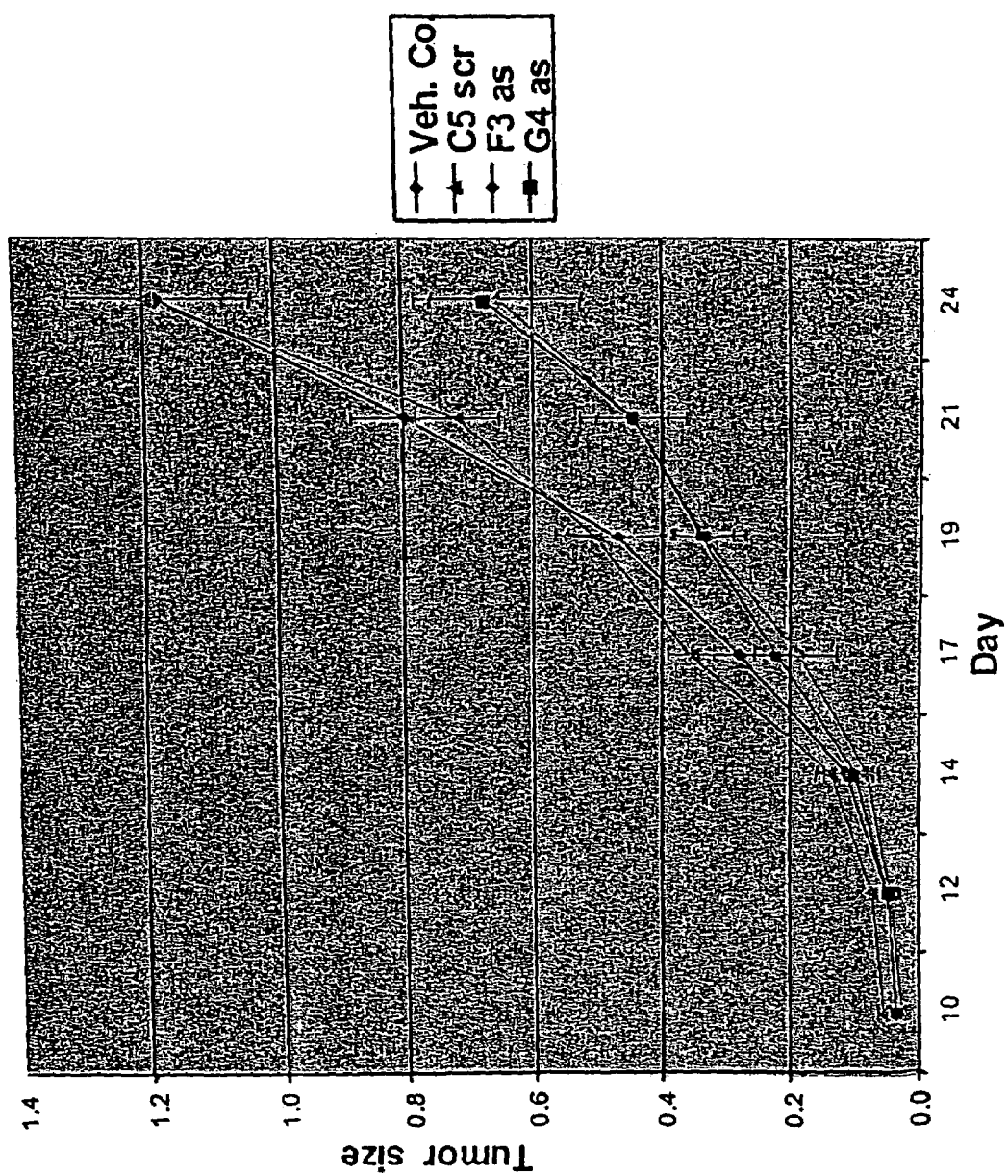
FIG. 15 is a graph showing mean H460 cell tumor size in mice treated systemically with XIAP AS PS-oligonucleotides. Systemic delivery (i.p.) of XIAP AS PS-oligonucleotides into SCID-RAG2 mice implanted with subcutaneous H460 cell xenografts reduced the size of the tumors, relative to control.
Figure 16:
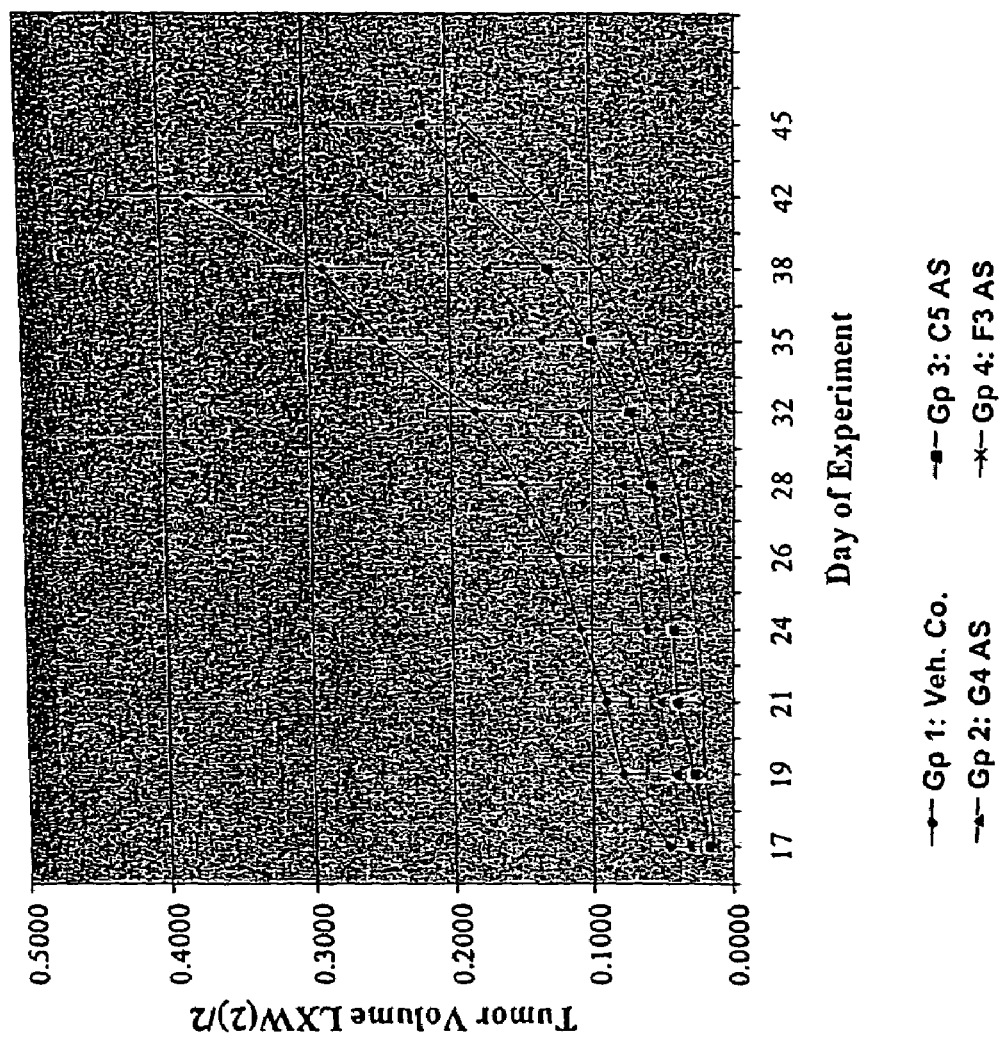
FIG. 16 is a graph showing MDA-MB-435/LCC6 human breast carcinoma cell (LCC cell) tumor size in mice treated systemically with XIAP AS PS-oligonucleotides. Systemic delivery (i.p.) of XIAP AS PS-oligonucleotides into female SCID-RAG2 mice implanted with LCC6 cell xenografts in mammary fat pads reduced the size of the tumors, relative to control.

Initial systemic PS-oligonucleotide studies were designed without any chemotherapeutic agents. SCID-RAG2 mice were inoculated with H460 human lung carcinoma cells (s.c. shoulder injection of $10^6$ cells) and treatments with G4 and F3 AS PS-oligonucleotides, as well as a scrambled control, were initiated three days after tumor inoculation. Nucleobase oligomer injections were administered i.p. at 12.5 mg/kg three times a week for three weeks. At the end of the treatment period, mean tumor sizes in the groups treated with either G4 or F3 AS oligonucleotides were ~50% smaller than in the group treated with a scrambled control oligonucleotides (FIG. 15). The same treatment protocol was tested on female SCID-RAG2 mice inoculated orthotopically with MDA-MB-435/LCC6 human breast carcinoma cells. Two weeks after the last treatment (day 35) tumor volumes of mice treated with F3, C5 or G4 AS oligonucleotides were 70%, 60%, and 45%, respectively, smaller than vehicle controls (FIG. 16).

Figure 17:
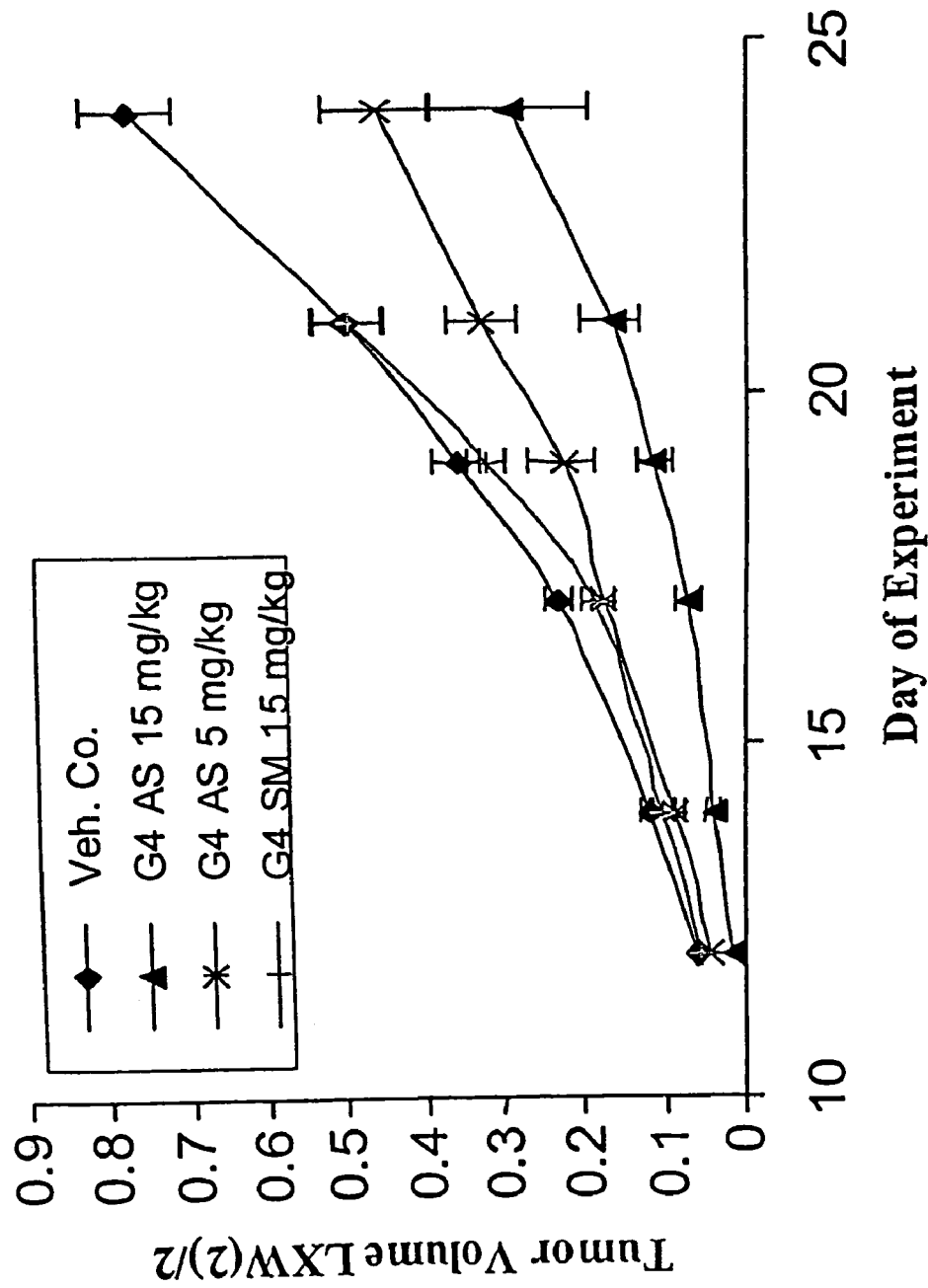
FIG. 17 is a schematic illustration showing in vivo effects of G4 oligonucleotides on tumor growth and tumor XIAP protein levels. Antitumor efficacy of systemically delivered, naked XIAP G4 AS oligonucleotides or G4 SC oligonucleotides on the growth of subcutaneous H460 cell xenografts in male SCID-RAG2 mice. All data are expressed as mean±SEM (n=6 mice/group).
Figure 18A:
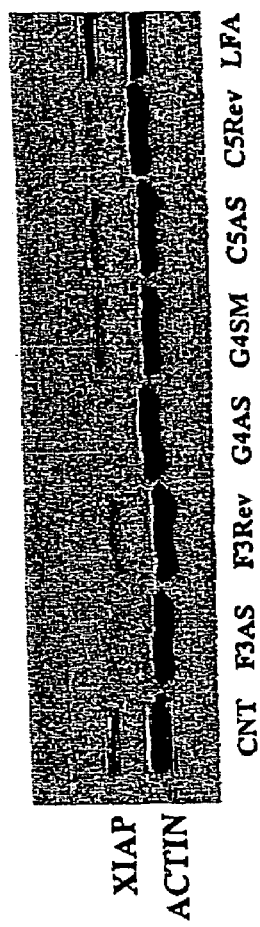
FIGS. 18A and 18B are schematic illustrations depicting XIAP protein expression levels in H460 tumor xenografts implanted in SCID-RAG2 mice after 21 days treatment with G4 AS oligonucleotides, G4 SC oligonucleotides, or vehicle alone (control), analyzed by western blotting and quantified by densitometry. XIAP levels were normalized to cellular actin levels. All data are expressed as mean±SD (n=3).

We conducted additional examination of the antitumor effects of G4 AS oligonucleotides in SCID-RAG2 mice bearing xenografts of H460 human non-small-cell lung tumors implanted subcutaneously. Saline-treated control tumors grew reproducibly to a size of 0.75 cm$^3$ within approximately 24 days (FIG. 17). Oligonucleotide treatments were initiated three days after tumor cell inoculation. G4 AS oligonucleotides (5 to 15 mg/kg) were administered using a treatment schedule of i.p. injections given once a day on days 3-7, 10-14, and 17-21. The treatment with 5 or 15 mg/kg G4 AS oligonucleotides greatly delayed tumor growth: on day 24 mean tumor sizes were 0.75, 0.45 and 0.29 cm$^3$ in control, 5 and 15 mg/kg treated groups, respectively (FIG. 18A). There was a dose-dependent inhibition of tumor growth. Tumor size in mice treated with 15 mg/kg G4 AS oligonucleotides was significantly smaller than in control groups, and represented 39% of control mean tumor size. In contrast, administration of G4 SC oligonucleotides at 15 mg/kg provided no therapeutic activity (FIG. 17). None of the mice treated with oligonucleotides displayed any signs of toxicities, and both doses of oligonucleotides were well tolerated. A dose of 15 mg/kg was selected for the future combination treatment regimens with anticancer drugs.

EXAMPLE 11

XIAP Expression is Reduced in H460 Tumors Treated with G4 as Oligonucleotides

Figure 18B:
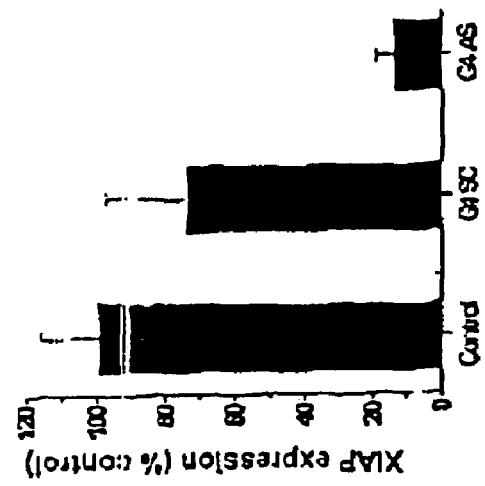

To correlate the tumor growth inhibitory effects of G4 AS oligonucleotides with XIAP protein expression, we examined the changes in XIAP expression at the end of the in vivo treatment with 15 mg/kg of G4 AS and SC oligonucleotides. At day 21 or 24 post-tumor inoculation when tumors reached 1 cm$^3$ in size (FIG. 17), tumors were harvested and lysates from tumor homogenates were used for western blot analysis. XIAP and β-actin antibodies against the human protein were used, allowing for determination of human XIAP levels obtained from tumor cells specimens without contamination from XIAP derived from mouse cells. XIAP protein levels in tumors treated with G4 AS oligonucleotides were significantly reduced to approximately 85% of control tumors (P<0.005) (FIGS. 18A and 18B). Tumors treated with G4 SC oligonucleotides were reduced in size by 24% of control tumors. These results indicated that inhibition of H460 tumor growth by G4 AS oligonucleotides correlated with the down-regulation of XIAP protein expression.

EXAMPLE 12

Histopathology of Tumor Specimens

Figure 19A:
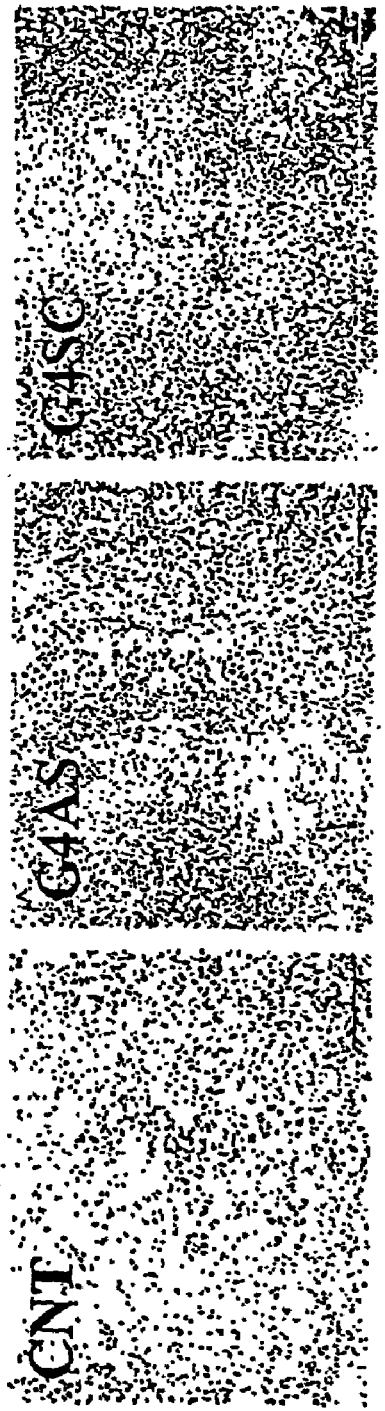
FIGS. 19A and 19B are photomicrographs showing in vivo effects of G4 oligonucleotides on histopathology of H460 tumors implanted in SCID-RAG2 mice after 15 mg/kg systemic dosing of XIAP G4 AS oligonucleotides or G4 SC oligonucleotides over 21 days.
Figure 19B:
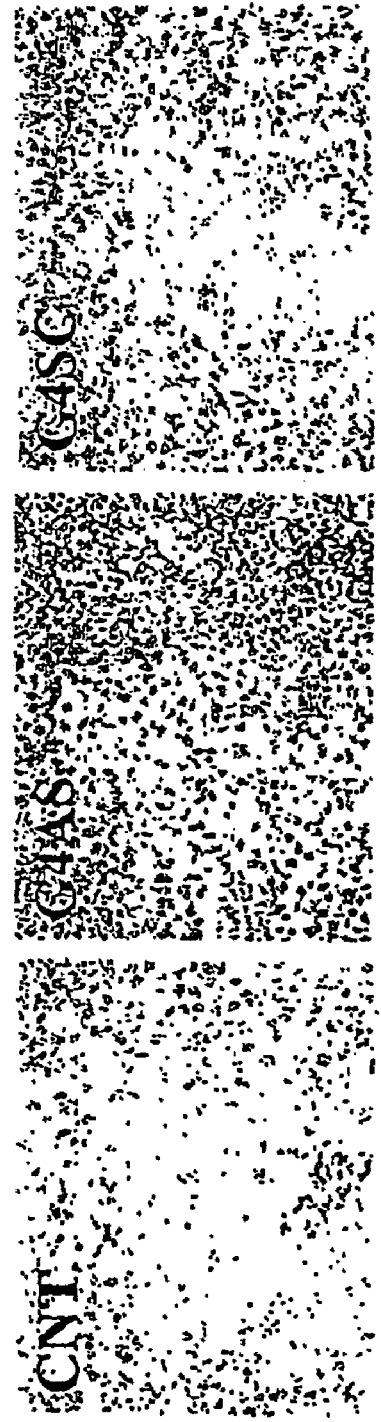

To evaluate whether XIAP AS oligonucleotide administration results in direct tumor cell kill, we examined the histology of tumors after treatment both for morphology and ubiquitin immunostaining (FIGS. 19A and 19B). At day 21 or 24 post-tumor inoculation, tumors treated with 15 mg/kg of G4 AS oligonucleotides, SC oligonucleotides, or saline control were excised, sectioned, and stained with hematoxylin and eosin. The results demonstrate that tumors in animals administered given XIAP AS oligonucleotides treatment contained an increased number of dead cells, identified morphologically by their amorphous shape and condensed nuclear material (FIG. 19A).

The degradation of proteins is largely ubiquitin-proteasome-dependent; increased ubiquitin expression has been observed during apoptosis. Thus, we examined the ubiquitin expression in the tumors sections used for hematoxylin and eosin staining. As shown in FIG. 19B, tumors in mice administered XIAP AS oligonucleotides displayed more intense immunohistochemical staining, relative to tumors in control or SC ODN-treated mice. These data indicate that there is more free ubiquitin and/or ubiquitinated-protein in XIAP AS nucleobase oligonucleotide-treated tumor cells than in control tumors.

EXAMPLE 13

Combined Treatment of G4 as Oligonucleotides with Vinorelbine

Figure 20:
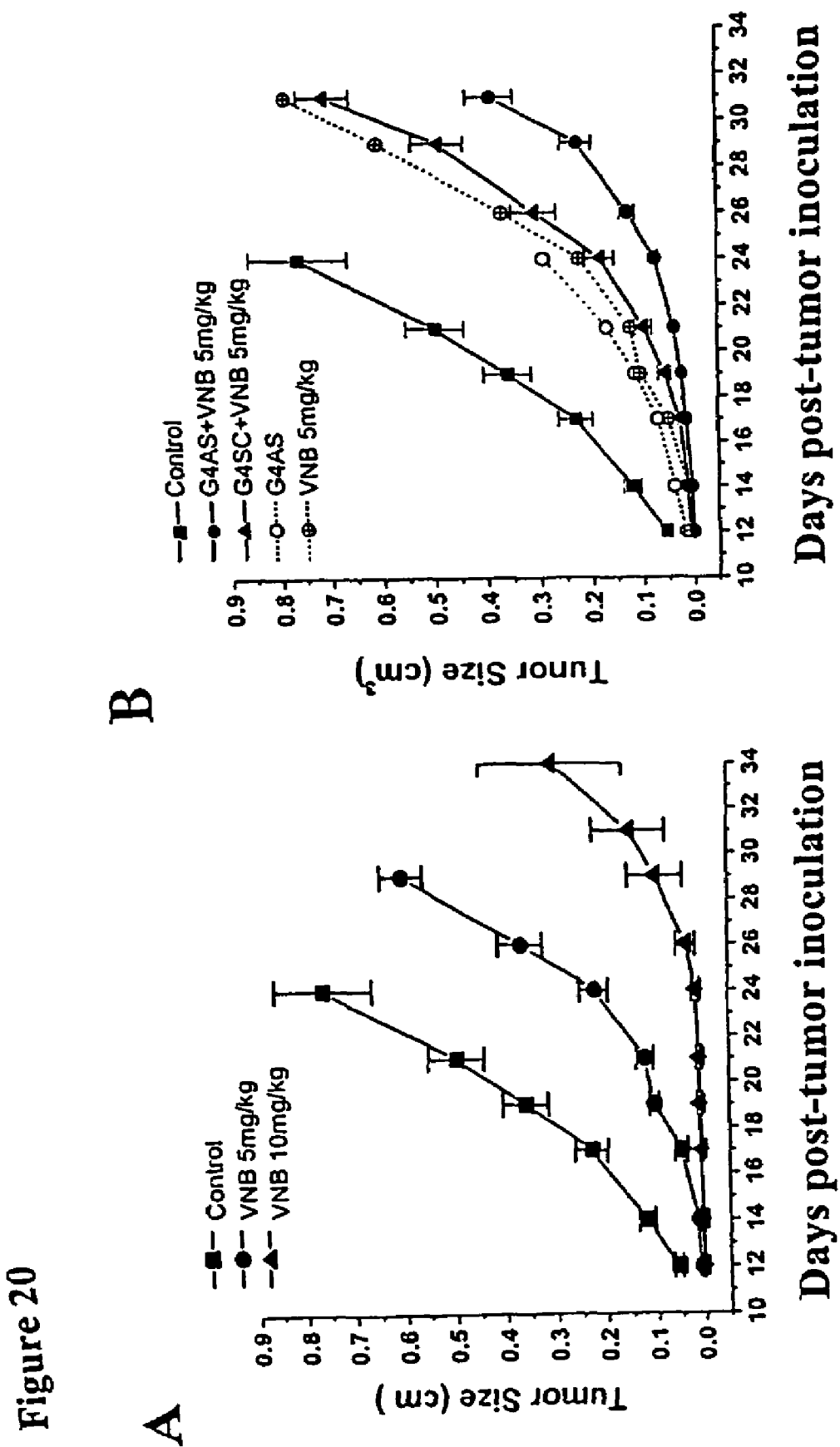
FIGS. 20A and 20B are graphs showing increased in vivo efficacy of vinorelbine (VNB) in combination with XIAP oligonucleotides. Antitumor efficacy of VNB with or without XIAP G4 AS oligonucleotides or G4 SC oligonucleotides against H460 tumors xenografts was determined in SCID-RAG2 mice.

To evaluate whether combined treatments of G4 AS nucleobase oligomers and vinorelbine (VNB), a chemotherapeutic agent used for lung cancer treatment, may result in any cooperative effects, we compared the therapeutic efficacy of VNB in the presence and absence of G4 AS oligonucleotides or G4 SC oligonucleotides. Treatment regimens were initiated on day 3 after tumor inoculation. FIG. 20A shows the in vivo efficacy results for 5 mg/kg and 10 mg/kg doses of VNB given to H460 tumor-bearing mice and compared with saline controls. Each of the two regimens induced significant tumor growth suppression in a dose-dependent manner without showing significant signs of undesirable toxicity (i.e., body weight loss). When administration of G4 AS oligonucleotides (15 mg/kg) was combined with VNB (5 mg/kg) for the treatment of H460 tumors, even more pronounced delay of H460 tumor growth was observed compared to either treatment administrated alone (FIG. 20B). Again, the mice did not show any significant signs of toxicity (i.e., body weight loss). The mean tumor sizes in mice treated with 5 mg/kg VNB in the presence or absence of G4 AS or SC oligonucleotides were compared on day 29 (FIGS. 20A and 20B). The average tumor size in the group of VNB and G4 AS oligonucleotides was 0.22±0.03 cm$^3$, which was significantly smaller than the average tumor size in animals treated with 5 mg/kg VNB alone or with a combination of VNB G4 SC oligonucleotides (0.59±0.04 and 0.48±0.05 cm$^3$, respectively).

Methods

The results obtained in Examples 5-13 were obtained using the following methods.

Oligonucleotide Synthesis

A library of over 96 non-overlapping chimeric, or mixed-backbone (MBO), 19-mer antisense oligonucleotides was synthesized as 2×2 MBO oligonucleotides, composed of two flanking 2'-O-methyl RNA residues at either end with phosphorothioate linkages, and a central core of 15 phosphodiester DNA residues. Each final product was desalted by Sephadex G-25 chromatography (IDT Inc., Coralville, Iowa). This chimeric wingmer configuration, and mix of phosphorothioate and phosphodiester linkages (referred to as 2×2 PS/PO), provided adequate stability while also reducing non-specific toxicity associated with phosphorothioate residues. Fully phosphorothioated non-chimeric (DNA) antisense oligonucleotides for in vivo and in vitro studies were synthesized by Trilink Biotech and purified by RP-HPLC.

Antisense Oligonucleotide Screening

T24 bladder carcinoma cells, transfected with 1-1.2 µM oligonucleotide-lipofectin complexes for 24-48 hours, were assessed to determine the ability of each oligonucleotide to knock-down XIAP protein. Positive hits were reconfirmed for their ability to knock-down (i) XIAP protein levels at 12-18 hours of transfection by western analysis, and (ii) XIAP mRNA levels at 6-9 hours of transfection by quantitative RT-PCR (see below) in T24 bladder carcinoma cells and H460 lung carcinoma cells. Candidate oligonucleotides were identified and tested further. Identified 2×2 PS/PO chimeric oligonucleotides showed a dose-dependent ability to decrease XIAP mRNA levels at 6-9 hours in the range of 400-1200 nM concentrations. Exemplary oligonucleotides are shown in Table 5.

TABLE 5

| Oligonucleotide | Sequence* | | SEQ ID NO: |
|---|---|---|---|
| F3 AS | ATCTTCTCTTGAAAATAGG | (PS) | 278 |
| F3 AS | AUCTTCTCTTGAAAATAGG | (2 × 2 PS/PO) | 279 |
| F3 RP | GGATAAAAGTTCTCTTCTA | (PS) | 280 |
| G4 AS | GCTGAGTCTCCATATTGCC | (PS) | 281 |
| G4 AS | GCTGAGTCTCCATATTGCC | (2 × 2 PS/PO) | 282 |
| G4 SC | GGCTCTTTGCCCACTGAAT | (PS) | 283 |
| C5 AS | ACCATTCTGGATACCAGAA | (PS) | 284 |
| C5 AS | ACCATTCTGGATACCAGAA | (2 × 2 PS/PO) | 285 |
| C5 RP | AAGACCATAGGTCTTACCA | (PS) | 286 |
| AB6 AS | GGGTTCCTCGGGTATATGG | (PS) | 287 |
| AB6 RP | GGTATATGGCGTCCTTGGG | (PS) | 288 |
| DE4 AS | GGTATCTCCTTCACCAGTA | (PS) | 289 |
| DE4 RP | ATGACCACTTCCTCTATGG | (PS) | 290 |
| D7 AS | GATTCACTTCGAATATTAA | (PS) | 291 |
| D7 RP | AATTATAACGTTCACTTAG | (PS) | 292 |

*Bold residues = DNA residues with phosphorothioate linkages, underlined residues = 2'-O-methyl RNA bases, plain type = phosphodiester DNA residues.

Tumor Cell Line and Animal Xenografts Model

The human non-small cell lung cancer cell line (large cell type) NCI-H460 (H460) was obtained from ATCC and maintained in RPMI 1640 supplemented with 10% FCS at 37° C.

in a humidified atmosphere containing 5% $CO_2$. Cells were used in exponential growth phase, up to a maximum of 25 in vitro passages. Male SCID-RAG2 mice (7-9 weeks old, 23-26 g) were obtained from British Columbia Cancer Agency Joint Animal Facility breeding colony and kept in aseptic environments. A tumor model of NCI-H460 cells in SCID-RAG2 mice was established by subcutaneous implantation of $1 \times 10^6$ NCI-H460 cells on the back of mice.

Treatment of Cells with Antisense and Anticancer Drugs

One day prior to transfection, H460 cells were plated in 6- or 96-well tissue culture plates. Phosphorothioate antisense oligonucleotides were delivered into cells with Lipofectamine 2000 (Life Technologies) in the form of liposome-oligonucleotide complexes. Following a 4.5 or 6 h transfection, the transfection medium was replaced with RPMI medium containing 10% FBS, and the cells incubated for another 24 or 48 h.

Real-Time Quantitative RT-PCR

Total RNA from H460 cells treated with liposome-oligonucleotide complexes for 6 hours was immediately isolated using RNeasy mini spin columns and DNase treatment (QIAGEN, Valencia, Calif.). Specific XIAP mRNA was measured using a real-time quantitative RT-PCR method. XIAP forward and reverse primers (600 nM) and probe (200 nM) (5'-GGTGATAAAGTAAAGTGCTTTCACTGT-3' (SEQ ID NO 293), 6FAM-CAACATGCTAAATGGTTCCAGGGTG-CAAATATC-TAMRA (SEQ ID NO: 294), and 5'-TCAG-TAGTTCTTACCAGACACTCCTCAA-3' (SEQ ID NO: 295) were designed to span exon 3-4 and 4-5 junctions. One of the primers, as well as the probe, was designed to overlap an intron-exon boundary to block detection of any possible genomic DNA contamination. The RNA was reverse-transcribed and PCR amplified using the TaqMan EZ RT-PCR kit (PE/ABI, Foster City, Calif.) in the ABI prism 7700 Sequence Detection System (PE/ABI). The thermal cycling condition for the RT step were 50° C. for 2 min, 60° C. for 30 min, and 95° C. for 5 min, followed by 45 cycles of PCR (at 94° C. for 20 s and 60° C. for 1 min per cycle). The XIAP mRNA level of each sample was calculated relative to untreated control cells. XIAP mRNA levels were determined by the cycle threshold method (Ct) using a threshold of 30× the baseline SD, and XIAP levels were normalized for GAPDH content, using PE/ABI supplied primers and probe.

Western Blot Analysis

The cells or tumor tissue samples were lysed with ice-cold lysis buffer (50 mM Tris, 150 mM NaCl, 2.5 mM EDTA, 0.1% SDS, 0.5% sodium deoxycholate, 1% NP-40, 0.02% sodium azide) containing protease inhibitors (Complete-Mini protease inhibitor tablets; Boehringer Mannheim GmBH, Mannheim, Germany). After incubation for 30 min on ice, samples were centrifuged at 10,000 rpm for 15 min, and stored at −20° C. Protein content in the lysed extracts was determined using a detergent-compatible Bio-Rad assay (Bio-Rad Labs, Hercules, Calif.). Equal amounts of protein (40 μg/lane) were separated on 12% SDS-polyacrylamide gels or 4-15% gradient SDS-polyacrylamide pre-made gels (Bio-Rad) and transferred to nitrocellulose membranes. Primary antibodies against XIAP, Bcl-2 (DAKO, Glostrup, Denmark), Bax (Sigma, St. Louis, Mo.), β-actin (Sigma), caspase-3 (BD PharMingen, San Diego, Calif.), and PARP (BD PharMingen) were used. The secondary antibody was the appropriate horseradish-conjugated anti-mouse or anti-rabbit IgG (Promega, Madison, Wis.). Proteins were detected by enhanced chemiluminescence (ECL; Amersham Pharmacia Biotech, Buckinghamshire, England) and visualized after exposure to Kodak autoradiography film. Scanning densitometry (Molecular Dynamics, Sunnyvale, Calif.) was performed to quantify band intensities by volume/area integration. The amount of XIAP, caspase-3, Bcl-2 and Bax in cells was normalized to their respective lane β-actin levels, upon stripping and reprobing.

Measurement of Cell Growth and Viability or Death

Growth inhibition of H640 cells was determined by the colorimetric MTT cell viability/proliferation assay. In brief, cells were treated with liposome-oligonucleotide complexes for 4.5 h, then incubated for another 48 h at 37° C. in medium without transfection reagent or oligonucleotides in the presence or absence of anticancer drugs. MTT (25 μg/well) was added to each well, and the plates incubated for 3 h at 37° C. Following the incubation step, the colored formazan product was dissolved by the addition of 200 μl DMSO. Plates were read using the microtiter plate reader (Dynex Technologies Inc., Chantilly, Va.) at a wavelength of 570 nm. The percentage of surviving cells in wells treated with oligonucleotides was normalized to untreated controls. All assays were performed in triplicate.

Apoptotic Flow Cytometric Assays

Cells were treated with liposome-oligonucleotide complexes for 4.5 h, and incubated for another 48 h in the medium without transfection reagent at 37° C. Following incubation, cells were harvested, washed twice with sample buffer (0.5% glucose in PBS without $Ca^{++}$ and $Mg^{++}$), and fixed in cold 70% ethanol at 4° C. for at least 18 hrs. Samples were centrifuged at 3000 rpm for 10 min, then resuspended in sample buffer containing 50 μg/ml propidium iodide (PI) and 400 U/ml RNase A. Samples were incubated for 30 min at room temperature and 30 min on ice, followed by flow cytometry analysis. EXPO Software (Applied Cytometry Systems, Sacramento, Calif.) was used to generate histograms, which were used to determine the cell cycle phase distribution after debris exclusion. The Sub G1/G0 cell fraction was considered as representative for apoptotic cells.

Nuclear Morphology

Cells were treated with liposome-oligonucleotide complexes for 4.5 h, and incubated for another 48 h at 37° C. in the medium without transfection reagent or oligonucleotides. Cells were harvested and stained with 0.10 μg/ml DAPI (4', 6-diamidino-2-2-phenylindole) for 30 min at room temperature. Cells were placed on a glass slide, cytospun, and viewed with a Leica microscope and 40× objective lens under UV fluorescent illumination. Digital images were captured using Imagedatabase V. 4.01 Software (Leica, Germany).

In Vivo Antitumor Activity

Efficacy experiments were conducted in male RAG2 immunodeficient mice bearing NCI-H460 tumours or female RAG2 mice bearing LCC6 tumors. Treatments were commenced on day 3 after tumor inoculation. Saline (controls), G4 AS oligonucleotides (5 or 15 mg/kg), or G4 SC oligonucleotides (5 or 15 mg/kg) were administered i.p. daily for five doses a week over a three week regimen. Vinorelbine (VNB, 5 or 10 mg/kg) was administered i.v. via the tail vein, either alone or in combination with oligonucleotides, at day 3, 7, 11 and 17 after tumor inoculation. When oligonucleotides were administered in combination with VNB, the drug treatment was performed four hours after ODN treatment.

Mice were observed daily. Body weight measurements and signs of stress (e.g., lethargy, ruffled coat, ataxia) were used to detect possible toxicities. Animals with ulcerated tumor, or tumor volumes of 1 $cm^3$ or greater were killed. Digital caliper measurements of tumors were converted into mean tumor size (cm³) using the formula: ½[length (cm)]×[width (cm)]². An average tumor size per mouse was used to calculate the group mean tumor size±SE (n=6 mice) from at least two independent experiments per group.

Tumor and Tissue Processing

Mouse tumors were collected on day 21 or 24 post-tumor inoculation and treatment. One portion of the tumor tissue was fixed in formalin. Paraffin-embedded tissues were sectioned and subjected to gross histopathology using hematoxylin and eosin staining and immunohistochemistry for ubiquitin expression. The other portion of the tumor was homogenized in lysis buffer for western blot analysis (see above).

Statistical Analyses

Student's t test was used to measure statistical significance between two treatment groups. Multiple comparisons were done using one-way ANOVA and a post-hoc test that compared different treatment groups by the Shellé test criteria (Statistica release 4.5, StatSoft Inc., Tulsa, Okla.). Data were considered significant for a P-value of <0.05.

EXAMPLE 14

Antisense HIAP1 Oligonucleotides Decrease HIAP1 RNA and Polypeptide Expression

A library of 15 HIAP1 antisense nucleobase oligomers as oligonucleotides was screened for protein knock-down by western blot analysis and for RNA knock-down by TaqMan, using the primers and probes described in Example 3, above, under two different conditions. HIAP1 RNA levels may be detected using standard Northern blot analyses or RT-PCR techniques. The antisense oligonucleotides were administered to cells under basal conditions or under cycloheximide-induction conditions (24 hour treatment with sub-toxic doses). Cycloheximide (CHX) can lead to a 10- to 200-fold induction of HIAP1 mRNA depending on the cell line treated. This in turn leads to an increase in HIAP1 protein, as seen on a Western blot (70 kDa band). This effect of CHX is via two distinct mechanisms of action. First, CHX activates NFkB, a known transcriptional inducer of HIAP1, by blocking the de novo synthesis of a labile protein, IkB, which is an inhibitor of NFkB. This effect is mimicked by puromycin, another protein synthesis inhibitor, and by TNF-alpha, which induces a signaling cascade leading to the phosphorylation, ubiquination, and degradation of IkB. Only CHX leads to a further stabilization of the HIAP1 mRNA, as seen by the decreased rate of disappearance of HIAP1 message in the presence of actinomycin D, to block de novo transcription, and CHX, as opposed to actinomycin D and puromycin or TNF-alpha combined.

Figure 21:
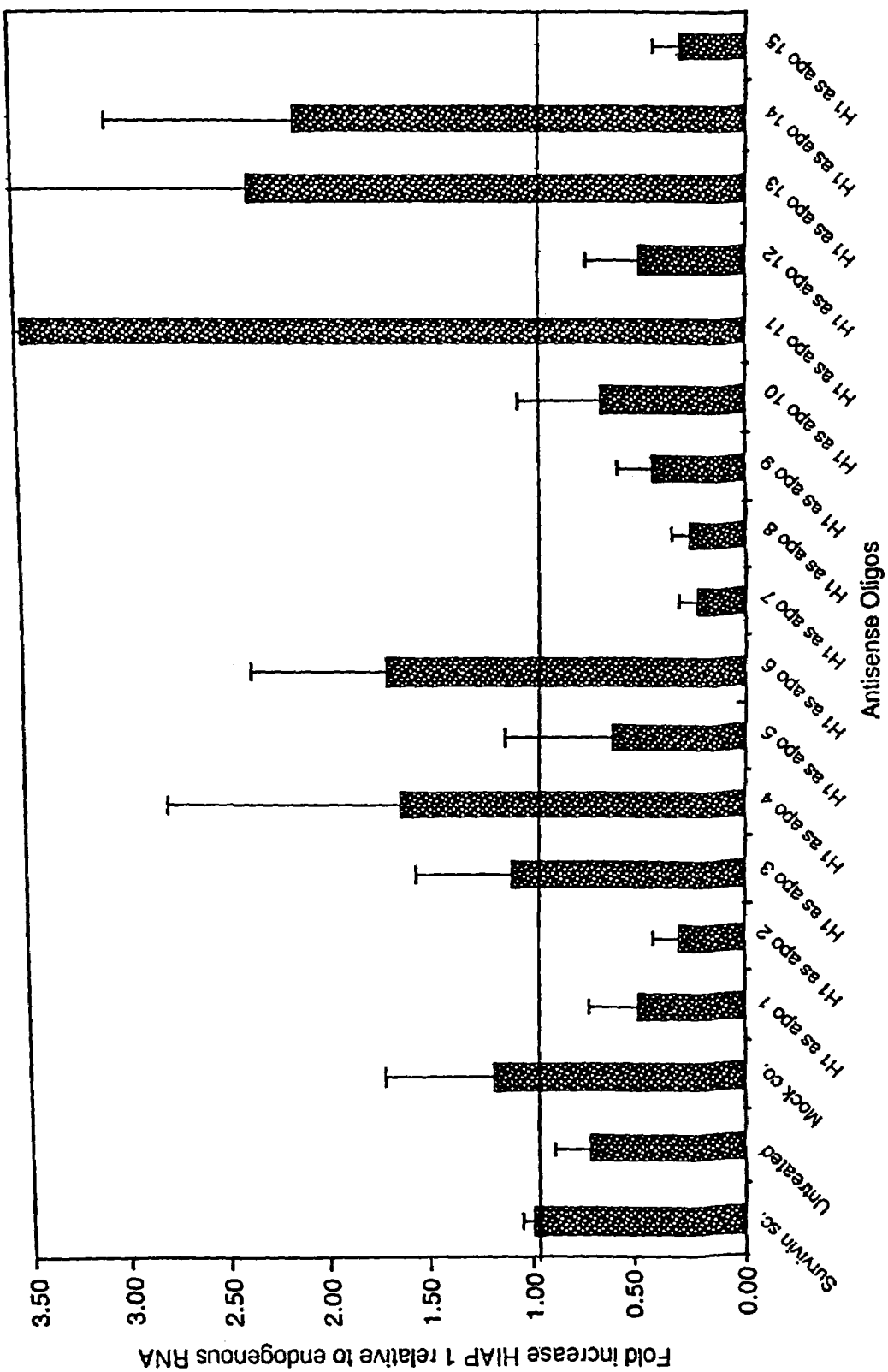
FIG. 21 is a graph showing the effects of HIAP1 oligonucleotides on HIAP1 RNA levels.

SF295 glioblastoma cells were transfected with lipofectin and oligonucleotide (scrambled survivin, no oligonucleotide, antisense APO 1 to APO 15) or left untreated. RNA was isolated from the cells six hours after transfection and the level of HIAP1 mRNA was measured by quantitative PCR (TaqMan analysis), normalized for GAPDH mRNA, with the value for the scrambled survivin oligonucleotide transfection set as 1.0. The results of this experiment, a compilation of three separate experiments, are shown in FIG. 21. The scrambled survivin oligonucleotide, the mock transfection, and untreated (non-transfected) cells, all showed similar HIAP1 mRNA levels. Of the 15 antisense oligonucleotides, seven (APO 1, 2, 7, 8, 9, 12, 15) showed an almost 50% decrease when compared to mock transfection or survivin scrambled control oligonucleotide transfection (5'-mU-mAmAGCTGTTCTATGTGmUmUmC-3'; SEQ ID NO: 296) (FIG. 21). Some of the oligonucleotides led to an induction in HIAP1 mRNA, which may be a stress response to a non-specific toxic oligonucleotide. An antisense oligonucleotide may still be effective at knocking down HIAP1 protein levels even if the message is increased if the oligonucleotide is able to interfere with the translation process.

Figure 22A:
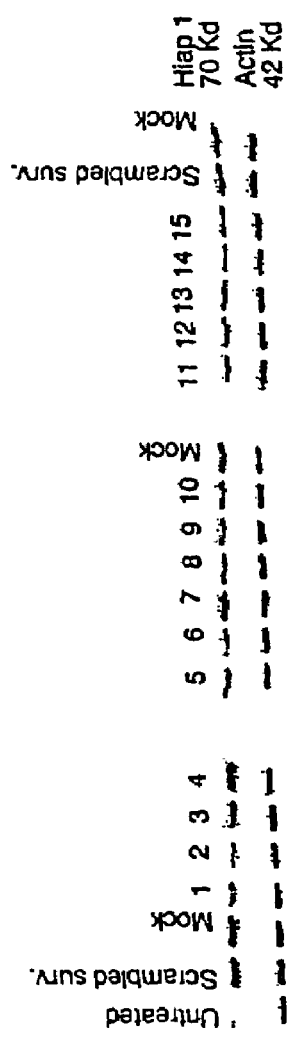
FIGS. 22A and 22B are schematic illustrations showing densitometric scans of western blots showing the effects of HIAP1 oligonucleotides on a cell's ability to block cycloheximide-induced upregulation of HIAP1 protein.
Figure 22B:
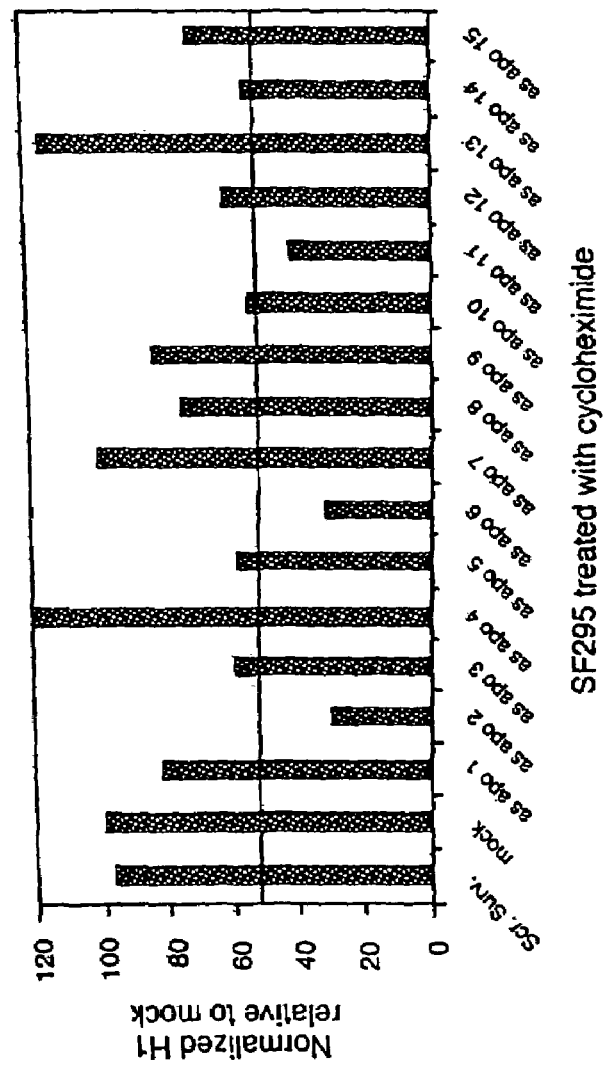

The effect of HIAP1 antisense nucleobase oligomers on HIAP1 protein and mRNA expression was also examined in cells induced to express HIAP1. SF295 cells were transfected with oligonucleotides, or were mock transfected. The transfected cells were then treated with 10 µg/ml cycloheximide for 24 hours to induce 70 kDa HIAP1 mRNA and protein. Protein levels were measured by western blot analysis with an anti-HIAP1 polyclonal antibody, and normalized against actin protein in a re-probing of the same blots. Scans of the western blot results are shown in FIG. 22A. The densitometric scan results were plotted against the mock results (set at 100%) in FIG. 22B. A line is drawn at 50% to easily identify the most effective antisense oligonucleotides. The transfection process itself (e.g., mock or scrambled survivin) induces HIAP1 protein compared to the untreated sample as shown on the western immunoblot.

Figure 23:
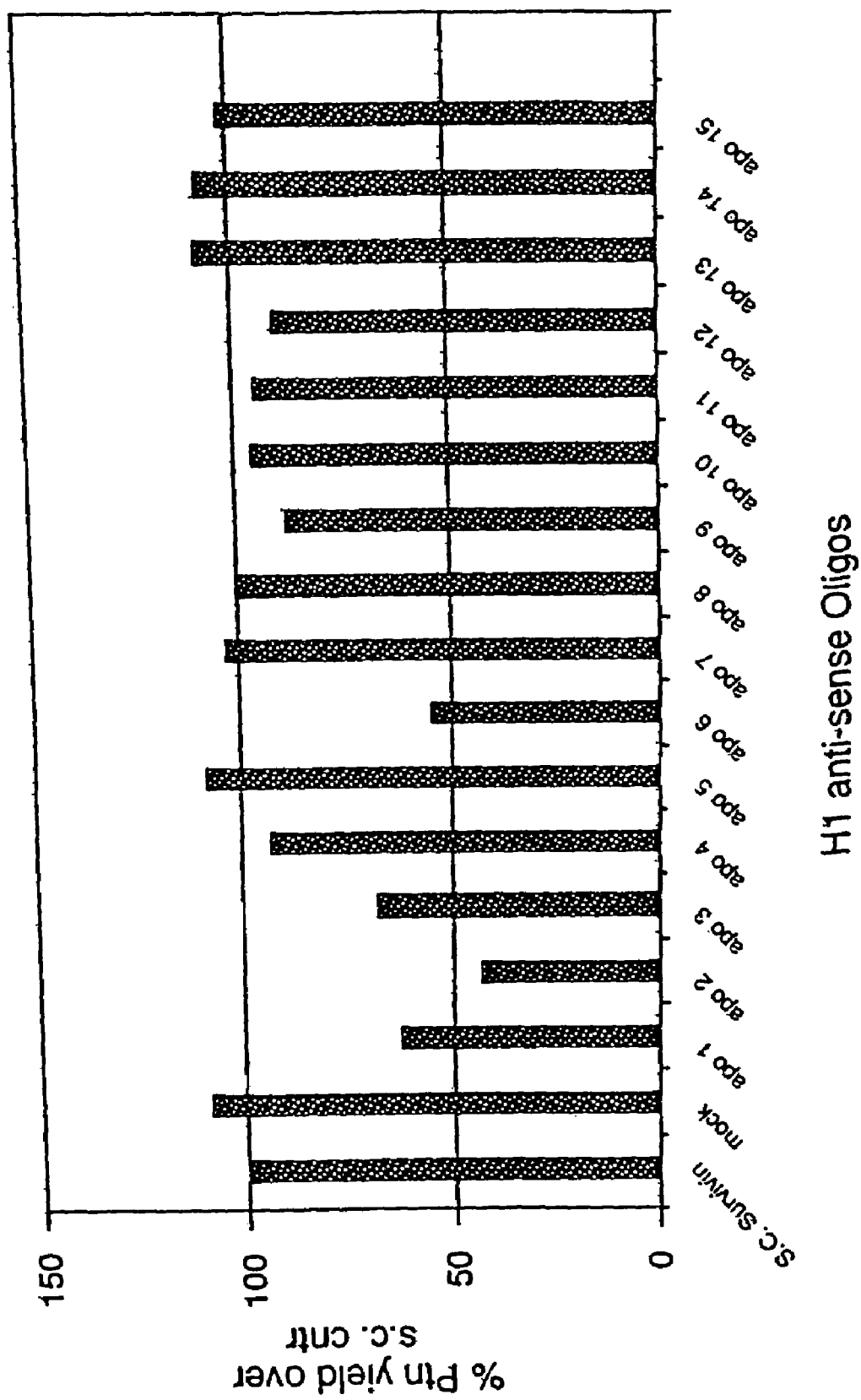
FIG. 23 is a graph showing the effects of HIAP1 oligonucleotides on cytotoxicity, as measured by total protein.
Figure 24:
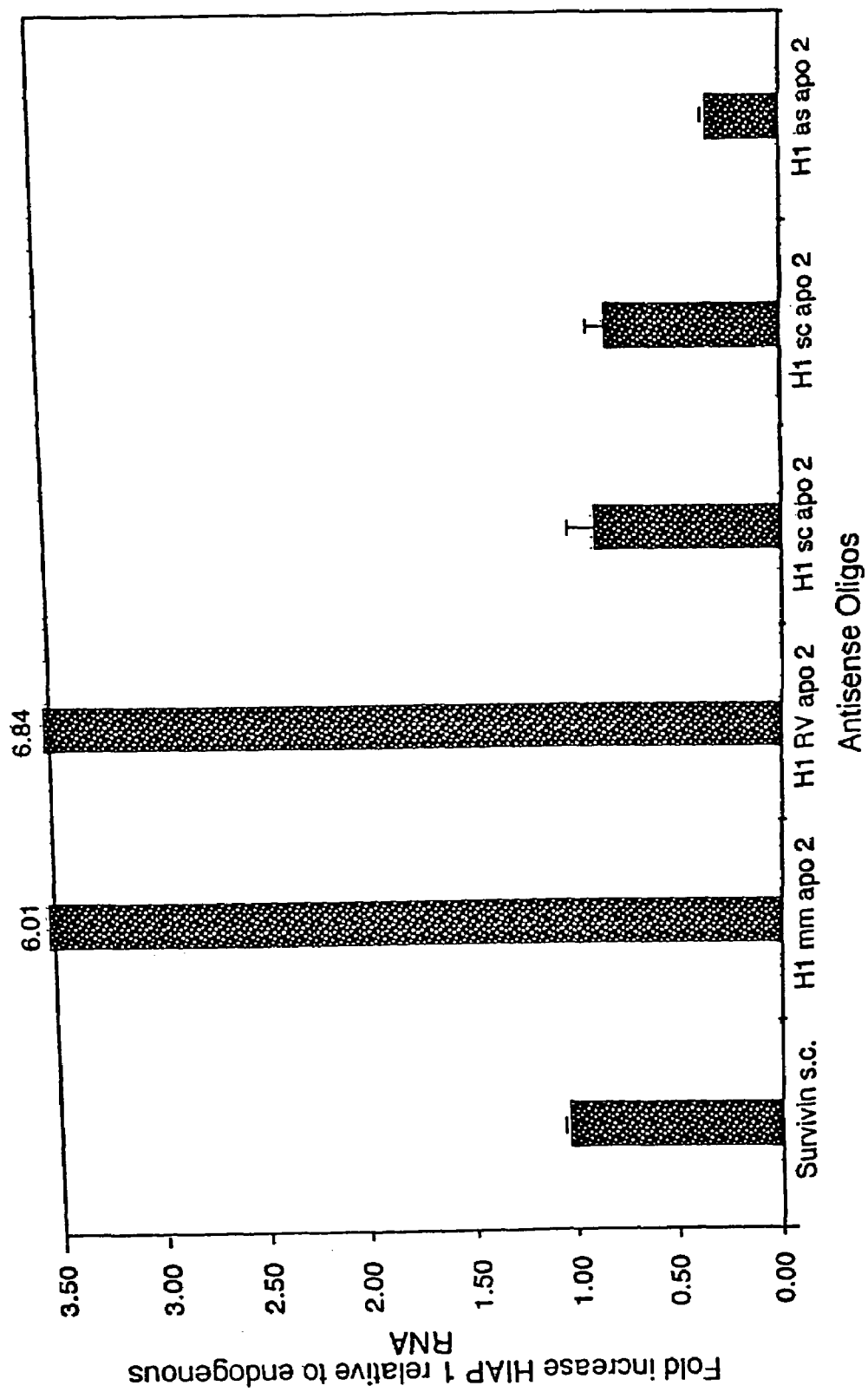
FIG. 24 is a graph showing the validation of the sequence specificity for HIAP1 oligonucleotide APO 2.

Of the 15 tested nucleobase oligomers, six of them (APO 1, 2, 7, 8, 12, and 15) showed high activity, or had significant activity in both the protein and mRNA assays, and did not cause a stress-induced increase in HIAP1 mRNA, such as that seen with APO 4, 6, 11, 13, 14 (FIG. 21), and by control oligonucleotides to APO 2 (mismatch or reverse polarity, see text below and FIGS. 23 and 24). Note that APO 6 also showed evidence of toxicity as seen by the general decrease in total protein (FIG. 23).

To further investigate the efficacy of HIAP1 antisense oligonucleotides under cycloheximide induction conditions, changes in HIAP1 mRNA were measured by TaqMan real time PCR 6 hours after transfection with APO 2, which targets an Alu repeat within an intron of HIAP1 and results in the greatest block of CHX-induced upregulation of HIAP1 mRNA and protein. Controls for this experiment were three oligonucleotides for APO 2: one scrambled sequence (same base composition but random order, 5'-AAGGGCGGCG-GAGTGAGAC-3'; SEQ ID NO: 297), one reverse polarity (same base composition, same sequential order but in the opposite direction, 5'-AGAGGACGGAGTCGGAGGC-3'; SEQ ID NO: 298), and one mismatch sequence (containing four base mismatches out of 19 bases, 5'-CGGAGCGTGAG-GATGGAGA-3'; SEQ ID NO: 299).

Transfection of the APO 2 antisense into cells resulted in a 50% decrease in mRNA compared to a scrambled survivin control and matched perfectly with the protein results, while the scrambled control for APO 2 (H1 sc apo 2 in FIG. 24) did not change HIAP1 mRNA levels at all (repeated twice here, and in two different experiments). However, the mismatch control ODN (H1 mm apo 2) and the reverse polarity control oligonucleotide (H1 RV apo 2) showed an induction of 6 to 7 fold in HIAP1 mRNA at 6 hours. These oligonucleotides no longer targeted HIAP1, as expected, but may still target Alu repeats because of the degeneracy and repeat nature of these sequences. Therefore, it is possible that these two controls are toxic to the cell and cause a stress response that leads to the induction of HIAP1. This effect may also occur with the antisense APO 2 oligonucleotide, but in this case, APO 2 also causes the degradation of the induced HIAP1 mRNA which results in a relative decrease of HIAP1 mRNA, compared to a scrambled survivin control, as well as decreasing the relative fold induction of HIAP1 protein after transfection and CHX treatment, compared to scrambled survivin control oligonucleotide.

The six antisense HIAP1 nucleobase oligomers include two very effective oligonucleotides against an intronic sequence (APO 1, and APO 2, with APO 2 demonstrating the better activity). These oligonucleotides could be used therapeutically for treatment of cancer or autoimmune disorders. The oligonucleotides against an intronic sequence would likely only target pre-mRNA (very short-lived target) and not the mature, processed form of HIAP1. Typically, introns are not targeted for antisense except when one wants to alter splicing by targeting the intron-exon boundaries or the branching point. These usually result in the skipping of an exon rather than RNase-mediated degradation of the message. Both mechanisms would likely be favorable for the enhancement of apoptosis, as the skipping would result in the loss of the exon encoding the first two important BIR domains of HIAP1. The APO 2 antisense ODN also targets an intron of survivin for 18 consecutive bases out of 19, but we did not see any loss of survivin protein; only HIAP1 was decreased after the oligo treatment, demonstrating the specificity of the HIAP1 antisense oligonucleotide. These antisense oligonucleotides hit Alu sequences in the HIAP1 intron and potentially in many other genes, and induce the cancer cells to die (see below), which may be as a result of down regulating HIAP1 and some other critical genes, and thus of therapeutic value if it is not too toxic to normal cells.

Cancer cells have reportedly more Alu-containing transcripts and may therefore be more sensitive to apoptosis induction with an Alu targeting nucleobase oligomer. Furthermore, this killing effect of nucleobase oligomers APO 1 and APO 2 may be due to the combined effect of both targeting Alu sequences and HIAP1 simultaneously. This dual effect would result in an effective way to prevent the normal stress response of HIAP1 induction through the NFkB pathway, when the cell is exposed to certain toxic agents. This stress response is most likely part of the cancer cell's anti-apoptotic program. By blocking HIAP1 expression, we counter this anti-apoptotic stress response and precipitate the cancer cell's demise.

EXAMPLE 15

HIAP1 Antisense Oligonucleotides Increase Cytotoxicity and Chemosensitization

The effect of HIAP1 antisense nucleobase oligomers on the chemosentization of SF295 cells was also evaluated. Cells were transfected with one of three different antisense oligonucleotides (APO 7, APO 15, and SC APO 2 (control)). Twenty-four hours after transfection with the oligonucleotides, the cells were incubated with adriamycin for an additional 24 hours before assaying by for cell survival by assaying WST-1.

Figure 25:
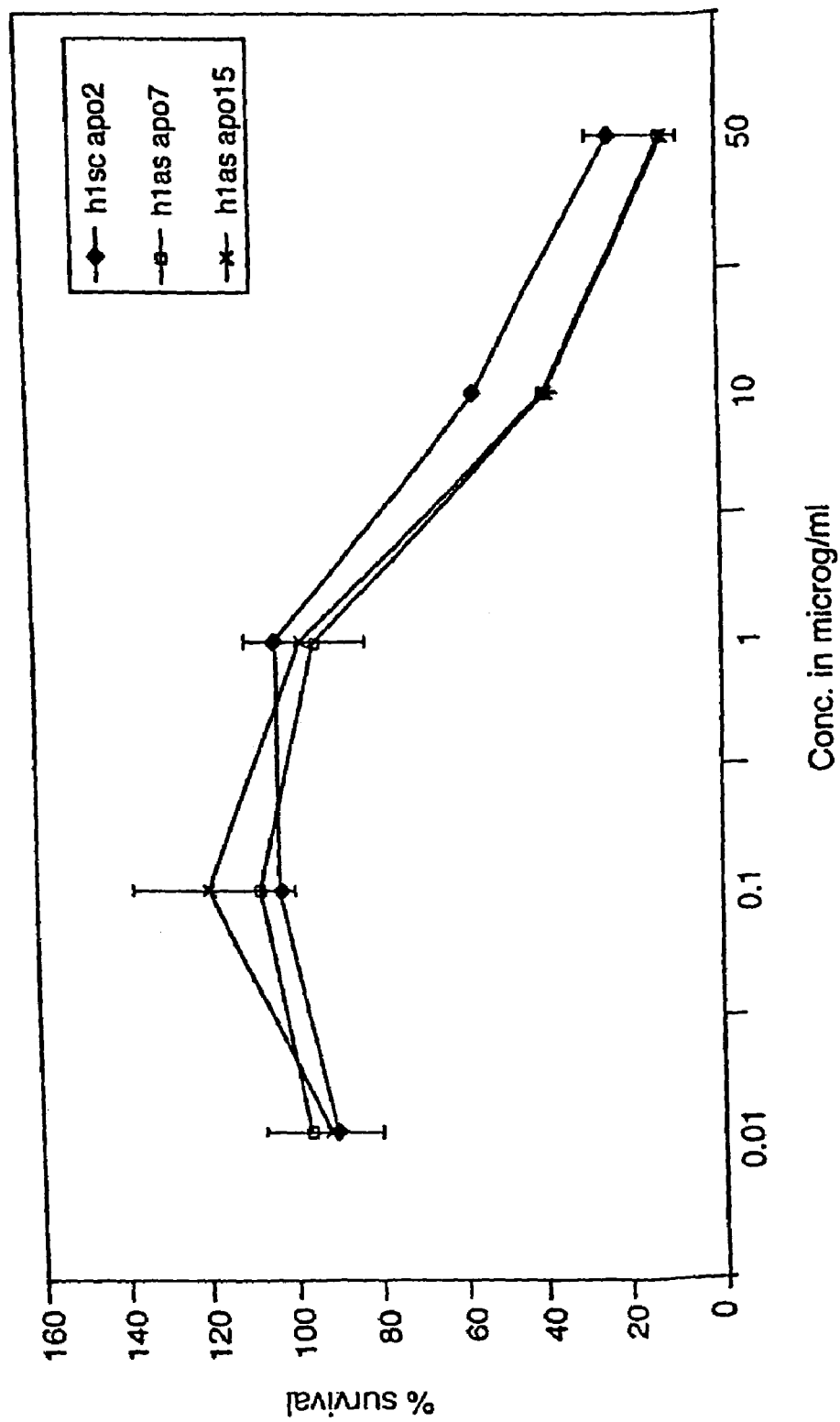
FIG. 25 is a graph showing the effect of HIAP1 oligonucleotides on the chemosensitization of drug-resistant SF295 glioblastomas.

The WST-1 survival curves for SF295 cells transfected with the above-described HIAP1 oligonucleotides and then treated with increasing concentrations of adriamycin are shown in FIG. 25. The two oligonucleotides that resulted in a decrease in HIAP1 mRNA also showed a decrease in survival when treated with adriamycin compared to cells treated with an oligonucleotide that did not reduce HIAP1 mRNA levels. Therefore, reducing HIAP1 levels by antisense, or other means, can chemosensitize a glioblastoma cell line that is highly resistant to the cytotoxic action of many chemotherapeutic drugs.

An additional 89 HIAP1 antisense sequences that can be employed in the methods of the invention are shown in Table 6. Sequences that are 100% identical between human HIAP1 and human HIAP2, or have one or two mismatches, are in bold.

TABLE 6

| Nucleobase oligomer sequence | SEQ ID NO: |
|---|---|
| AGCAAGGACAAGCCCAGTC | 300 |
| TGTAAACCTGCTGCCCAGA | 301 |
| AGAAGTCGTTTTCCTCCTT | 302 |
| CCGAGATTAGACTAAGTCC | 303 |
| ACTTTTCCTTTATTTCCAC | 304 |
| TCCCAAACACAGGTACTAT | 305 |
| CATTCTCAGCGGTAACAGC | 306 |
| ACCATCATTCTCATCCTCA | 307 |
| AATGTAACCTTCAACCATC | 308 |
| TTTGTATTCATCACTGTC | 309 |
| TCACATCTCATTACCAAC | 310 |
| CCAGGTGGCAGGAGAAACA | 311 |
| TGCAGACTTCAATGCTTTG | 312 |
| TAAGCAAGTCACTGTGGCT | 313 |
| CTGAGTCGATAATACTAGC | 314 |
| ACTAGCCATTAGTAAAGAG | 315 |
| CAACAGCAGAGACCTTGTC | 316 |
| ATAGCATACCTTGAACCAG | 317 |
| CATCTGTAGGCTAAGATGG | 318 |
| AGTTACCAGATGCCATCTG | 319 |
| AATCTACTCTGATAGTGGA | 320 |
| GTTTCTGAAGCCAACATCA | 321 |
| TCAACTTATCACCTCCTGA | 322 |
| AAGAACTAACATTGTAGAG | 323 |
| GTAGACAACAGGTGCTGCA | 324 |
| ATGTCCTCTGTAATTATGG | 325 |
| TACTTGGCTAGAACATGGA | 326 |
| GAAGCAACTCAATGTTAAG | 327 |
| TTTGGTCTTTTGGACTCAG | 328 |
| CCATAGATCATCAGGAATA | 329 |
| CAGGACTGGCTAACACATC | 330 |
| TTTAATGGCAGGCATCTCC | 331 |
| TTAAGCCATCAGGATGCCA | 332 |
| GCTACAGAGTAAGCTGTGT | 333 |
| CTCTAGGGAGGTAGTTTTG | 334 |

TABLE 6-continued

| Nucleobase oligomer sequence | SEQ ID NO: |
|---|---|
| AAGAAAAGGGACTAGCCTT | 335 |
| CAGTTCACATGACAAGTCG | 336 |
| GACTCCTTTCTGAGACAGG | 337 |
| ATTCACACCAGTGTAATAG | 338 |
| CAGAAGCATTTGACCTTGT | 339 |
| CCAGCATCAGGCCACAACA | 340 |
| TTTCAGTAGGACTGTCTCC | 341 |
| TGCAGCTAGGATACAACTT | 342 |
| AGAGGTAGCTTCCAAGTTG | 343 |
| GAAGTAATGAGTGTGTGGA | 344 |
| GGATTTGATGGAGAGTTTG | 345 |
| GAACTTCTCATCAAGGCAG | 346 |
| AGGTCCTATGTAGTAAAAG | 347 |
| CAATTTTCCACCACAGGCA | 348 |
| CATTATCCTTCGGTTCCCA | 349 |
| CTCAGGTGTTCTGACATAG | 350 |
| GCTCAGATTAGAAACTGTG | 351 |
| CTGCATGTGTCTGCATGCT | 352 |
| TTAACTAGAACACTAGAGG | 353 |
| CATAATAAAAACCCGCACT | 354 |
| CACCATCACAGCAAAAGCA | 355 |
| CTCCAGATTCCCAACACCT | 356 |
| GGAAACCACTTGGCATGTT | 357 |
| GTTCAAGTAGATGAGGGTA | 358 |
| GATAATTGATGACTCTGCA | 359 |
| ATGGTCTTCTCCAGGTTCA | 360 |
| GCATTAATACAGGGGTAT | 361 |
| TAAAGCCCATTTCCACGGC | 362 |
| TGTTTTACCAGGCTTCTAC | 363 |
| GATTTTCTCTGAACTGTC | 364 |
| CTATAATTCTCTCCAGTTG | 365 |
| ACACAAGATCATTGACTAG | 366 |
| TCTGCATTGAGTAAGTCTA | 367 |
| TCTTTTTCCTCAGTTGCTC | 368 |
| GTGCCATTCTATTCTTCCG | 369 |
| GTAGACTATCCAGGATTGG | 370 |
| AGTTCTCTTGCTTGTAAAG | 371 |
| TCGTATCAATCAGTTCTCT | 372 |
| GCAGAGAGTTTCTGAATAC | 373 |

TABLE 6-continued

| Nucleobase oligomer sequence | SEQ ID NO: |
|---|---|
| ATGTCCTGTTGCACAAATA | 374 |
| CTGAAACATCTTCTGTGGG | 375 |
| TTTCTTCTTGTAGTCTCCG | 376 |
| CTTCTTTGTCCATACACAC | 377 |
| GGAATAAACACTATGGACA | 378 |
| CATACTACTAGATGACCAC | 379 |
| TGTACCCTTGATTGTACTC | 380 |
| GAAATGTACGAACTGTACC | 381 |
| GATGTTTTGGTTCTTCTTC | 382 |
| CTATCATTCTCTTAGTTTC | 383 |
| ACACCTGGCTTCATGTTCC | 384 |
| GACTACAGGCACATACCAC | 385 |
| TGCCTCAGCCTGGGACTAC | 386 |
| AGGATGGATTCAAACTCCT | 387 |
| GAGAAATGTGTCCCTGGTG | 388 |
| GCCACAACAGAAGCATTTG | 389 |

We also analyzed human HIAP2 for sequences suitable for use as antisense nucleobase oligomers. Identified sequences are shown in Table 7.

TABLE 7

| Nucleobase oligomer sequence | SEQ ID NO: |
|---|---|
| TTCTGAAAACTCTTCAATG | 390 |
| CTTAGCATAAAGTATCAGT | 391 |
| CAAAAAGTACTGCTTAGC | 392 |
| CAAGATAAAACTTGTCCTT | 393 |
| TATCAGTCATGTTGTAAAC | 394 |
| CTAAATAACCTGTTCATCA | 395 |
| AGCACACTTTTTACACTGC | 396 |
| ACCACTATTATTCTTGATC | 397 |
| TGTATTTGTTTCCATTTCC | 398 |
| ACTGTAAACTCTATCTTTG | 399 |
| CTTAAGTGGGCTAAATTAC | 400 |
| CCTTCATATGGTCACACTA | 401 |
| GGTTACAAGCTATGAAGCC | 402 |
| CTAAGCAACTATAGAATAC | 403 |
| TCCTTGATTTTTCACAGAG | 404 |
| ATACTAACTTAAAGCCCTG | 405 |
| GGGTTGTAGTAACTCTTTC | 406 |

TABLE 7-continued

| Nucleobase oligomer sequence | SEQ ID NO: |
|---|---|
| TAGAACACAACTCTTTGGG | 407 |
| CTCTGAATTTCCAAGATAC | 408 |
| TTTACTGGATTTATCTCAG | 409 |
| TGAGTAGGTGACAGTGCTG | 410 |
| GGAGGCAGTTTTGTGCATG | 411 |
| CTATCTTCCATTATACTCT | 412 |
| TTGTTTGTTGCTGTTTGTC | 413 |
| TCCTTTCTGAGACAGGCAC | 414 |
| ACCAGCACGAGCAAGACTC | 415 |
| ACCTTGTCATTCACACCAG | 416 |
| TCCAGTTATCCAGCATCAG | 417 |
| GCTTTTGAATAGGACTGTC | 418 |
| GAGATGTCTTCAACTGCTC | 419 |
| GGGGTTAGTCCTCGATGAA | 420 |
| TCATTGCATAACTGTAGGG | 421 |
| GCTCTTGCCAATTCTGATG | 422 |
| ACCCTATCTCCAGGTCCTA | 423 |
| ACAGGCAAAGCAGGCTACC | 424 |
| GTTCTGACATAGCATCATC | 425 |
| CTCAGAGTTTCTAGAGAAT | 426 |
| ATGTTCTCATTCGAGCTGC | 427 |
| TGAACTGGAACACTAGATG | 428 |
| GCTCAGGCTGAACTGGAAC | 429 |
| TTGACATCATCATTGCGAC | 430 |
| ACCATCACAACAAAAGCAT | 431 |
| CCACTTGGCATGTTCTACC | 432 |
| TCGTATCAAGAACTCACAC | 433 |
| GGTATCTGAAGTTGACAAC | 434 |
| TTTCTTCTCCAGTGGTATC | 435 |
| TTCTCCAGGTCCAAAATGA | 436 |
| ACAGCATCTTCTGAAGAAC | 437 |
| CACAGGTGTATTCATCATG | 438 |

TABLE 7-continued

| Nucleobase oligomer sequence | SEQ ID NO: |
|---|---|
| CCAGGTCTCTATTAAAGCC | 439 |
| TTCTCTCCAGTTGTCAGGA | 440 |
| GAAGTGCTGACACAATATC | 441 |
| TTTTCCTTCTCCTCCTCTC | 442 |
| CATCTGATGCCATTTCTTC | 443 |
| AGCCATTCTGTTCTTCCGA | 444 |
| CCAGGATAGGAAGCACACA | 445 |
| ATGGTATCAATCAGTTCTC | 446 |
| CCGCAGCATTTCCTTTAAC | 447 |
| CAGTTTTTGAAGATGTTGG | 448 |
| GTGACAGACCTGAAACATC | 449 |
| GGGCATTTTCTTAGAGAAG | 450 |
| AGTACCCTTGATTATACCC | 451 |
| GAAATGTACGAACAGTACC | 452 |
| TGAAAAACTCATAATTCCC | 453 |
| CCATCTTTTCAGAAACAAG | 454 |
| CTATAATTCTCTCCAGTTG | 455 |
| CTCCCTTAGGTACACATAC | 456 |
| ACAAGCAGTGACACTACTC | 457 |
| GTAACTCCTGAAATGATGC | 458 |
| CAACAAATCCAGTAACTCC | 459 |
| CACCATAACTCTGATGAAC | 460 |

Other Embodiments

All publications and patent applications mentioned in this specification, including U.S. Pat. Nos. 5,919,912, 6,156,535, and 6,133,437, are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

What is claimed is:

1. A method of enhancing apoptosis in a cell in an animal, said method comprising administering to said animal a nucleobase oligomer, said nucleobase oligomer comprising 5'-NGCACCCNGGANACCANNN-3' (SEQ ID NO: 151), wherein "N" is "T" or "U".

2. The method of claim 1, further comprising administering to said animal a chemotherapeutic agent.

3. The method of claim 2, wherein said chemotherapeutic agent is a cytostatic agent.

4. The method of claim 2, wherein said chemotherapeutic agent is a cytotoxic agent.

5. The method of claim 1, further comprising administering to said animal a chemosensitizer.

6. The method of claim 1, further comprising administering to said animal a biological response modifying agent.

7. The method of claim 1, wherein said nucleobase oligomer is administered to said animal intravenously or intratumorally.

8. The method of claim 1, wherein said animal is a human.

9. A method of treating an animal having a cancer, said method comprising administering to said animal a therapeutically effective amount of a nucleobase oligomer, said nucleobase oligomer comprising 5'-NGCACCCNGGANACCANNN-3' (SEQ ID NO: 151), wherein "N" is "T" or "U".

10. The method of claim 9, wherein the cancer is acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, myelodysplastic syndrome, chronic lymphocytic leukemia, polycythemia vera, lymphoma, Hodgkin's disease Waldenstrom's macroglobulinemia, fibrosarcoma, myxosarcoma, liposarcoma, chondrosarcoma, osteogenic sarcoma, chordoma, angiosarcoma, endotheliosarcoma, lymphangiosarcoma, hepatocellular carcinoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, or retinoblastoma.

11. The method of claim 9, further comprising administering to said animal a chemotherapeutic agent.

12. The method of claim 11, wherein said nucleobase oligomer and said chemotherapeutic agent are administered to said animal within five days of each other.

13. The method of claim 12, wherein said nucleobase oligomer and said chemotherapeutic agent are administered to said animal within twenty-four hours of each other.

14. The method of claim 11, wherein said chemotherapeutic agent is doxorubicin, vinorelbine, etoposide, paclitaxel or cisplatin.

15. The method of claim 11, wherein said chemotherapeutic agent is a cytostatic agent.

16. The method of claim 11, wherein said chemotherapeutic agent is a cytotoxic agent.

17. The method of claim 9, further comprising administering to said animal a chemosensitizer.

18. The method of claim 9, further comprising administering to said animal a biological response modifying agent.

19. The method of claim 9, wherein said nucleobase oligomer is administered to said animal intravenously or intratumorally.

20. The method of claim 9, wherein said animal is a human.

21. The method of claim 9, wherein said nucleobase oligomer is an oligonucleotide.

22. The method of claim 21, wherein said oligonucleotide comprises at least one modified linkage.

23. The method of claim 22, wherein said modified linkage is selected from the group consisting of phosphorothioate, methylphosphonate, phosphotriester, phosphorodithioate, and phosphoselenate linkages.

24. The method of claim 9, wherein said nucleobase oligomer comprises at least one modified sugar moiety.

25. The method of claim 24, wherein said modified sugar moiety is a 2'-O-methyl group or a 2'-O-methoxyethyl group.

26. The method of claim 9, wherein said nucleobase oligomer comprises at least one modified nucleobase.

27. The method of claim 26, wherein said modified nucleobase is 5-methyl cytosine.

28. The method claim 9, wherein said nucleobase oligomer is a chimeric nucleobase oligomer.

29. The method of claim 28, wherein said nucleobase oligomer comprises DNA residues linked together by phosphorothioate linkages, said DNA residues flanked on each side by at least one 2'-O-methyl or 2'-O-methoxyethyl RNA residue.

30. The method of claim 29, wherein said DNA residues are flanked on each side by at least three 2'-O-methyl or 2'-O-methoxyethyl RNA residues.

31. The method of claim 30, wherein said DNA residues are flanked on each side by four 2'-O-methyl or 2'-O-methoxyethyl RNA residues.

32. The method of claim 29, wherein said RNA residues are linked together by phosphorothioate linkages, and said RNA residues are linked to said DNA residues by phosphorothioate linkages.

33. The method of claim 28, wherein said nucleobase oligomer comprises DNA residues linked together by phosphodiester linkages, said DNA residues flanked on each side by at least two 2'-O-methyl or 2'-O-methoxyethyl RNA residues linked together by phosphorothioate linkages.

34. The method of claim 33, wherein said DNA residues are flanked on each side by at least three 2'-O-methyl or 2'-O-methoxyethyl RNA residues.

35. The method of claim 1, wherein said nucleobase oligomer consists essentially of 5'-NGCACCCNGGANACCANNN-3' (SEQ ID NO: 151), wherein "N" is "T" or "U".

36. The method of claim 1, wherein said nucleobase oligomer consists of 5'-NGCACCCNGGANACCANNN-3' (SEQ ID NO: 151), wherein "N" is "T" or "U".

37. The method of claim 9, wherein said nucleobase oligomer consists essentially of 5'-NGCACCCNGGANACCANNN-3' (SEQ ID NO: 151), wherein "N" is "T" or "U".

38. The method of claim 9, wherein said nucleobase oligomer consists of 5'-NGCACCCNGGANACCANNN-3' (SEQ ID NO: 151), wherein "N" is "T" or "U".

39. The method of claim 1, wherein said nucleobase oligomer comprises 5'-UGCACCCTGGATACCAUUU-3' (SEQ ID NO: 151).

40. The method of claim 9, wherein said nucleobase oligomer comprises 5'-UGCACCCTGGATACCAUUU-3' (SEQ ID NO: 151).

41. The method of claim 1, wherein said nucleobase oligomer consists of 5'-UGCACCCTGGATACCAUUU-3' (SEQ ID NO: 151).

42. The method of claim 9, wherein said nucleobase oligomer consists of 5'-UGCACCCTGGATACCAUUU-3' (SEQ ID NO: 151).

43. The method of claim 1, wherein said nucleobase oligomer comprises eleven DNA residues flanked on each side by four 2'-O-methyl RNA residues, said nucleobase oligomer consisting of 5'-UGCACCCTGGATACCAUUU-3' (SEQ ID NO: 151).

44. The method of claim 9, wherein said nucleobase oligomer comprises eleven DNA residues flanked on each side by four 2'-O-methyl RNA residues, said nucleobase oligomer consisting of 5'-UGCACCCTGGATACCAUUU-3' (SEQ ID NO: 151).

* * * * *